United States Patent
Henniges et al.

(10) Patent No.: US 11,357,877 B2
(45) Date of Patent: Jun. 14, 2022

(54) STERILIZATION ENCLOSURE FOR SURGICAL INSTRUMENTS

(71) Applicant: Stryker Corporation, Kalamazoo, MI (US)

(72) Inventors: Bruce Henniges, Galesburg, MI (US);
Robert Childers, Trinity, FL (US);
Erik Chmelar, Midland, MI (US);
Adam Dudycha, Paw Paw, MI (US);
Michael Miller, Kalamazoo, MI (US);
Ali Moaiery, Kalamazoo, MI (US);
Benjamin John Purrenhage, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 1133 days.

(21) Appl. No.: 15/759,025

(22) PCT Filed: Sep. 10, 2016

(86) PCT No.: PCT/US2016/051181
§ 371 (c)(1),
(2) Date: Mar. 9, 2018

(87) PCT Pub. No.: WO2017/044906
PCT Pub. Date: Mar. 16, 2017

(65) Prior Publication Data
US 2020/0237939 A1     Jul. 30, 2020

Related U.S. Application Data

(60) Provisional application No. 62/300,368, filed on Feb. 26, 2016, provisional application No. 62/217,192, filed on Sep. 11, 2015.

(51) Int. Cl.
*A61L 2/07*   (2006.01)
*A61L 2/28*   (2006.01)
(Continued)

(52) U.S. Cl.
CPC ............................ *A61L 2/07* (2013.01);
*A61L 2/28* (2013.01); *G01K 3/04* (2013.01);
*G01K 11/06* (2013.01);
(Continued)

(58) Field of Classification Search
CPC .. G01K 3/04; G01K 11/06; A61L 2/07; A61L 2/28; A61L 2202/122; A61L 2202/24
See application file for complete search history.

(56) References Cited

U.S. PATENT DOCUMENTS 2,847,067 A  *  8/1958  Brewer .................... A61L 2/28
                                                        374/160
3,063,235 A     11/1962  Winchell
(Continued)

FOREIGN PATENT DOCUMENTS

CN          1034393 A      8/1989
CN          1474704 A      2/2004
(Continued)

OTHER PUBLICATIONS

English language abstract and machine-assisted English translation for CN 2616210 extracted from espacenet.com database on Jan. 18, 2021, 6 pages.

(Continued)

*Primary Examiner* — Sean E Conley
(74) *Attorney, Agent, or Firm* — Howard & Howard Attorneys PLLC

(57) ABSTRACT

A sterilization enclosure comprises one or more sensors for measuring characteristics within the container during a sterilization process, including one or more characteristics of sterilization agent(s), to determine whether instruments disposed within the container have been exposed to threshold process conditions to ensure a desired level of sterilization for those instruments.

23 Claims, 59 Drawing Sheets

(51) Int. Cl.
  *G01K 3/04* (2006.01)
  *G01K 11/06* (2006.01)
(52) U.S. Cl.
  CPC ..... *A61L 2202/122* (2013.01); *A61L 2202/24* (2013.01)

(56) References Cited

U.S. PATENT DOCUMENTS

| | | | |
|---|---|---|---|
| 4,270,039 | A | 5/1981 | Hauser |
| 4,353,990 | A | 10/1982 | Manske et al. |
| 4,448,548 | A | 5/1984 | Foley |
| 4,671,943 | A * | 6/1987 | Wahlquist ............ A61L 2/26 422/300 |
| 4,805,188 | A | 2/1989 | Parker |
| 5,087,508 | A | 2/1992 | Beck |
| 5,158,363 | A | 10/1992 | Speelman et al. |
| 5,378,430 | A | 1/1995 | Nieves et al. |
| 5,602,804 | A | 2/1997 | Haas |
| 5,709,472 | A | 1/1998 | Prusik et al. |
| 5,788,925 | A | 8/1998 | Pai et al. |
| 6,071,021 | A | 6/2000 | Gagliardo |
| 6,108,489 | A | 8/2000 | Frohlich et al. |
| 6,269,680 | B1 | 8/2001 | Prieve et al. |
| 6,318,151 | B1 | 11/2001 | Wang et al. |
| 6,517,775 | B1 | 2/2003 | Wang et al. |
| 6,528,016 | B1 | 3/2003 | Kohler et al. |
| 6,532,794 | B2 | 3/2003 | Wang et al. |
| 6,537,491 | B1 | 3/2003 | Wang et al. |
| 6,612,149 | B2 | 9/2003 | Wang et al. |
| 6,875,399 | B2 | 4/2005 | McVey |
| 6,930,493 | B2 | 8/2005 | Kaiser et al. |
| 7,090,808 | B2 | 8/2006 | Caputo et al. |
| 7,118,029 | B2 | 10/2006 | Nycz et al. |
| 7,122,150 | B2 | 10/2006 | Gonzalez et al. |
| 7,157,045 | B2 | 1/2007 | McVey |
| 7,701,334 | B1 | 4/2010 | Perkins et al. |
| 7,827,845 | B2 | 11/2010 | Kraus |
| 7,880,887 | B2 | 2/2011 | Olson et al. |
| 8,056,719 | B2 | 11/2011 | Porret et al. |
| 9,393,077 | B2 | 7/2016 | Schuster |
| 9,404,808 | B2 | 8/2016 | Park et al. |
| 9,789,218 | B2 | 10/2017 | Motz et al. |
| 10,022,464 | B2 | 7/2018 | Sarphati et al. |
| 10,967,079 | B2 | 4/2021 | Sarphati et al. |
| 2002/0022246 | A1 | 2/2002 | Lin et al. |
| 2003/0211618 | A1 | 11/2003 | Patel |
| 2006/0240563 | A1 | 10/2006 | Kippenhan et al. |
| 2007/0245947 | A1 | 10/2007 | Riemelmoser |
| 2008/0085210 | A1 | 4/2008 | Griesbach et al. |
| 2009/0047176 | A1 | 2/2009 | Cregger et al. |
| 2011/0192744 | A1* | 8/2011 | Parker ............ A61B 50/30 206/363 |
| 2011/0275159 | A1 | 11/2011 | Landgrebe et al. |
| 2012/0034131 | A1 | 2/2012 | Rubinsky et al. |
| 2012/0095605 | A1 | 4/2012 | Tran |
| 2012/0095606 | A1 | 4/2012 | Besore et al. |
| 2012/0156090 | A1 | 6/2012 | Dane et al. |
| 2014/0224687 | A1 | 8/2014 | Schuster |
| 2015/0374868 | A1 | 12/2015 | Bruce et al. |
| 2016/0045630 | A1 | 2/2016 | Motz et al. |
| 2017/0000919 | A1 | 1/2017 | Childers et al. |

FOREIGN PATENT DOCUMENTS

| | | |
|---|---|---|
| CN | 2616210 Y | 5/2004 |
| CN | 2885165 Y | 4/2007 |
| CN | 1989399 A | 6/2007 |
| CN | 101186806 A | 5/2008 |
| CN | 104117082 A | 10/2014 |
| CN | 104501994 A | 4/2015 |
| CN | 105136330 A | 12/2015 |
| CN | 105806507 A | 7/2016 |
| DE | 102012211282 A1 | 1/2014 |
| EP | 0058019 A1 | 8/1982 |
| EP | 0227805 A1 | 7/1987 |
| EP | 0648506 A1 | 4/1995 |
| EP | 2520314 B1 | 9/2015 |
| FR | 2582397 A1 | 11/1986 |
| GB | 563439 A | 8/1944 |
| JP | S5628763 A | 3/1981 |
| JP | S57150964 A | 9/1982 |
| JP | H07171206 A | 7/1995 |
| JP | 2002515970 A | 5/2002 |
| JP | 2005514170 A | 5/2005 |
| JP | 2010505490 A | 2/2010 |
| JP | 2015501180 A | 1/2015 |
| WO | 8908228 A1 | 9/1989 |
| WO | 9524622 A1 | 9/1995 |
| WO | 9719709 A1 | 6/1997 |
| WO | 0186289 A1 | 11/2001 |
| WO | 2008041146 A2 | 4/2008 |
| WO | 2012088064 A1 | 6/2012 |
| WO | WO2012082289 A1 | 6/2012 |
| WO | 2012135694 A2 | 10/2012 |
| WO | 2014159696 A1 | 10/2014 |
| WO | 2015138461 A1 | 9/2015 |

OTHER PUBLICATIONS

English language abstract for CN 104117082 extracted from espacenet.com database on Jan. 18, 2021, 2 pages.
English language abstract for EP 0 227 805 extracted from espacenet.com database on Jan. 18, 2021, 1 page.
English language abstract not found for JPS 56-28763; however, see English language equivalent U.S. Pat. No. 4,270,039. Original document extracted from espacenet.com database on Jan. 18, 2021, 4 pages.
Invitation to Pay Additional Fees/Partial International Search Report for Application No. PCT/US 2016/051181 dated Jan. 20, 2017, 7 pages.
International Search Report for Application No. PCT/US2016/051181 dated May 4, 2017, 4 pages.
Association for the Advancement of Medical Instrumentation, "American National Standard ANSI/AAMI ST77:2013—Containment Devices for Reusable Medical Device Sterilization", 2013, pp. 1-24.
Hamamatsu Photoics K.K., "Micro-Spectrometer C12666MA Brochure", Dec. 2013, 8 pages.
Wallace, John, "LED Optics: Efficient LED Collimators Have Simple Design", LaserFocusWorld, Jun. 5, 2012, 3 pages.
Machine-assisted English translation for CN 1034393 extracted from espacenet.com database on Jul. 29, 2016, 4 pages.
English language abstract and machine-assisted English translation for CN 101186806 extracted from espacenet.com database on Jul. 29, 2016, 6 pages.
English language abstract and machine-assisted English translation for CN 2885165 extracted from espacenet.com database on Jul. 29, 2016, 4 pages.
English language abstract and machine-assisted English translation for CN105136330 extracted from espacenet.com database on Apr. 2, 2018, 27 pages.
English language abstract and machine-assisted English translation for CN 105806507 extracted from espacenet.com database on Apr. 2, 2018, 29 pages.
English language abstract and machine-assisted English translation for DE 10 2012 211 282 extracted from espacenet.com database on Apr. 2, 2018, 18 pages.
English language abstract and machine-assisted English translation for EP 2 520 314 extracted from espacenet.com database on Apr. 2, 2018, 15 pages.
English language abstract and machine-assisted English translation for FR 2 582 397 extracted from espacenet.com database on Apr. 2, 2018, 5 pages.
English language abstract for JPH 07-171206 extracted from espacenet.com database on Apr. 2, 2018, 2 pages.
English language abstract for JP 2010-505490 extracted from espacenet.com database on Apr. 2, 2018, 1 page.

(56) References Cited

OTHER PUBLICATIONS

English language abstract not found for JPS 57-150964; however, see English language equivalent U.S. Pat. No. 4,353,990. Original document extracted from espacenet.com database on Jul. 15, 2020, 9 pages.

English language abstract for JP 2002-515970 extracted from espacenet.com database on Jun. 1, 2020, 1 page.

English language abstract for JP 2005-514170 extracted from espacenet.com database on Jun. 1, 2020, 1 page.

English language abstract for JP 2015-501180 extracted from espacenet.com database on Jun. 15 2020, 2 pages.

English language abstract for CN 1474704 extracted from espacenet.com database on Apr. 9, 2020, 2 pages.

English language abstract for CN 1989399 extracted from espacenet.com database on Apr. 9, 2020, 2 pages.

English language abstract and machine-assisted English translation for CN 104501994 extracted from espacenet.com database on Apr. 9, 2020, 10 pages.

\* cited by examiner

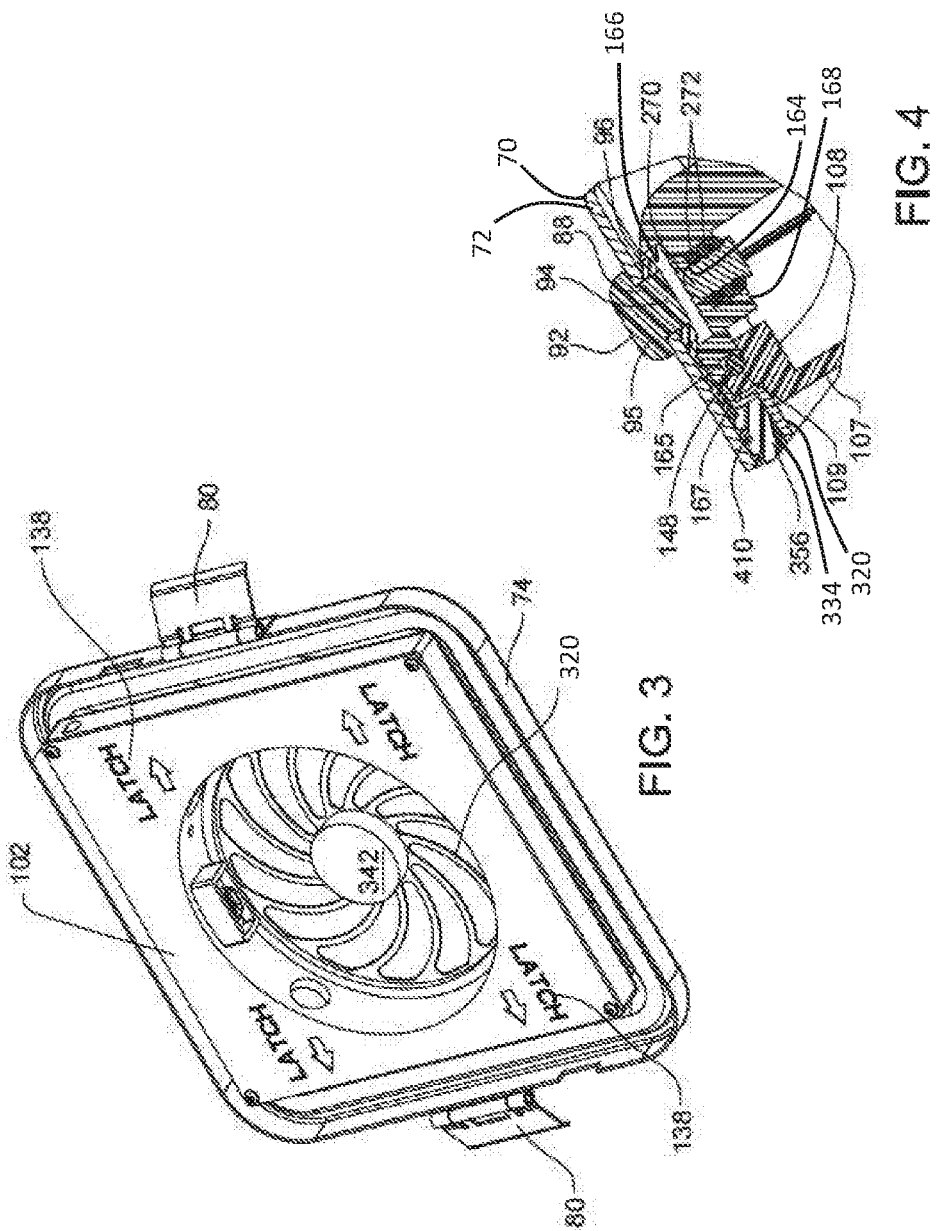

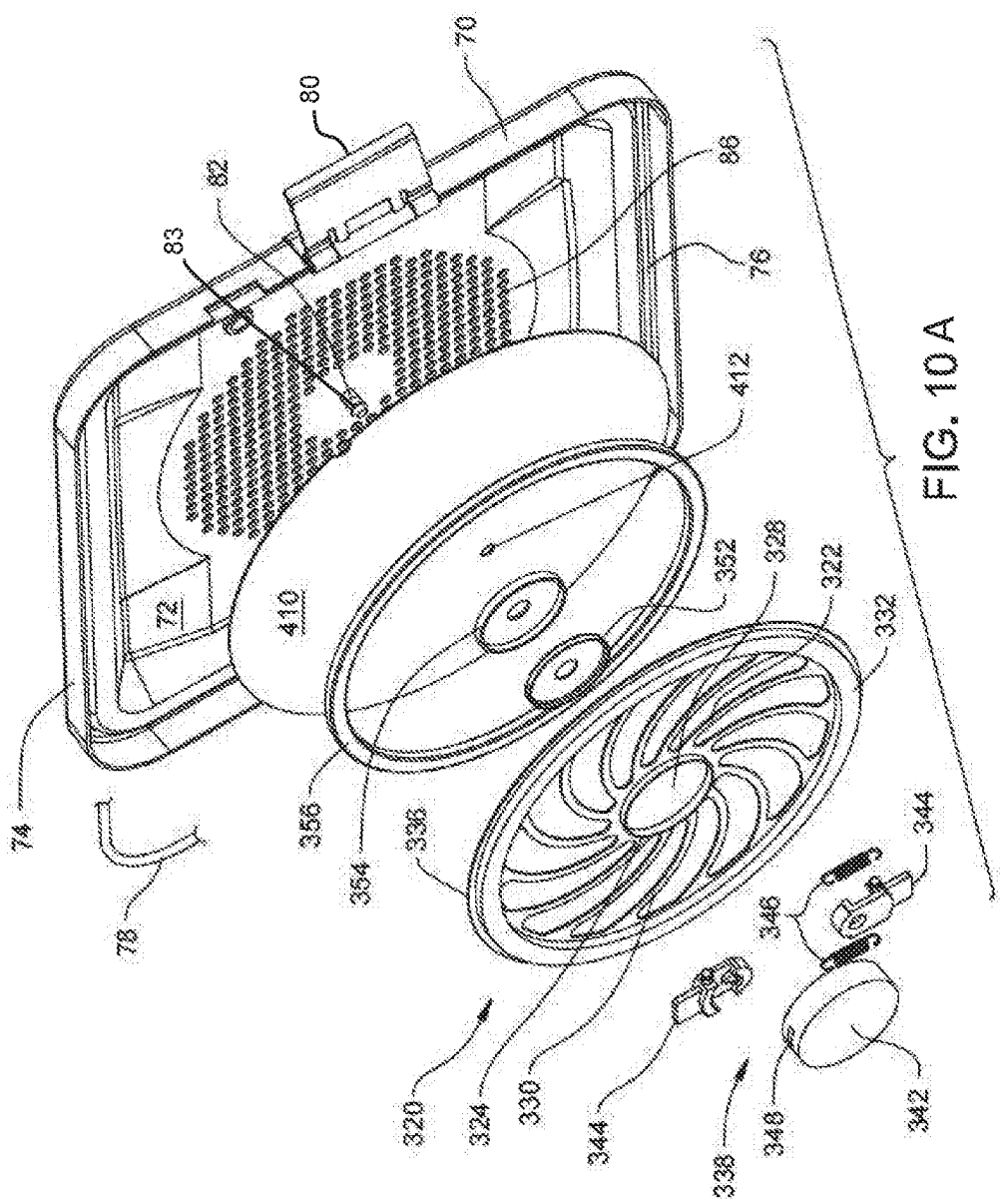

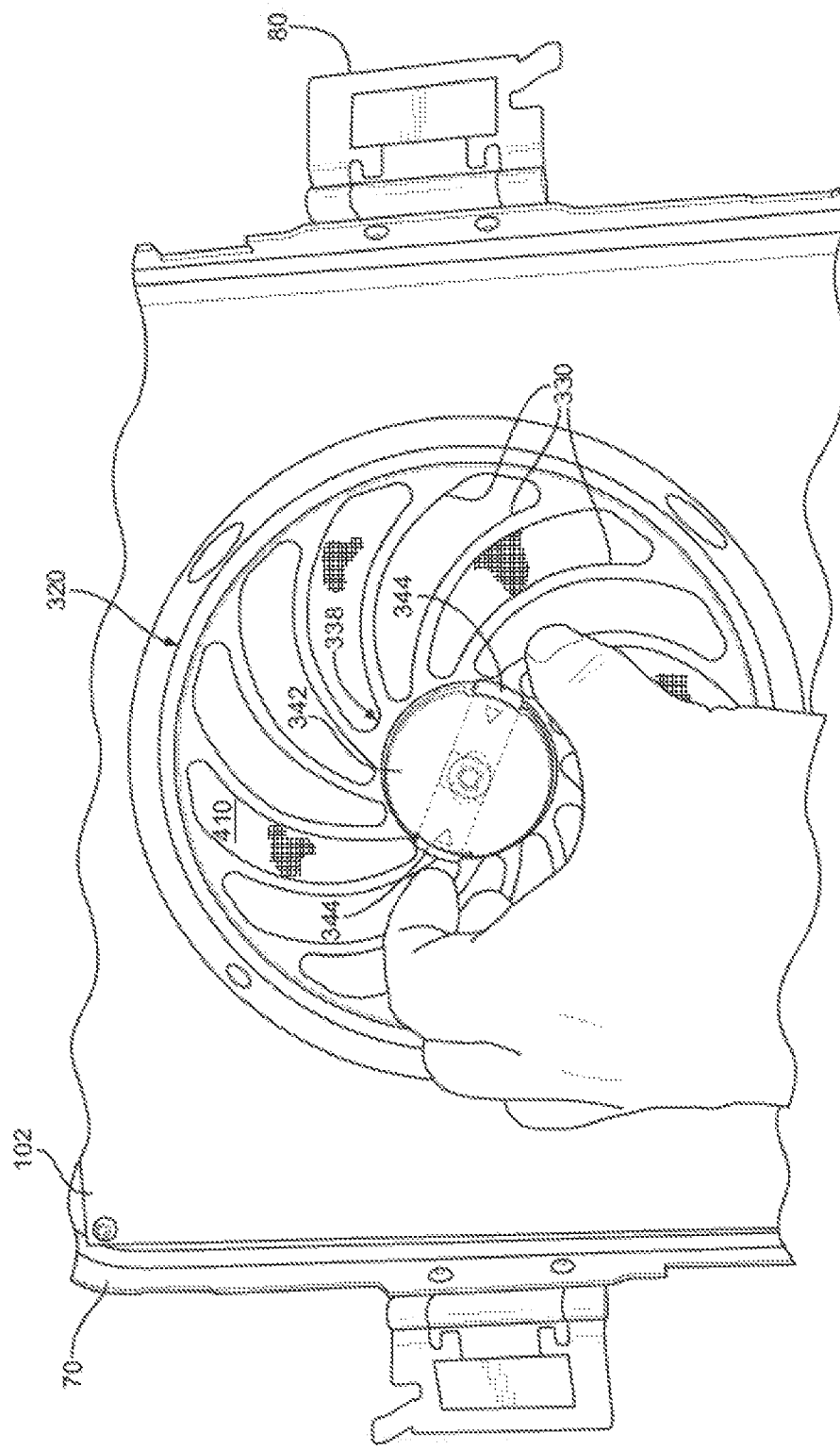

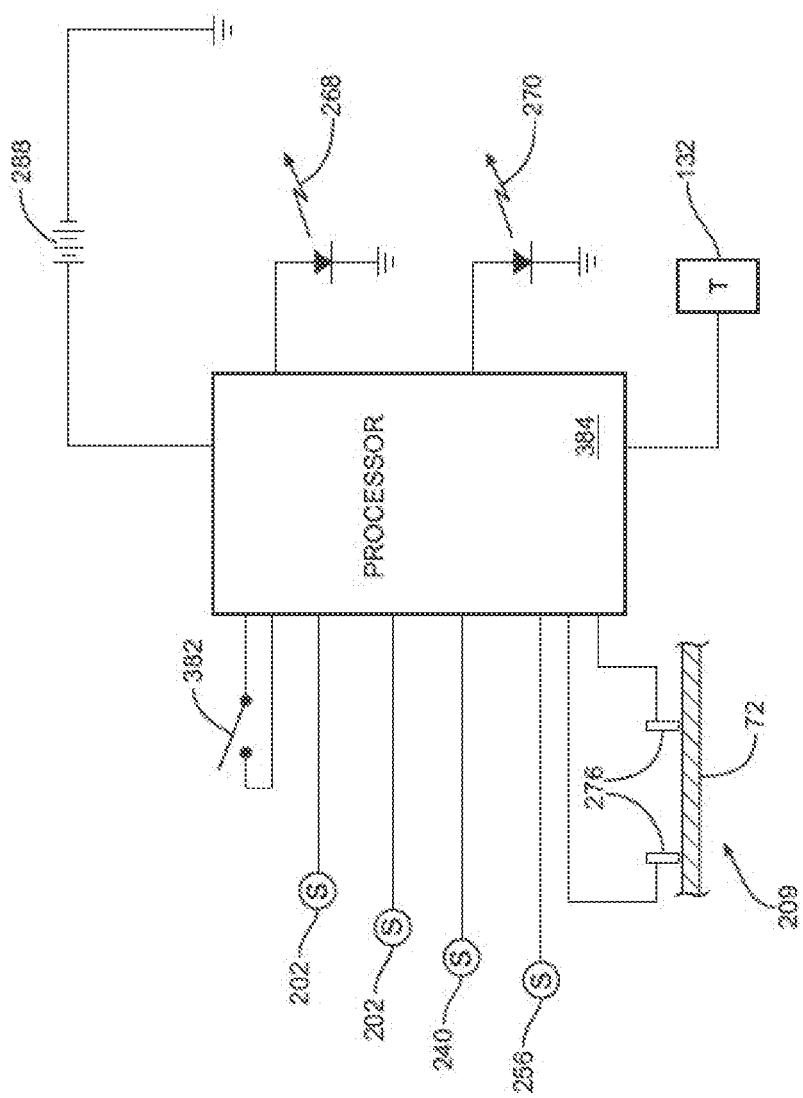

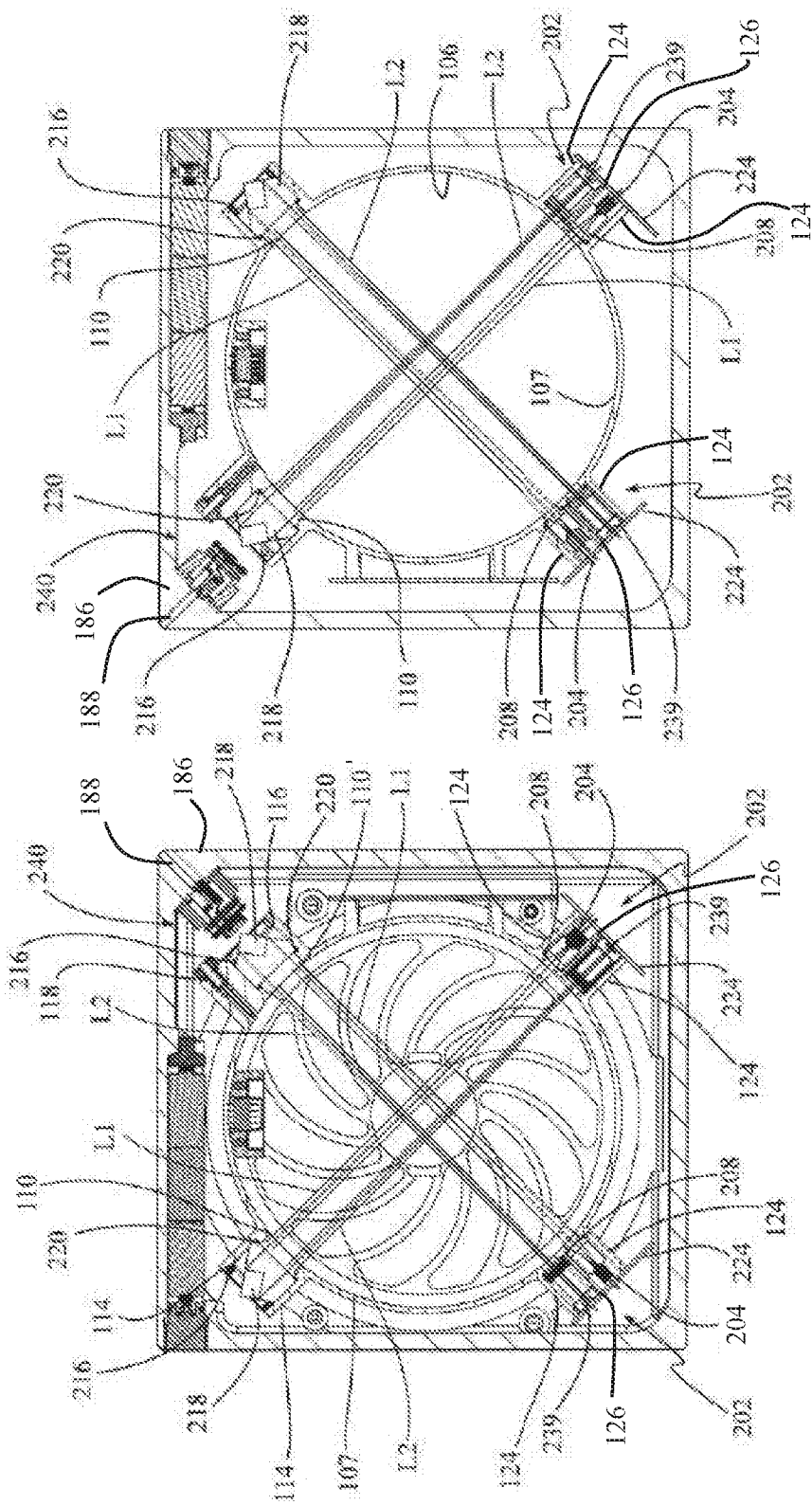

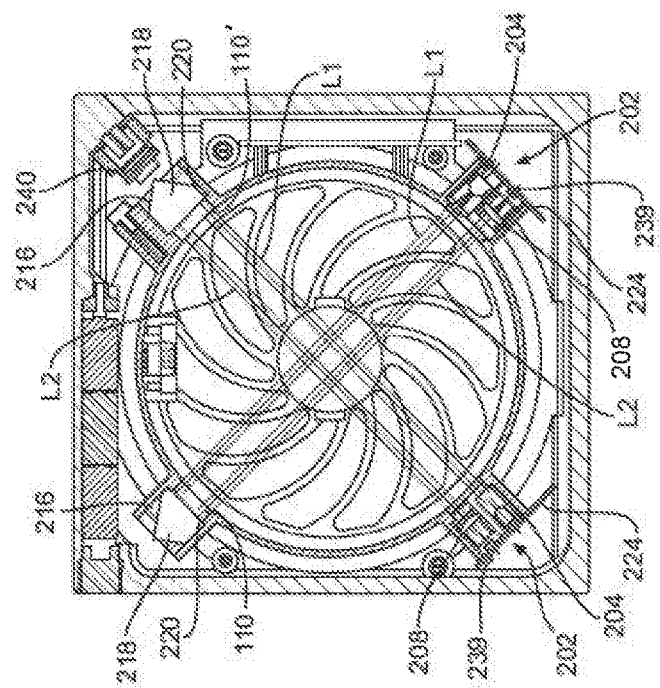

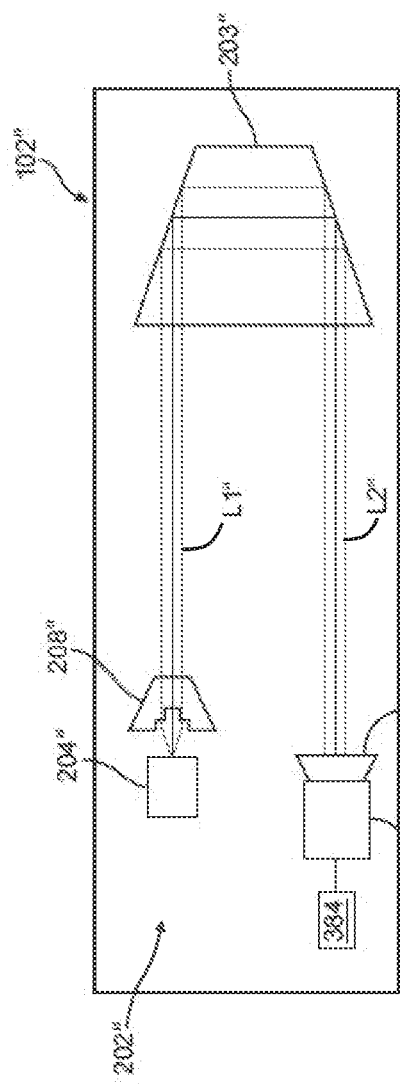
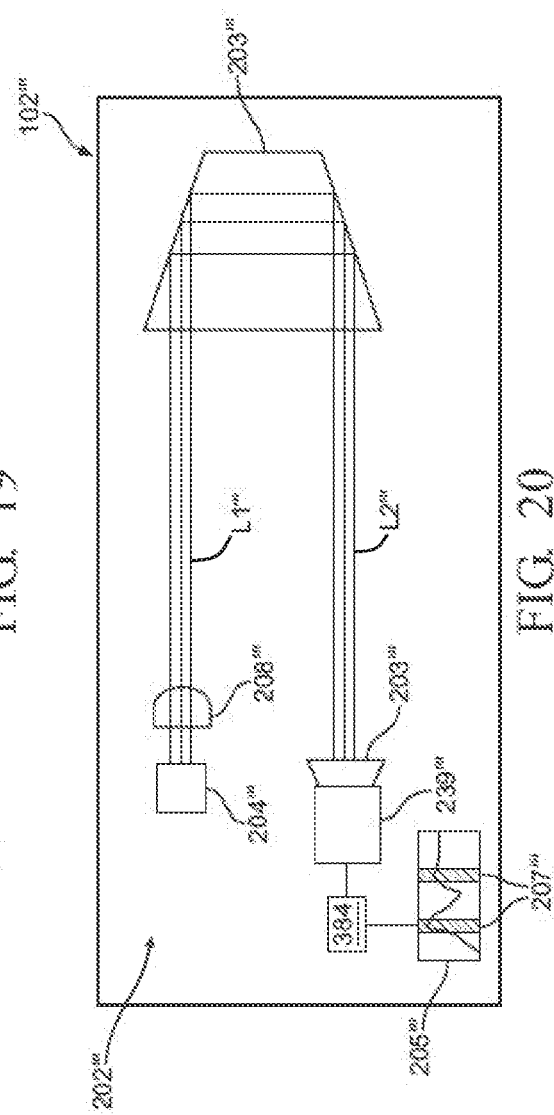

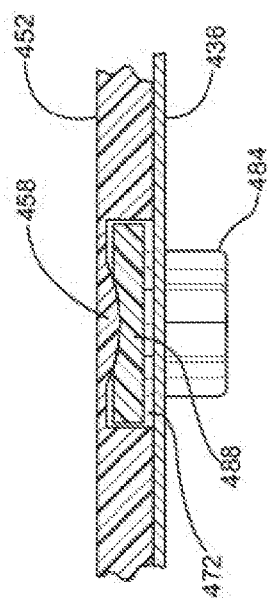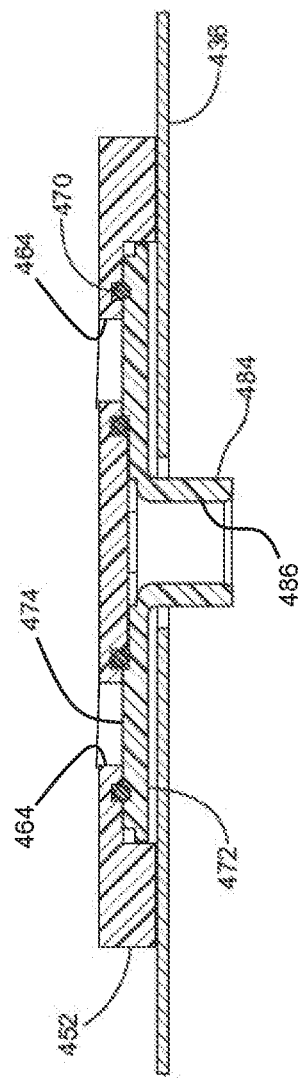

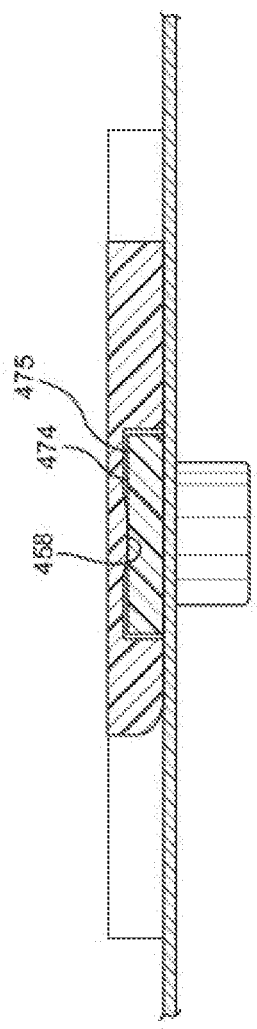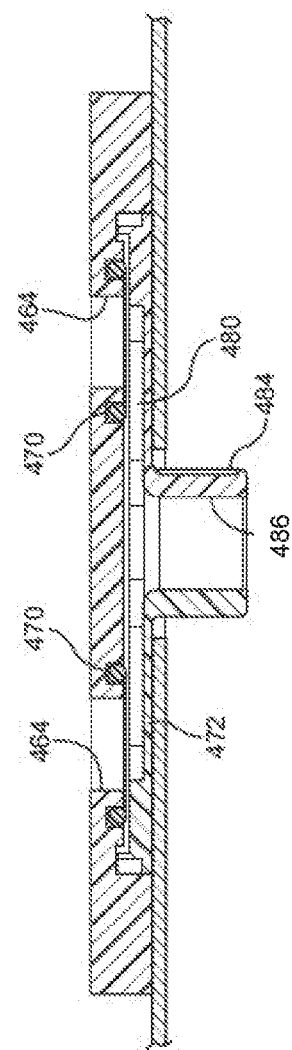

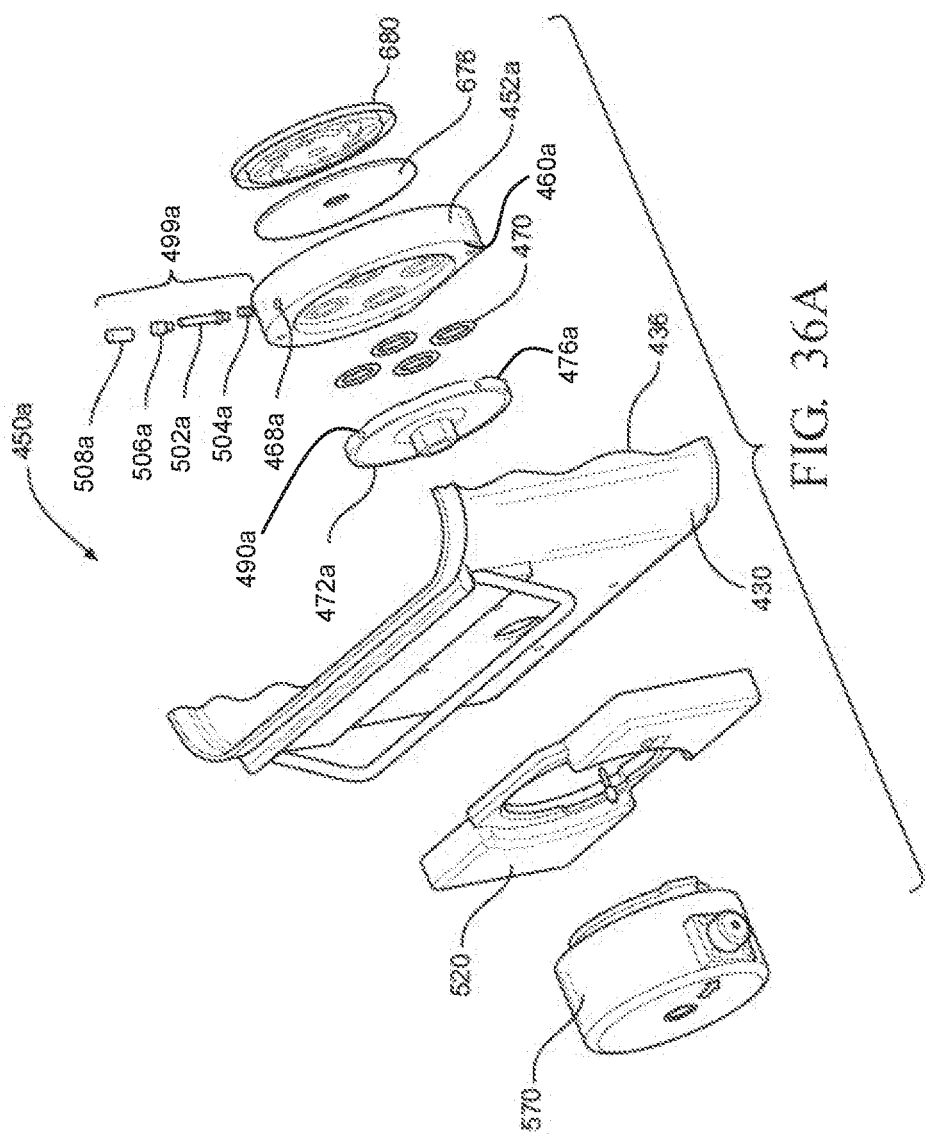

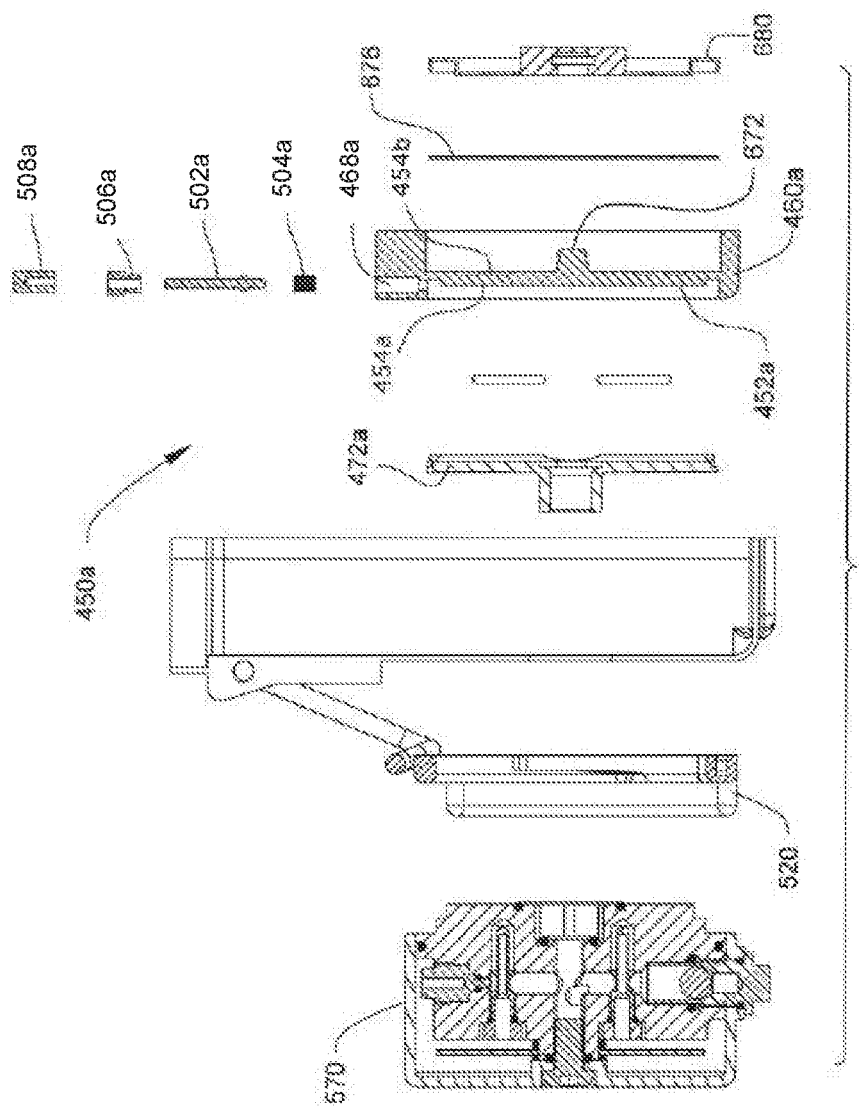

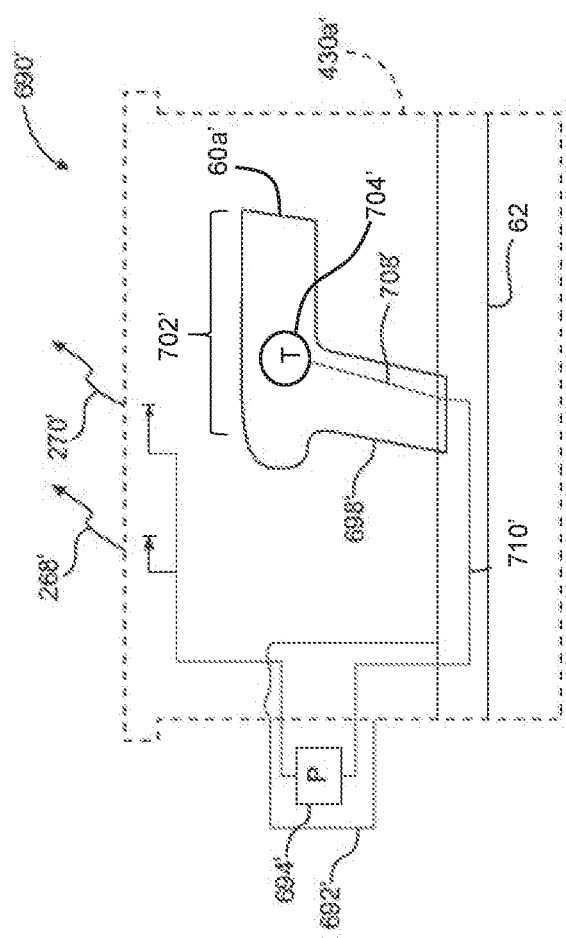

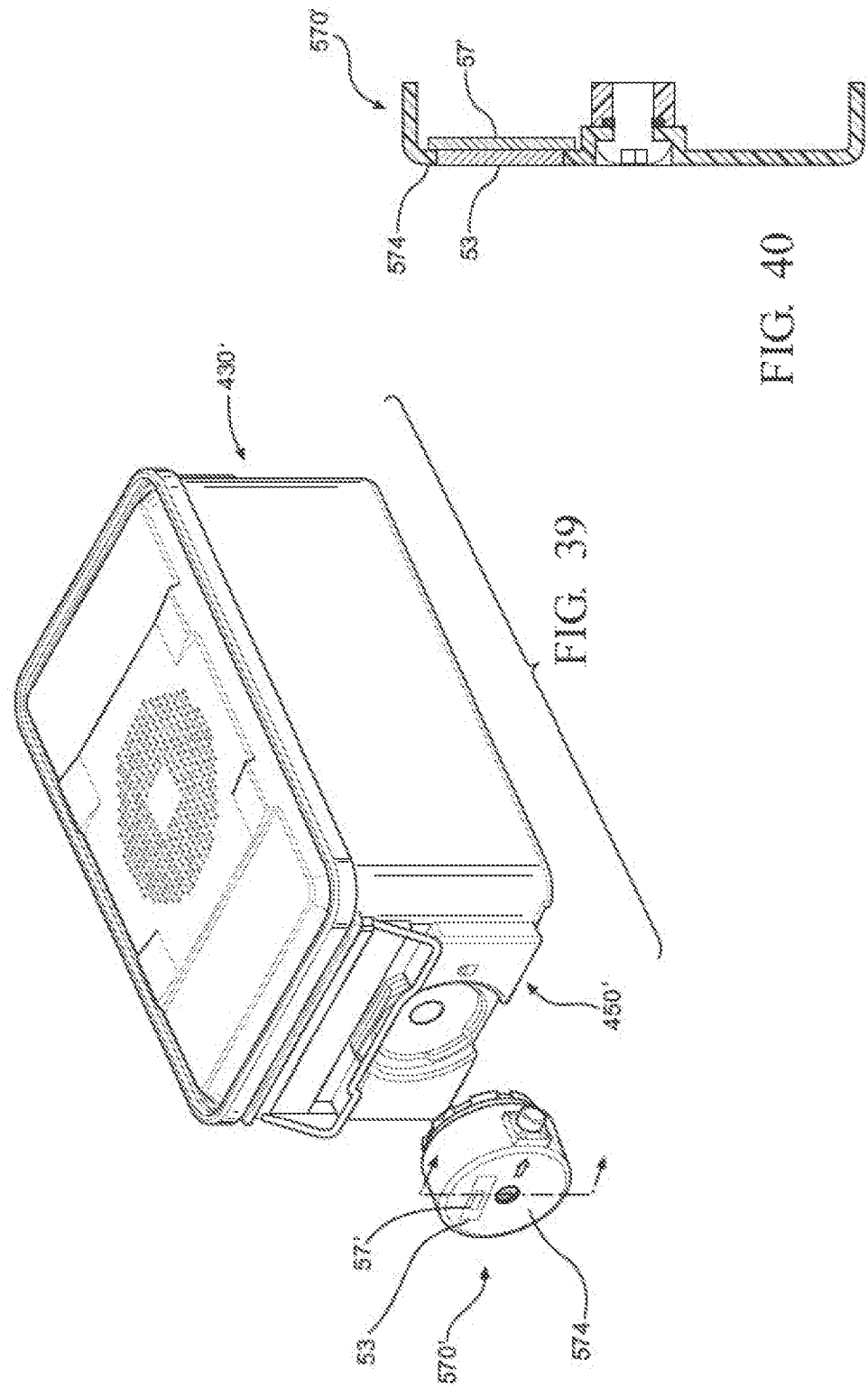

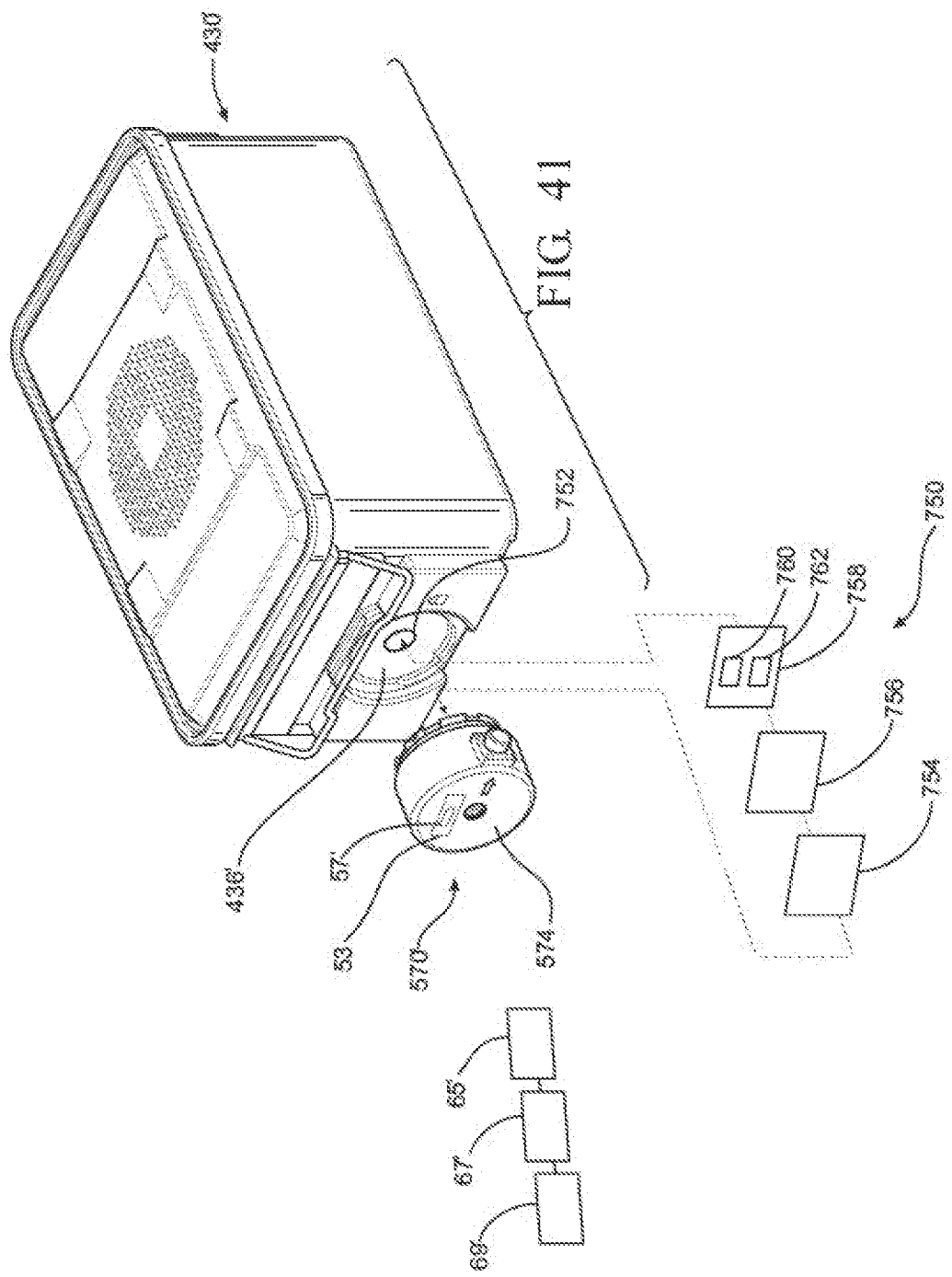

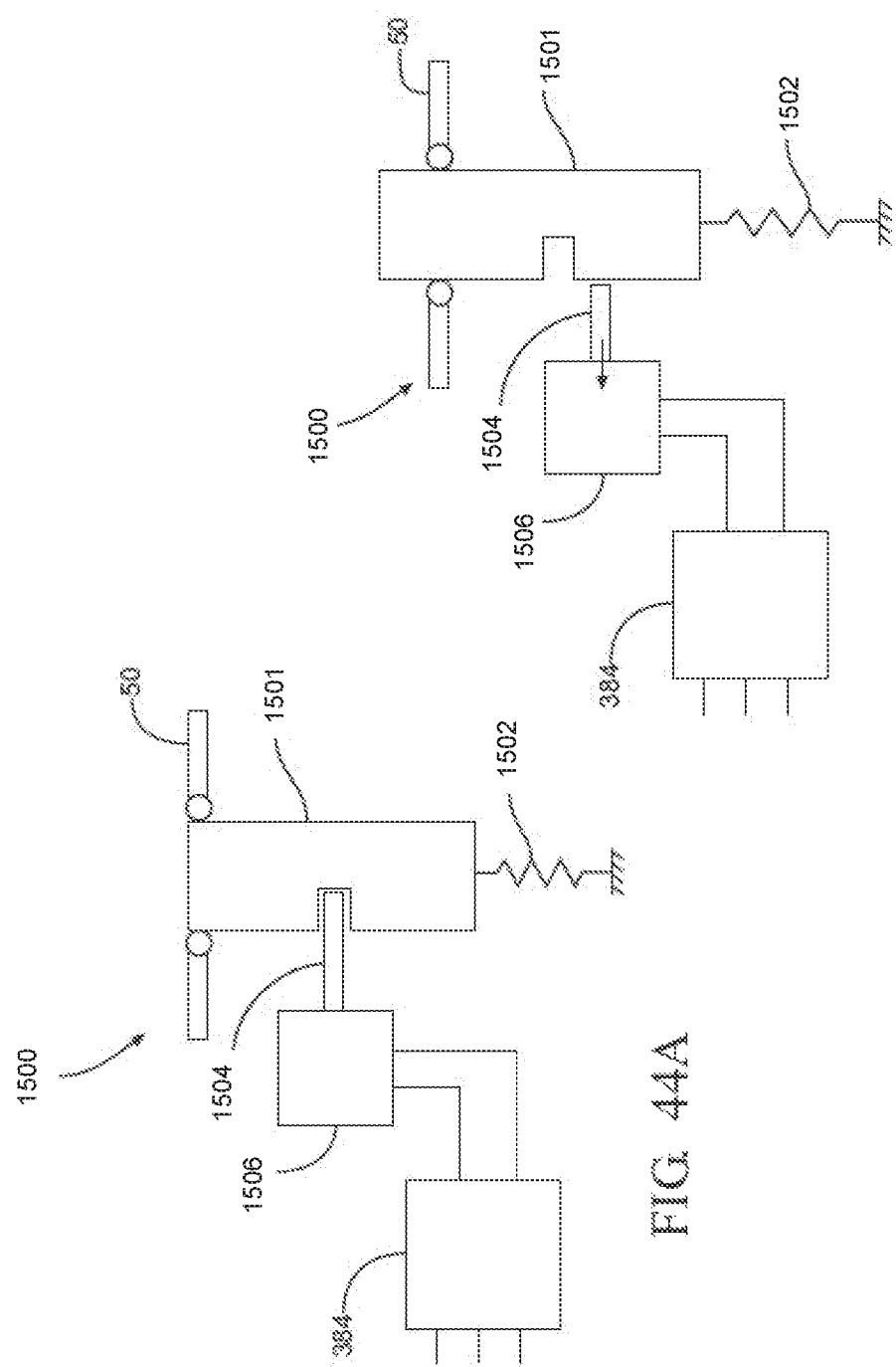

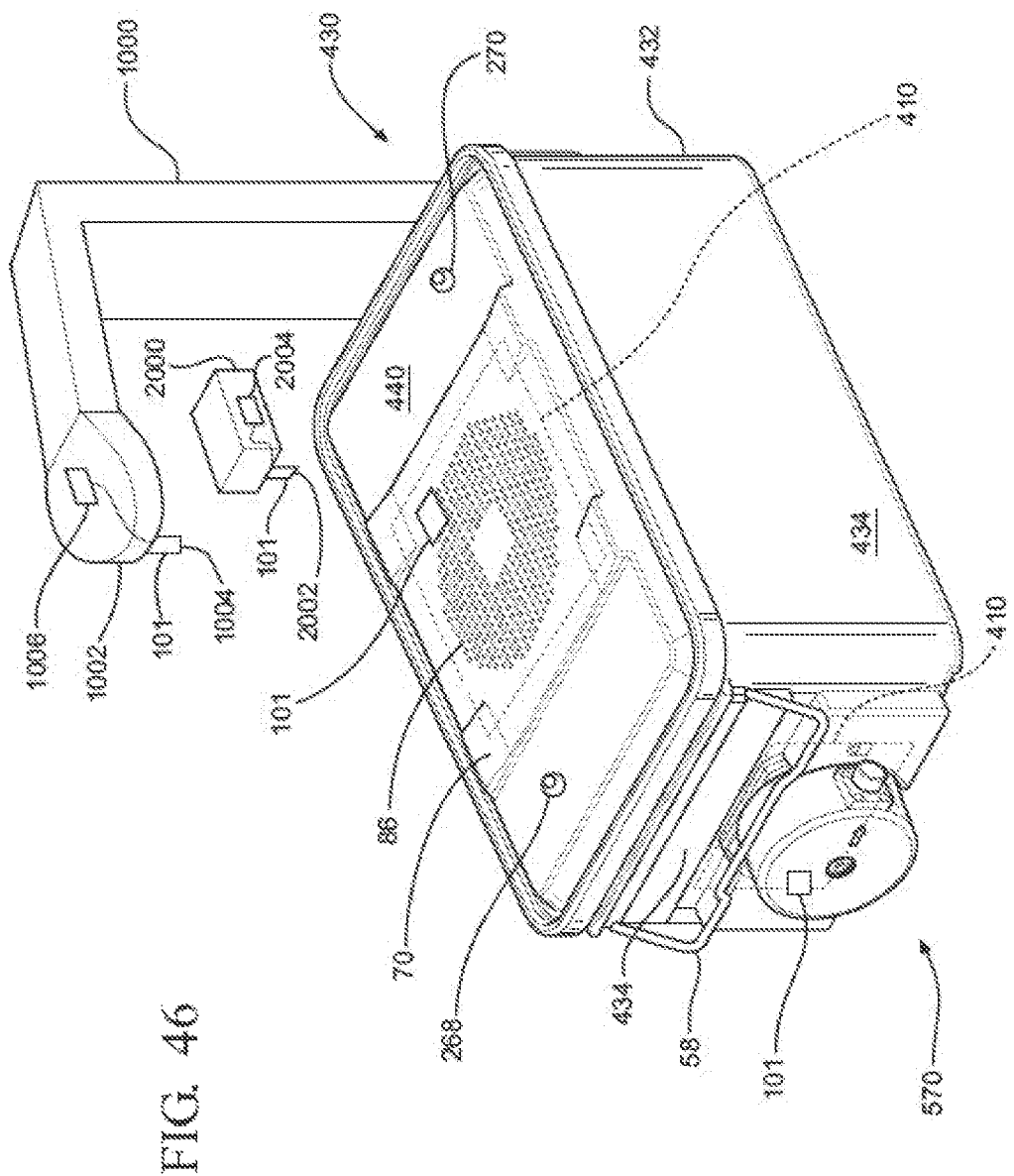

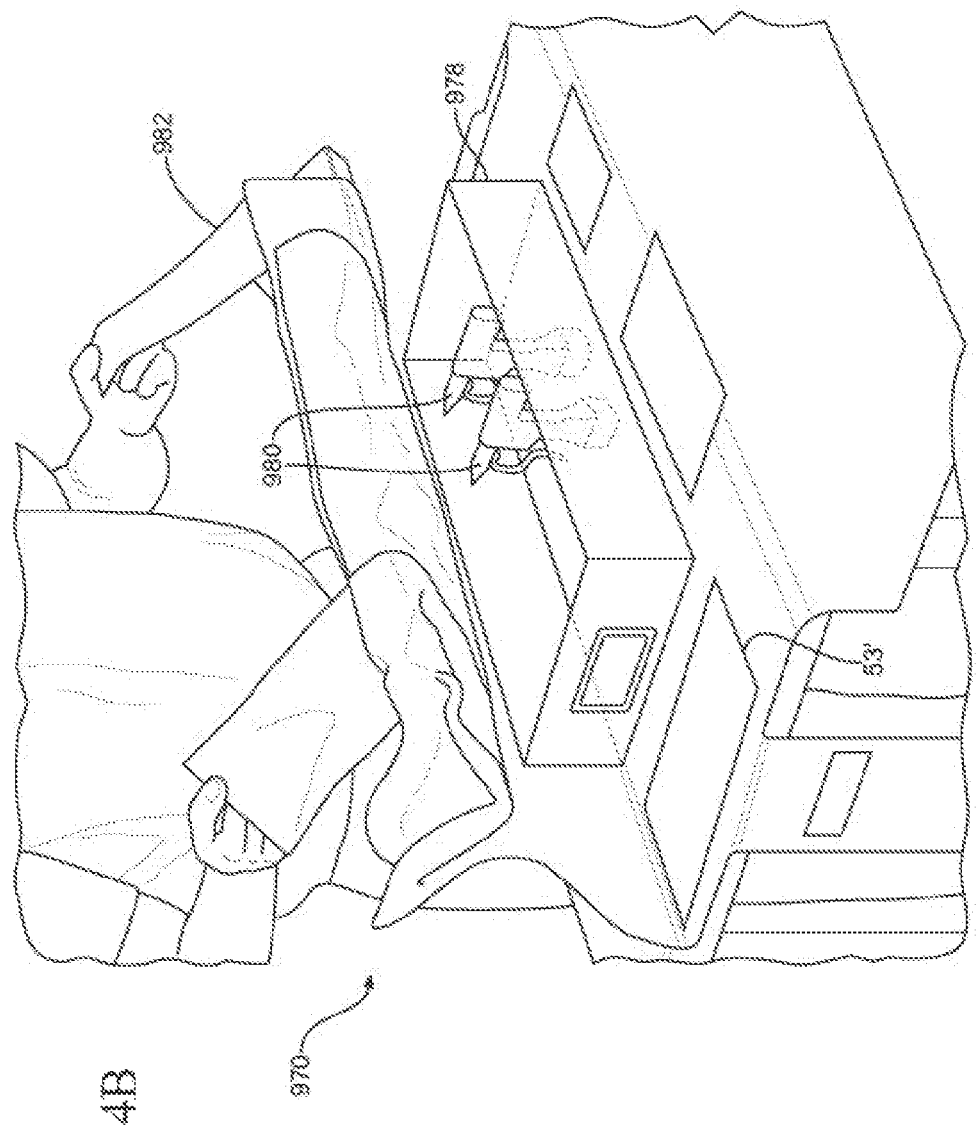

STERILIZATION ENCLOSURE FOR SURGICAL INSTRUMENTS

CROSS-REFERENCE TO RELATED APPLICATIONS

This application is a U.S. National Stage Application of International Patent Application No. PCT/US2016/051181, filed on Sep. 10, 2016, which claims the benefit of U.S. Provisional Patent Application No. 62/217,192, filed Sep. 11, 2015, and U.S. Provisional Patent Application No. 62/300,368, filed Feb. 26, 2016, all of which are hereby incorporated by reference in their entirety.

TECHNICAL FIELD

This disclosure is related to a sterilization enclosure configured to determine whether instruments disposed within the container have been exposed to threshold process conditions to ensure a desired level of sterilization for those instruments.

BACKGROUND OF THE DISCLOSURE

Medical device manufacturers continuously investigate sterilization systems that efficiently sterilize surgical instruments for use by Health Care Professionals (HCPs) during surgical procedures. Existing sterilization systems include containers configured to contain reusable surgical instruments during a sterilization process and sealingly store the sterilized instruments until they are required for a surgical procedure. The containers can comprise one or more apertures and filters configured to permit sterilant agent(s) to enter the container while preventing contaminants from entering the same. The sterilization systems can further include sterilizer devices, which can have a compartment for receiving one or more containers. The sterilizer device can be configured to supply the compartment with pressurized and/or heated sterilant agent(s), such that the sterilant agent(s) enter the containers through the apertures to destroy micro-organisms on the surgical instruments.

Containers can be disposed within the sterilizer device for periods of time that are empirically determined as threshold process conditions ensuring a desired level of sterilization for the corresponding instruments. In particular, the quantity of micro-organisms on instruments can be measured before and after a sterilization process, and if the sterilization process achieves a desired reduction of micro-organisms on the instruments, the measured characteristics of this process can be empirically determined as the threshold process conditions for ensuring the desired level of sterilization. Depending on the desired level of sterilization and the instruments being sterilized, periods of time ranging from 0.1 to 48 hours can be empirically determined as the threshold process conditions. The desired level of sterilization can be a 3-log reduction in micro-organisms on the surface of instruments, a 6-log reduction, or various other amounts, with the time of exposure being a threshold process condition that varies directly with the desired level of sterilization, such that longer times of exposure can be required to disinfect the instruments to higher levels of sterilization.

A drawback of these sterilization systems and the related sterilization process is that the instruments may not be properly disinfected to the desired level of sterilization, and the failure to achieve the desired level of sterilization may not be immediately noticed by HCPs. In particular, apertures of the container can be impeded or the filter can be occluded, such that the instruments inside the container may not be exposed to sterilant agent(s) and thus the instruments cannot be exposed to the threshold process conditions empirically determined to disinfect these instruments to the desired level of sterilization. Put another way, while the container may have been quarantined inside the compartment of the sterilizer device for the amount of time empirically determined to expose the instruments to threshold process conditions that would achieve the desired level of sterilization, the instruments may not have actually been exposed to sterilant agent(s) under the threshold process conditions to disinfect the instruments to the desired level of sterilization.

When the sterilization process has been completed, the sterilized containers remain sealingly closed and stored in a sterile inventory room until the instruments are required for a surgical procedure and the sealingly closed container is delivered to an operating room where the HCP opens the container, and retrieves the instruments for use during the surgical procedure. Existing containers may not have any sensors that measure the characteristics within the containers during the sterilization process, and the containers may not have notification devices that communicate to HCPs the non-sterilized status or sterilized status of the instruments. Thus, the hospital staff maintains records of the containers stored in the inventory room.

SUMMARY OF THE DISCLOSURE

A sterilization enclosure and associated methods are provided to determine whether instruments disposed within the enclosure have been exposed to threshold process conditions to ensure a desired level of sterilization for those instruments and/or to provide an indication and/or notification of the same.

BRIEF DESCRIPTION OF THE DRAWINGS

Referring now to the drawings, exemplary illustrations are shown in detail. Although the drawings represent examples, the drawings are not necessarily to scale and certain features may be exaggerated or schematic in form to better illustrate and explain a particular aspect of an illustrative example. Any one or more of these aspects can be used alone or in combination within one another. Further, the exemplary illustrations described herein are not intended to be exhaustive or otherwise limiting or restricting to the precise form and configuration shown in the drawings and disclosed in the following detailed description. Exemplary illustrations are described in detail by referring to the drawings as follows:

FIG. 3 is a perspective view of the inside of the lid of FIG. 1 and a sensor module coupled to a filter frame coupled to the lid;

FIG. 4 is an enlarged cross-sectional view of a portion of the lid of FIG. 1, showing the lid comprising a notification device;

FIG. 9 is an enlarged cross-sectional view of the sensor module of FIG. 3, illustrating the sensor module comprising a spring-loaded pin for detecting the presence of a filter;

FIG. 10A is an exploded view of the filter frame and the lid of FIG. 3, with the sensor module removed to depict components of the filter frame holding the filter medium against the lid;

FIG. 10B is a bottom view of the filter frame of FIG. 10A, showing the filter frame holding the sensor module and filter medium against the lid before a latch assembly is actuated to release the filter frame, sensor module, and filter medium from the lid;

FIG. 11 is a block diagram of the electrical components of the sensor module of FIG. 3;

FIGS. 12-14 are multiple cross-sectional views of the exemplary sensor module of FIG. 8, showing the sensor module comprising the collimator lenses immediately downstream of LEDs for using collimated light beams to measure light absorption of sterilant gases indicative of the concentration of the gases;

FIGS. 15-17 are multiple cross-sectional views of another exemplary sensor module, showing the sensor module encompassing the collimator lenses immediately upstream of photodetectors for using collimated light beams to measure light absorption of sterilant gases indicative of the concentration of those gases;

FIG. 19 is a schematic diagram of a portion of yet another exemplary sensor module, showing the sensor module comprising a spectrometer configured to measure light absorption by multiple sterilant gases indicative of the concentration of the gas;

FIG. 20 is a schematic diagram of a portion of still another exemplary sensor module, showing the sensor module comprising a FTIR spectrometer configured to measure light absorption by multiple sterilant gases indicative of the concentration of the gases;

FIG. 31 is a cross-sectional view of the block internal to the sensor module of FIG. 30;

FIG. 32A is a cross-sectional view of the sensor module of FIG. 30, illustrating the sensor module having a drain plug disposed in a lowermost position on the sensor module when the sensor module is mounted to the container, such that condensate flows away from the sensors and exits the sensor module through the drain plug;

FIGS. 34A and 34B are enlarged cross-sectional views of a portion of the valve of FIG. 23 when the valve is in the closed state;

FIGS. 35A and 35B are enlarged cross sectional views of a portion of the valve of FIG. 23 when the valve is in the open state;

FIG. 36A is an exploded view of a portion of another example of a sterilization container, illustrating a filter coupled to a normally closed valve that permits a sensor module to be aseptically and removably coupled to the container;

FIG. 37 is an exploded cross-sectional view of the sensor module of the container, the valve, and the filter of FIG. 36A;

FIG. 38B is a block diagram of another example of a sterilization container and sensor module that comprises a single temperature sensor coupled to the largest thermal mass within the container to measure the characteristics of the saturated steam to which the instruments are exposed;

FIG. 38C is a block diagram of still another example of a sterilization container and sensor module that comprises a single temperature sensor coupled to the largest thermal mass that is disposed outside of the container and within a sterilizer device to measure the characteristics of the saturated steam to which the instruments are exposed;

FIG. 39 is a perspective view of another example of a sterilization container, illustrating a sensor module comprising a non-electric sensor aseptically and removably coupled to an external surface of the container and a normally closed valve to fluidly communicate with the interior of the container;

FIG. 40 is an illustration of the sensor module used in FIG. 39;

FIG. 41 is a schematic diagram of a sterilization container comprising a trapdoor mechanism in replacement of the normally closed valve;

FIGS. 44A and 44B are schematic diagrams of one exemplary notification device having a button movable to a raised position to communicate that the instruments were exposed to the threshold process conditions for ensuring that the desired level of sterilization for the instruments has been achieved and a lowered position to communicate that the instruments were not exposed to the threshold process conditions;

FIG. 46 is an illustration of multiple filter detectors;

FIG. 54B is a perspective view illustrating wrapping of the sterile barrier wrap around the tray.

DETAILED DESCRIPTION

Figure 1:
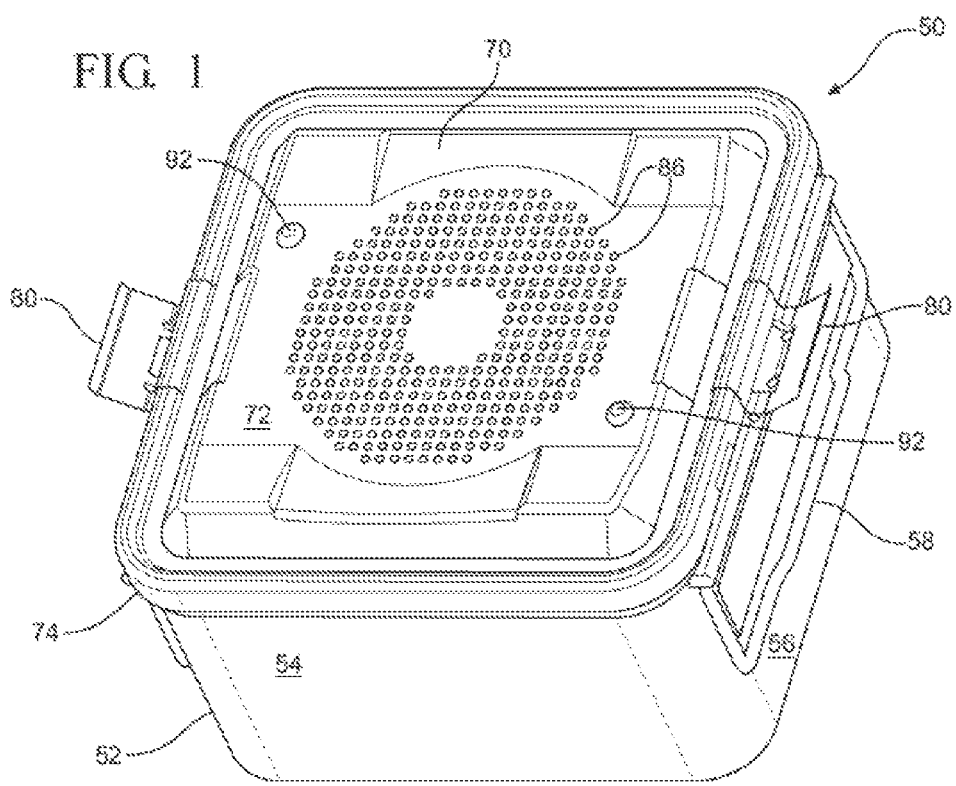
FIG. 1 is a perspective view of one non-limiting example of a sterilization container having a body and a lid coupled to the body.

An exemplary sterilization enclosure to be used for measuring characteristics within the enclosure during a sterilization process to determine whether surgical instruments disposed within the enclosure were exposed to threshold process conditions to ensure a desired level of sterilization for those instruments is described. The threshold process conditions can be customized or empirically determined based on the desired level of sterilization for a corresponding instrument using a look-up table or other suitable algorithm.

While the term "decontamination" refers to destruction of any amount of micro-organisms, sterilization is a specific level of decontamination that has been empirically determined as an acceptable level of destruction of microorganisms for certain applications. Examples of the acceptable sterilization process conditions can include a 3-log reduction in micro-organisms or 6-log reduction in microorganisms. However, the desired level of sterilization can be higher or lower than these exemplary reductions in microorganisms as necessary for particular applications. Thus, while the disclosure is directed to various devices, systems, and methods for a sterilization enclosure used to sterilize surgical instruments contained therein, it is contemplated that any number of these devices, systems, methods, or combinations thereof can be used in various other suitable applications where decontamination is required, such as an entire room for medical or non-medical applications. Non-limiting examples of non-medical applications requiring sterilization can include an ambulance, a manufacturing facility for computers, an aircraft, and a post office.

The phrase "surgical instrument" should be broadly understood, as used herein, to refer to any instrument or device used for medical treatment of any kind, including, but not limited to, patient care, diagnosis, therapy, or surgery.

The enclosure can comprise one or more sensors configured to measure the characteristics within the interior of the enclosure during a sterilization process. Furthermore, the enclosure can further comprise one or more notification devices for communicating the status of the instruments or the interior of the enclosure to a HCP. Further still, the notification devices may be configured for communicating the location of the enclosure to a HCP.

The sterilization enclosure should be broadly understood to encompass any structure or device that defines an interior configured to sealingly contain therein one or more instruments during a sterilization process and maintain a sterile barrier until the enclosure is opened, such as for retrieving the instruments within a sterile field of an operating room. In one embodiment, the term "enclosure" should be understood as device or apparatus capable of satisfying design and performance standards for sterilization containment devices, ANSI/AAMI ST77.

While some exemplary enclosures comprise containers having rigid bodies and lids coupled to the rigid bodies, other contemplated enclosures comprise a sterile barrier wrap arranged to sealingly encompass one or more instruments. The common characteristic of these enclosures are that they allow sterilant agent(s) into the enclosure during a sterilization or decontamination process to affect the reduction of microbial level on the instruments inside the enclosure and the enclosures maintain the reduced microbial level of the instrumentation after the enclosure is removed from the sterilizer. Still other enclosure configurations are contemplated. Furthermore, while the following exemplary sterilization enclosures comprise various components for measuring and/or comparing characteristics within the enclosure during the sterilization process and still various other components for indicating and/or communicating the status of the instruments and other components, it is contemplated that the enclosure can comprise any combination of these components, including any combination of the described sensors and notification devices. Exemplary enclosures will be described below. It should be appreciated that any features contemplated with respect to one enclosure may be combined with features described with respect to other enclosures.

Figure 2:
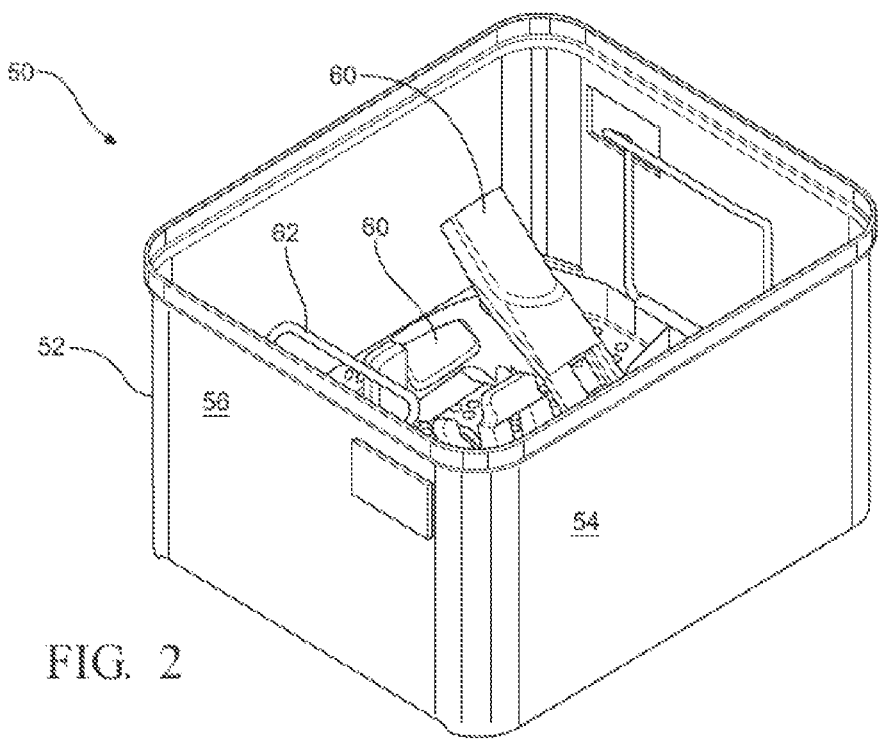
FIG. 2 is a perspective view of the body of FIG. 1 showing a surgical instrument disposed inside the body.

FIGS. 1-10E illustrate one exemplary sterilization enclosure in the form of a container 50. As shown in FIGS. 1 and 2, the container comprises a body 52 and a lid 70 removably attached to the body 52 for reusable medical device sterilization. However, it is contemplated that the enclosure can include other forms. In this example, the body 52, the lid 70, and various components attached to the lid, as described below, are formed from material that can be placed in a sterilizer device and withstand exposure to sterilant agent(s) used to decontaminate surgical instruments to a desired level of sterilization, such as stainless steel or aluminum. In the illustrated embodiment, the body 52 is formed from a number of panels that are arranged together to give the body a generally rectangular shape. Of course, it is contemplated that the configuration of the body 52 is not particularly limited. A front panel 54 and a side panel 56 are identified in FIG. 2. Not seen are the back panel opposite the front panel 54 and the second side panel opposite the illustrated side panel 56. Also not seen is the bottom panel that extends between the front, back, and side panels. The bottom panel, it is understood, provides the body 52 with a closed bottom end. The top of the body 52 is open. A handle 58, one seen in FIG. 1, is pivotally mounted to the outside of each of the side panels 56. The body 52 may be shaped to hold one or more surgical instruments 60. The instruments 60 may be seated on a rack 62 that is removably seated in the body 52.

The lid 70 may be removably attached to the body 52 so as to cover the open top end of the body 52. The lid 70, as seen in FIGS. 1, 4, and 10A, includes a plate 72 that forms the main body of the lid 70. The plate 72 is configured to extend over essentially the whole of the open end of container body 52. A rim 74 extends around the outer perimeter of lid plate 72. The rim 74 defines a groove 76, and a compressible seal 78, a section of which is seen in FIG. 10A, is seated in the groove 76. The components forming container 50 are formed so that when the lid 70 is seated over the body 52, the top edges of the body, front, back, and side panels are received within the groove 76 so as to abut seal 78.

A latch 80 is mounted to the opposed sides of rim 74. The latches 80, when set, releasably hold the lid 70 to the body 52. The latches 80 are further designed so that when in the latched state, the latches 80 urge the lid 70 against the body 52. This results in the seal 78 being compressed between the top edges of the body 52 and the lid rim 74. As a result of this compression of the seal 78, the seal forms an airtight barrier between the body 52 and the lid 70. The seal 78, when compressed, is sufficient to prevent ingress of contaminants that would compromise the sterilization condition of the contents within the interior of the sterilization container.

In certain embodiments, a post 82, seen in FIG. 10A, may extend inwardly from the body 52 facing surface of lid plate 72. The post 82 is formed with a groove 83 that extends annularly around the post. In the illustrated example, the post 82 is centered on the center of the plate 72.

The front panel 54, the side panel 56, the floor 57, the lid plate 72, or any combination thereof includes an aperture permitting sterilant gas to flow from the sterilizer into the interior of the container. Of course, any numbers of apertures are contemplated, and these apertures may be located in any suitable location on the container. In this example, the floor 57 and the lid plate 72 includes a number of apertures 86, two identified in FIG. 1. In one exemplary configuration, apertures 86 are arranged in a circular pattern around post 82. The apertures are also spaced radially outwardly from the post 82. Of course, other patterns of apertures are also contemplated.

In enclosures that comprise the sterile barrier wrap, the wrap is generally a porous material that allows ingress of the sterilant gas, but does not allow ingress of contaminants. The pores in the wrap may be considered as one example of apertures with characteristics similar to filter medium 410 as described below.

In the illustrated embodiment, the lid plate 72 is further formed to have two openings 88, one seen in FIG. 4. Openings 88 are diametrically opposed to each other relative the post 82. A transparent dome 92 is mounted in each opening 88. The dome 92 can be comprised of a single piece of sterilizable material such as a polyphenylsulfone plastic. One such plastic is sold under the brand name RADEL by Solvay Advanced Polymers, of Alpharetta, Ga., United States. Referring to FIG. 4, the dome 92 is shaped to have a cylindrical stem 94. Stem 94 is the portion of the dome that is seated in opening 88. A head 95 is formed integrally with and extends above the stem. Head 95 has a diameter greater than that of the opening 88 in which the dome 92 is seated. A retainer/seal 96 is disposed around the portion of the stem 94 that projects inwardly from the underside portion the lid plate 72. Here the "underside surface" of the lid plate 72 is understood to mean the surface of the plate facing the interior of the body 52. The "topside" surface is understood to mean the outwardly directed surface of the plate. Seal 96 forms a gastight barrier between the lid plate 72 and the portion of the stem 94 seated in the opening 88.

From FIGS. 3 and 10A-10E it can be seen that a sensor module 102 and a filter frame 320 may be positioned adjacent to the aperture through which sterilant gases ingress into the interior of the container. In this example, the sensor module 102 may be coupled to the filter frame 320, which in turn is coupled to the underside portion of the lid plate 72 that defines the apertures 86 through which sterilant gases ingress into the interior of the container. Put another way, the sensor module 102 may be coupled to the filter frame 320 in any suitable manner such that the position of the sensor module 102 is selectively fixed relative to the filter frame 320. This configuration permits the sensor module to be used for any suitable sterilization container configuration, because even sterilization containers, which were not originally designed to include a sensor module, can have a filter frame that can be retrofitted with the sensor module. Additionally, by coupling the sensor module to the filter frame, where the filter frame is positioned adjacent to the apertures in the sterilization container, the sensor module is adjacent to the volume of sterilant agent(s) that enters the interior of the sterilization container. By monitoring the characteristics of sterilant agent(s) immediately adjacent to, or passing through, the filter medium, the sensor module advantageously can sense the changes through a control surface surrounding the interior of the sterilization container. Of course, it should be appreciated that, through coupling of the sensor module 102 to the filter frame 320, characteristics of other portions of the sterilant agent(s) can be monitored, such as volumes of sterilant agent(s) which are not adjacent to the filter medium and/or apertures of the filter container.

In other embodiments, the filter frame may be coupled to the sensor module, which is in turn coupled to the portion of the container defining the apertures. In still other embodiments, each one of the sensor module and the filter module may be independently and directly coupled to the portion of the container defining the apertures or various other portions of the container.

The filter frame 320 is configured to retain and press a filter medium 410 in the interior of the container and against the front panel 54, the side panel 56, the floor 57, the lid plate 72 of the container, or any combination thereof adjacent to apertures 86 formed in the same. As one example, the filter frame 320 holds the filter medium 410 against the underside surface of the lid plate 72 so the filter medium 410 extends under and radially outwardly from the apertures. The filter medium 410 is comprised of material that is permeable to sterilant agent(s), which are in a gaseous state and are employed to sterilize the instruments 60 disposed in the container and is sufficiently impermeable to contaminants to maintain sterility within the interior of the sterilization container. The filter medium 410 may be dimensioned to cover the apertures 86 in the lid 70. Furthermore, the filter medium 410 may comprise a center hole 412 positioned so that when the filter medium 410 is disposed against the inner surface of the lid plate 72, the post 82 may extend through the center hole 412. It should be appreciated that the sterilization container may include multiple filter frames, such that filter mediums may be positioned adjacent to any apertures included within the sterilization container.

Continuing with the example shown in FIGS. 3 through 7, the sensor module 102 may be configured to be coupled to the filter frame and retain one or more sensors configured to sense the characteristics of the sterilant agent(s) entering through the filter or residing within the interior of the sterilization container. In particular, the sensor module 102 can include a housing, which in this example comprises a base 104 and a shell 152. The base 104 may be generally plate-like in shape and formed to define a through-opening 106. In the illustrated example, through-opening 106 subtends an area that is greater than 50% of an area within the perimeter of the base 104. The sensor module 102 is further constructed so that opening 106 allows the flow of sterilant through the filter frame 320. A ring 107 is formed integrally with and extends upwardly from the inner-directed surface of the base 104. The ring 107 extends upwardly from the inner edge of the base 104 that defines the outer perimeter of opening 106. A lip 108, seen best in FIG. 4, protrudes radially outwardly from and extends circumferentially around the free end of ring 107. A rim 109 extends upwardly from the top-facing surface of the lip 108. In the illustrated example, the inner circular surface of rim 109 is located radially outwardly from the outer surface of the ring 107. The outer circular surface of the rim 109 is located inwardly from the outer radial surface of the lip 108.

Figure 7:
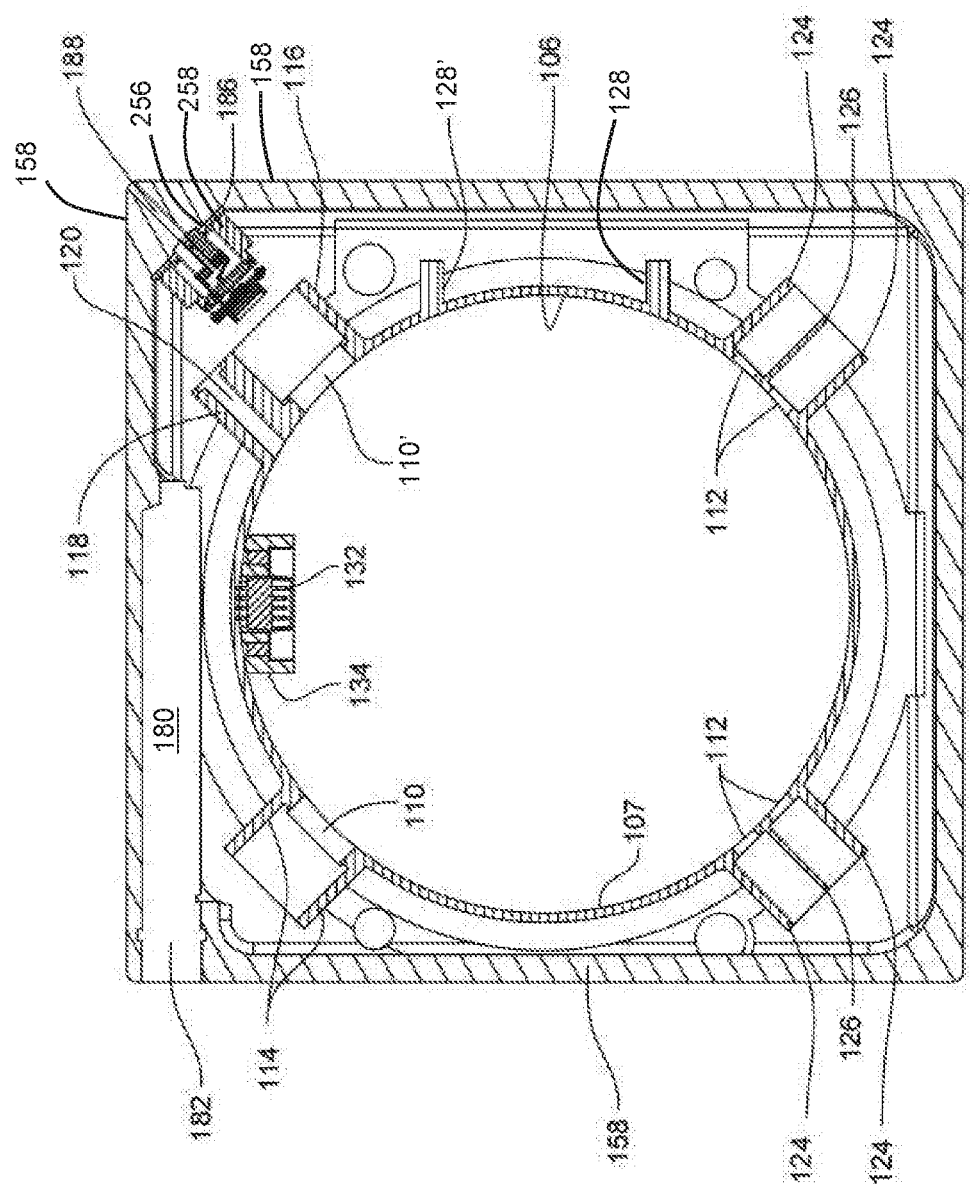
FIG. 7 is a cross-sectional view of the inside of the base and shell of the sensor module of FIG. 3.

Referring to FIG. 7, the ring 107 is formed to have a number of openings 110. There are two openings 110, 110'. Openings 110, 110' are spaced 90° apart from each other in the ring 107. There are two pairs of openings 112. Each pair of openings 112 is located in the ring 107 so that the section of the ring 107 that separates the individual openings in a pair of openings 112 is 180° from the center of the openings 110, 110'. Each of the openings 112 is smaller in diameter than the openings 110, 110'.

A number of planar webs extend radially outwardly from the inner face of the ring 107, the face of the ring opposite the face of the ring that defines the perimeter of opening 106. Two essentially identical parallel webs 114 extend outwardly from the section of the ring 107 that defines one of the openings 110. Each web 114 is spaced arcuately away from the adjacent opening 110. A web 116 and a web 118 extend away from the inner face of the ring face adjacent the opening 110'. Webs 116 and 118 are parallel with each other. Each web 116 and 118 is spaced arcuately away from the associated opening 110'. Web 116 is essentially identical in shape to the web 114. Web 118 has a larger cross-sectional width than the associated web 116. Here the cross-sectional width is understood to be the wall thickness of the corresponding webs. In other words, the web 118 has a wall thickness that is greater than a wall thickness of the web 116. The components forming the module housing are further formed so that a bore 120 extends longitudinally through web 118. One end of bore 120 opens into the inner face of the ring 116. Thus, bore 120 opens into the inner surface of the ring 107. Bore 120 extends radially outwardly from the ring 107 to the end of the web 118 that is radially spaced from the ring.

Two parallel webs 124 extend outwardly from the ring around each pair of openings 112. The webs 124 associated with each pair of openings 112 are located arcuately away from the opposed sides of the openings 112 with which the webs are associated. The webs 124 are arcuately spaced away from the adjacent openings 112. A web 126 is located between and is parallel with each pair of openings 112. Each web 126 extends outwardly from the section of the inner face of the ring between the openings 112 with which the web is associated.

Two additional webs 128, 128' extend outwardly from the inner face of ring 107. One web 128 is arcuately adjacent web 116. The second web 128 is adjacent the web 124 closest to web 116. Webs 128 are parallel to each other.

In the illustrated example, a terminal 132 is shown mounted to ring 107 so as to extend into opening 106. Terminal 132 has a number of contacts (not identified). The terminal 132 is surrounded by an open-ended cage 134. Cage 134 extends outwardly from the outer face of the ring 107 into the opening 106.

In the illustrated example, indicia 138 are shown in FIG. 3 formed into the outer face of the base 104. The indicia 138 include the text "LATCH" and an accompanying arrow.

Figure 6:
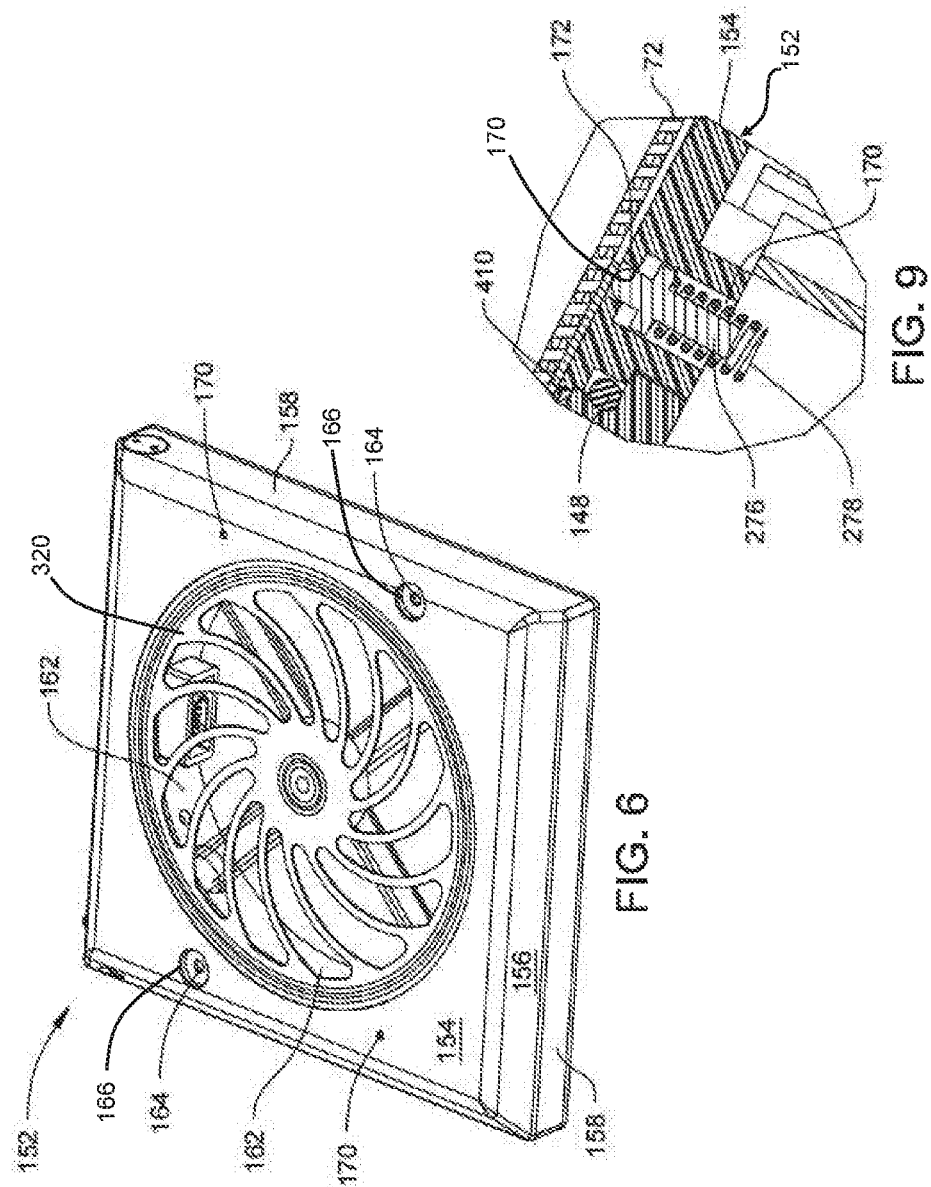
FIG. 6 is a top perspective view of the sensor module of FIG. 3, illustrating the sensor module having a shell that is coupled to the filter frame.

Shell 152, as seen best in FIGS. 6 and 7, includes a top panel 154. In the illustrated example, the top panel 154 has a shape that generally matches the shape of base 104, though the top panel 154 occupies a slightly smaller surface area. Transition panels 156 extend downwardly and outwardly from the top panel 154. Side panels 158 (two identified) extend downwardly from the transition panels 156. The side panels 158 are perpendicular to the top panel 154. Collectively, the base 104 and shell 152 are shaped so that the outer perimeter of the shell 152, as defined by the side panels 158, matches the outer perimeter of the sensor module 102.

The shell 152 is further formed so there is a circular center opening 162 in the top panel 154. Circular opening 162 is positioned so that when the module 102 is assembled the circular opening 162 is concentric, with the base opening 106. The shell 152 is further formed to define an outer lip 165 and an inner lip 167 both seen best in FIG. 4. Both lips 165 and 167 have exposed faces that are planar with the top surface of the shell top panel 154. Outer lip 165 has a top to bottom thickness less than that of the adjacent section of the shell top panel 154. The inner lip 167 is located radially inward from the outer lip 165. Inner lip 167 has a top to bottom thickness less than that of the outer lip. The inner perimeter of inner lip 167 defines the outer perimeter of opening 162.

The components forming the sensor module are further constructed so that when the shell 152 is secured to the base 104, the lip 108 integral with ring 107 seats in the space below the outer lip 165 and rim 109 is located slightly inwardly from the outer lip 165. An O-ring 148, identified in FIGS. 4 and 9, is seated between the lip 108 integral with ring 107 and outer lip 165 integral with the shell top panel 154. During the process of assembling the sensor module 102, the O-ring 148 is compressed between the lips 108 and 165. The O-ring 148 thus provides a seal between ring 107 and the shell top panel 154.

Shell 152 is further formed to have two bores 164 open into the top panel. Bores 164 are diametrically and symmetrically opposed to each other relative to the center of opening 162. In the exposed face of top panel 154, each bore 164 is surrounded by a counterbore 166. When the sensor module 102 is mounted to the container lid 70, each shell bore is disposed under one of the domes 92 mounted to the lid. The components are dimensioned so that each counterbore 166 in the shell can receive the stem 94 integral with the overlying dome 92.

Referring to FIG. 6, the two additional openings in the shell top panel 154 are bores 170, which are spaced radially away from opening 162. Bores 170 are diametrically opposed from each other. Bores 170 are further positioned at a location such that, when the filter medium 410 is disposed above the sensor module 102, the filter medium 410 extends over the bores 170. As shown in FIG. 9, the shell 152 further comprises a lip 172 projecting from the shell top panel 154 that forms each one of the bores 170. While this exemplary shell 152 comprises two bores 170 that are identical to one another in their structural configurations, only one of the bores 170 is illustrated in FIG. 9.

Figure 5:
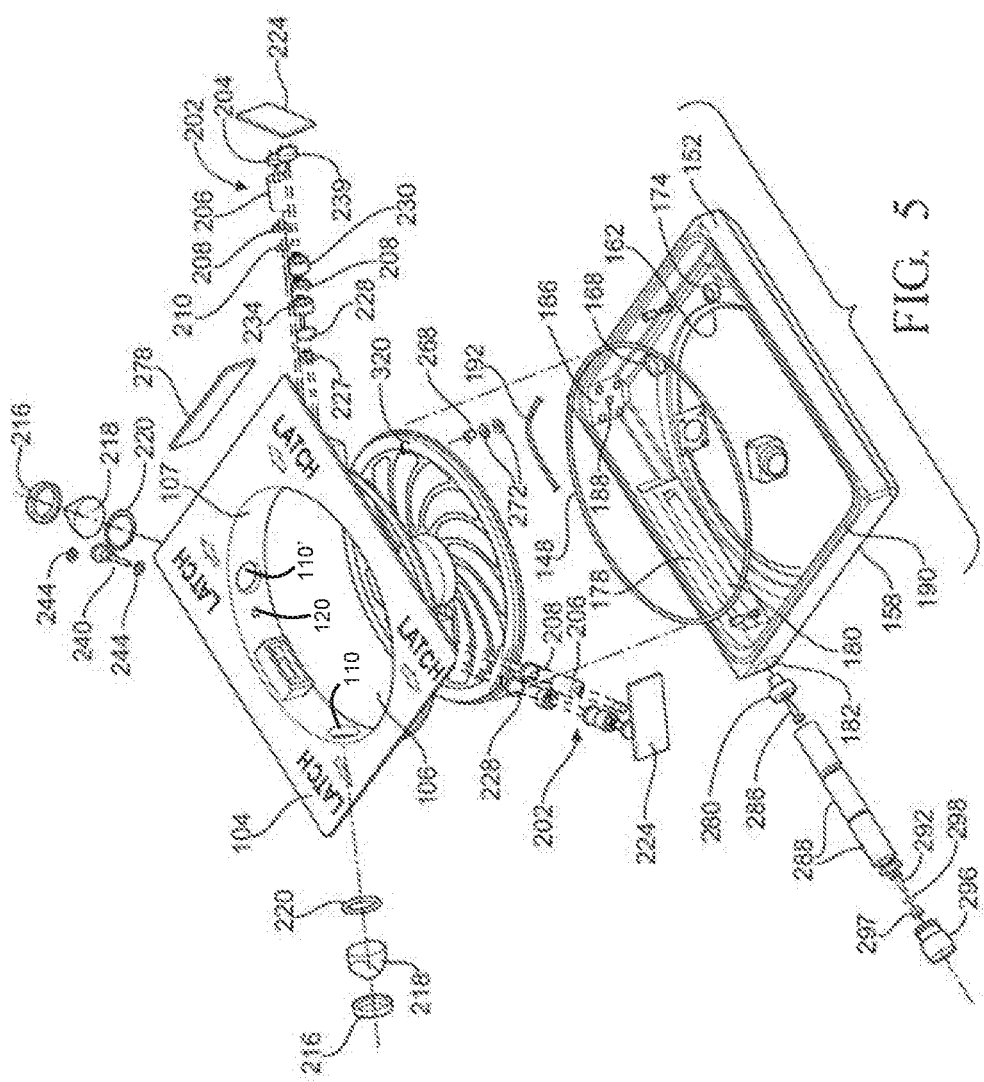
FIG. 5 is an exploded view of the sensor module of FIG. 3.

A sleeve-like boss 168, one boss seen in FIG. 5, surrounds each bore 164 and extends outwardly from the inner face of top panel 154. A sleeve-like boss 174, one boss seen in FIG. 5, surrounds each bore 170 and extends outwardly from the inner surface of top panel 154. Bosses 168 and 174 provide support for the components seated in bores 164 and 170, respectively.

Referring to FIG. 5, shell 152 is further formed so that a sleeve 178 is formed integrally with one of the side panels 158 and extends inwardly from the panel with which the sleeve is associated. In planes perpendicular to the major axis through the sleeve 178, the sleeve is rectangular in shape. Sleeve 178 is formed to define a closed-ended chamber 180 that extends axially through the sleeve 178. The side panel 158 closest to the sleeve 178 is formed with a bore 182. Bore 182 opens into chamber 180. While not seen, the interior surface of the shell 152 that defines bore 182 may be formed with threading.

The exemplary sensor module 102 can further comprise a set of series-aligned cells 288 mounted in chamber 180. The cells 288 provide power to the components internal to the module that require electrical current to function. The sensor module 102 can further comprise an insulator 280 disposed adjacent to the closed end of the sleeve chamber 180. Furthermore, the contact 286 can abut the positive terminal of the lead cell 288, and the contact 292 can abut the negative terminal of the tail cell. The sensor module 102 can further comprise a plug 296 configured to hold the cells 288 in chamber 180. The plug 296 can comprise an outer surface with a threading, such that the plug 296 can be removably secured in a threaded bore 182. The sensor module 102 can further comprise a spring 297 located between the tail cell 288 and the plug 296 to urge the cells 288 against the contact 286 adjacent insulator 280. An O-ring 298 can be disposed around plug 296. The components forming sensor module 102 are arranged so that the O-ring 298 provides a seal between the plug 296 and the surface of the shell that defines bore 182.

The shell 152 is further formed so a triangular block 186 extends inwardly from the corner where two of the side panels 158 meet. In the illustrated example, the corner from which the block 186 extends is the corner adjacent the end of sleeve 178 that is spaced from bore 182. An elongated bore 188 is formed in block 186. Bore 188 extends radially inwardly from planar inner face of the block 186. Bore 188 opens in the outer surface of the corner between the side panels 158 with which the block is associated (see FIG. 7).

The shell side panels 158 comprise a groove 190 that extends inwardly from the free ends of the panel. Groove 190 extends circumferentially around the shell 152 immediately inwardly of the outer perimeter of the shell. A gasket 192 a portion of which is seen in FIG. 5, is disposed in the groove 190. The gasket 192 extends a short distance outwardly away from the shell 152. When the base 104 is secured to the shell 152, the gasket 192 is compressed between the base 104 and the side panels 158 of the shell 152. Gasket 192 thus provides a seal between the base 104 and the side panels 158.

Not illustrated are the fasteners that hold the module base 104 to the shell 152. These fasteners extend through openings in the base into closed-ended bores internal to the shell side panels, base openings, and shell bores not illustrated. As a result of these fasteners holding the base to the shell, O-ring 148 is compressed between the ring 107 integral with the base 104 and the shell top panel 154. Gasket 192 is compressed between the base 104 and the shell side panels 158.

It should be appreciated that other sensor module configurations are contemplated for use in conjunction with the filter frame, so long as they are operable to be coupled to the filter frame and retain a sensor that is configured to sense the characteristics of the sterilant agent(s) passing through the filter or the characteristics of the interior of the sterilization container or enclosure.

As best shown in FIG. 10A, the illustrated filter frame 320 includes a centrally-located hub 322. A rim 332 extends circumferentially around and is radially spaced away from the hub 322. Plural flexible, spring-like webs 330 extend between the hub 322 and the rim 332 so as to connect the hub and rim together. The hub is formed to have a center opening 328. The hub 322 has a ring 324 that extends downwardly from the inwardly directed surface of the hub. Ring 324 defines the perimeter of the opening 328. The filter frame 320 may assume other configurations suitable to compress the filter adjacent the apertures of the lid plate. For example, the filter frame may assume any suitable shape and dimension so long as the filter frame is capable of biasing the filter media adjacent to the apertures so that a seal is formed by the filter frame.

In certain embodiments, the filter frame is further formed so that the rim 332 is formed with an upwardly facing groove 334, seen in FIG. 4. A small lip 336, identified in FIG. 10A, projects radially outwardly from the portion of the rim 332 that defines the groove 334. When the sensor module 102 is assembled, the filter frame lip 336 is sandwiched between the rim 109 associated with ring 107 and the inner lip 167 integral with the shell 152. The sandwiching of the lip 336 between the ring 107 and the shell 152 holds the filter frame 320 to the rest of the module 102.

Of course, as mentioned above, other configurations of the filter frame and sensor module are contemplated which would be suitable to retain the position of the filter frame relative to the sensor module. In other words, the sensor module may comprise a filter frame attachment device that is suitable to couple the sensor module to the filter frame. In the illustrated embodiment, the filter frame attachment device comprises the ring 107 and the inner lip 167, but other structure is contemplated. For example, the filter frame attachment device may comprise one or more fasteners, an adhesive, or one or more magnets.

Still referring to FIG. 10A, a latch assembly 338 releasably holds the filter frame 320 to the underside of the lid plate 72. The latch assembly 338 includes a cap 342 that is mounted to the frame hub 322. Cap 342 is disposed over ring 324. Two slides 344 are moveably mounted in the cap 342. The slides 344 are formed with features, not identified, that are arranged to seat in the groove formed in the post 82 so as to hold the filter frame and, by extension, the whole of the sensor module 102 to the lid 70. Springs 346 hold the slides 344 in the cap 342 so the slides are normally in a position to engage the lid post 82. While not illustrated, one end of each spring 346 is connected to a first one of the slides 344. The opposed end of each spring 346 is connected to the second slide 344.

The slides 344 extend out of opposed openings 348 in the cap (one opening 348 shown in FIG. 10A). Finger-force that is applied against the slides 344 displaces the slides from the locked state to the release state. When the slides are in the release state, the slides do not engage post 82. This allows for the removal of the sensor module 102 from the lid 70. Of course, other configurations of the latch assembly are contemplated.

A rigid disc 352 is disposed over the inner-directed face of the cap 342. A circular seal 354 formed from elastomeric material is disposed over the outer face of disc 352. A gasket 356, which is also formed from elastomeric, compressible material, is seated in the groove 334 internal to the frame rim 332. The components forming the filter frame 320 are arranged so that when the filter frame 320 is latched to the lid 70, seal 354 and gasket 356 press against the filter medium 410. Consequently, when container 50 is in this state, the center of the filter is compressed between the lid 70 and seal 354. The perimeter of the filter is compressed between the lid 70 and gasket 356.

One or more sensors can cooperate with the container to measure characteristics within the interior of the container during a sterilization process. The sensor module 102 described above may include a sensor configured to measure the sterilant gas and other vapors or gases entering and exiting the container through filter medium 410. For other containers which may have additional locations for sterilant gas to enter and exit through filter medium 410, multiple sensors suitably located can work in combination with one another to measure all sterilant agent(s) and other vapors or gases entering and exiting the container to effect decontamination of the instruments inside of the container. These sensors can be disposed within the interior of the container and/or coupled to an external surface of the container 50. In a further embodiment, the sensor may form part of the container/enclosure. More specifically, one or more of these sensors can comprise one or more stand-alone devices and/or one or more integral components of a sensor module that are: (1) disposed within the container; (2) coupled to an external surface of the container but in fluid communication with the interior of the container; and/or (3) communicate with an airflow challenge cannula, which in turn communicates with the interior of the container described herein.

Furthermore, the sensors can comprise any suitable configuration to measure different characteristics within the container during the sterilization process, and these characteristics can individually or collectively ensure that the desired level of sterilization for the instruments has been achieved. Examples of these configurations can include: (1) one or more optical sensor assemblies; (2) one or more gas concentration sensors; (3) one or more temperature sensors; (4) one or more pressure sensors; (5) one or more sound sensors; and/or (6) one or more electromagnetic wave transmission sensors. These sensors can be used individually or collectively to measure the corresponding characteristics of sterilant gas concentration, temperature, and/or pressure within the container during the sterilization process.

Multiple sensors may be provided that are integral components of sensor module 102. In this example, the sensors comprise: (1) one or more gas concentration sensors, (2) one or more temperature sensors, and (3) one or more pressure sensors, which collectively detect the concentrations of sterilant gases, the temperature, and the pressure within the container during the sterilization process. One or more of these sensors can be configured to generate a signal indicative of the measurement taken and communicate the same to a processor by wireless or wired transmission. While exemplary configurations of these sensors are described below, other configurations of these sensors and/or any other suitable sensors can be used to measure the characteristics within the container during the sterilization process.

In one specific embodiment, the sensor module 102 may include a gas concentration sensor, such as an optical sensor assembly configured to measure the absorption of light by the sterilant gas indicative of the concentration of the sterilant gas within the interior of the container and/or within the sterilizer device having the container disposed therein. A processor can compare the measured light absorption with the threshold process conditions empirically determined to ensure the desired level of sterilization. To detect the concentrations of multiple sterilant gases within the interior of the container and/or the sterilizer device, two or more optical sensor assemblies configured to measure the concentrations of corresponding gases can be used. While the sensor module can comprise two optical sensor assemblies, any number of optical sensor assemblies can measure the concentrations of sterilant gases. In other embodiments, the gas concentration sensor may comprise a catalytic sensor, an electrochemical sensor, an infrared sensor, a semi-conductor sensor, and combinations thereof.

Referring to FIGS. 11-14, the sensor module 102 includes two optical sensor assemblies 202 configured to determine a gas concentration within the interior of the sterilization container. In one embodiment, the optical sensor assemblies 202 are configured to measure the absorption of light indicative of the concentrations of a corresponding one of two sterilant gases within the container 50, such as water vapor and hydrogen peroxide. However, the optical sensor assemblies 202 can be configured to measure the absorption of light indicative of the concentration of any suitable sterilant gas. In this example, each optical sensor assembly 202 is configured to emit a beam of light at a wavelength through a sample of the sterilant gas within the container 50. The amount of light that is absorbed by the corresponding sample of sterilant gas is indicative of the concentration of that sterilant gas within that sample.

Each one of the optical sensor assemblies 202 is configured to measure the light absorption by a sample of the sterilant gas along one or more light paths within the container 50. The amount of light absorbed by the sterilant gas is indicative of the concentration of the sterilant gas. The accumulated length of the light paths directly correlates with the amount of sterilant gas exposed to the light and thus the accuracy in measuring light absorption and the corresponding concentration of sterilant gas.

If the concentration of gas reaches a predetermined threshold condition, it can be determined that the desired level of sterilization for the instruments was achieved. In an alternate example, a processor can be used to determine the curve defining the concentration of sterilant gas over time. The processor can calculate the area under the curve over a period of time and compare the area with corresponding threshold process conditions in a lookup table empirically determined to ensure a desired level of sterilization for the instruments, as described in U.S. Patent Application Pub. No. 2015/0374868, the disclosure of which is hereby incorporated by reference herein.

In one specific embodiment, each one of the optical sensor assemblies 202 can include a light source configured to emit light across the opening 106 of the sensor module 102. More specifically, the light source can be an LED 204 configured to emit light at one or more predetermined wavelengths. In one example, the LED 204 emits white light. The LED 204 is disposed between one of the webs 124 and the arcuately adjacent web 126. Each LED 204 is contained in a sleeve 206 that is configured to hold LED 204 between the webs 124, 126. The LED 204 is positioned so that the LED 204 emits light through the ring opening 112 located immediately inward of the webs 124 and 126. Alternative light sources other than LEDs may be used.

Figure 17:
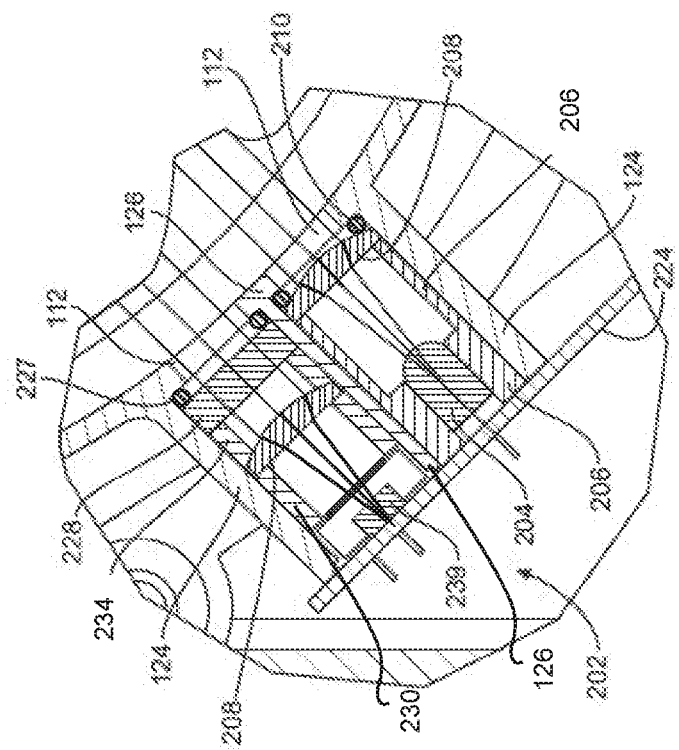
Figure 14:
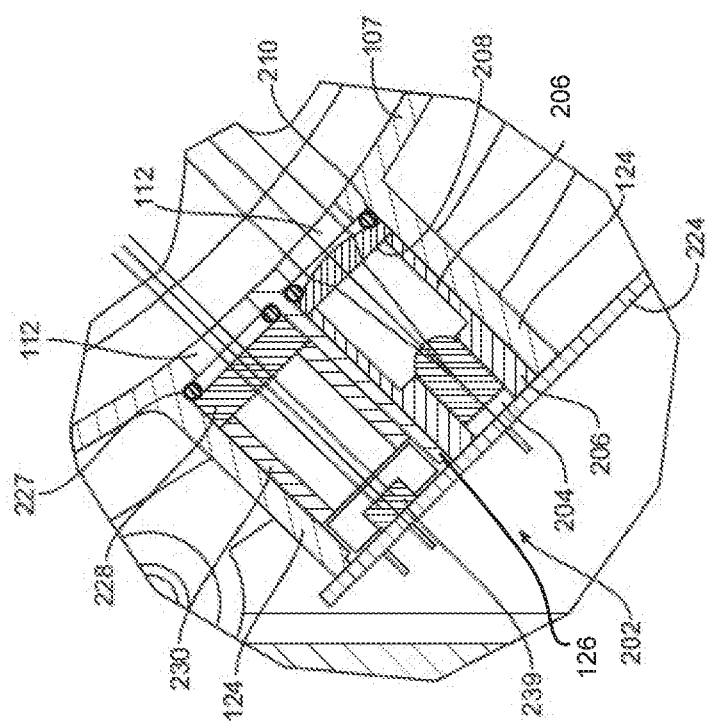

Each one of the optical sensor assemblies 202 may further comprise a collimator lens 208, which is configured to collimate, concentrate, or narrow the light beam and direct the same through the corresponding opening 112. The beam of light, emitted by the LED, optionally in a collimated state, can be detected by a photodetector 239, which may be comparably smaller and thus less expensive than a photodetector configured to detect a non-collimated beam of light. Additionally, another benefit of the more compact photodetector is that it can be attached to portions of the container 50 that cannot have comparably larger photodetectors coupled thereto. While the collimator lens 208 is disposed immediately downstream of the LED 204 as shown in FIG. 14, another exemplary sensor module, as shown in FIG. 15-17, may comprise a collimator lens 208 disposed immediately upstream of the photodetector 239, thus providing a wider beam of light that can detect the absorption of light by a larger sample of gases. While the collimator lens 208 may permit the use of smaller photodetectors, it is contemplated that the optical sensor assemblies may not include the collimator lens.

In the illustrated embodiment, the collimator lens 208 is coupled to the ring 107 of the base 104. More specifically, the collimator lens 208 is disposed between the webs 124 and 126 and located immediately downstream or in front of the LED 204. The collimator lens 208 is located against the inner face of the ring 107 that defines the opening 112. The lens 208 has a diameter greater than that of the opening 112. An O-ring 210 is pressed between the section of the inner face of ring 107 that defines the opening 112 and the lens 208, such that the O-ring 210 provides a seal around the opening 112. It is contemplated that any suitable fasteners, seals and/or other mounting devices can integrate the collimator lens 208 within the optical sensor assembly 202.

As best shown in FIGS. 12 and 13, each one of the optical sensor assemblies 202 is configured to measure absorption of light indicative of the concentration of gases by the sample of the corresponding gases within two linear paths L1, L2 extending diametrically across the opening 106. In particular, each optical sensor assembly 202 may further comprise a prismatic reflector 218, which is coupled to a portion of the ring 107 diametrically opposite to LED 204, the photodetector 239, and the collimator lens 208 of the corresponding optical sensor assembly 202, such that the beam of light is transmitted along one path L1 from the collimator lens 208 to the prismatic reflector 218. The prismatic reflector 218 is configured and positioned to reflect this light beam back across the opening 106 along the path L2 and into the ring opening 112 adjacent to where the light was emitted. One such reflector is sold as the TECHSPEC Fused Silica Wedge Prism by Edmund Optis of Barrington, N.J., United States. However, the optical sensor assembly can include any suitable prismatic reflector, and other embodiments of the optical sensor assembly do not have a prismatic reflector. In this example, the prismatic reflector 218 is mounted immediately adjacent to the ring opening 110 opposite the ring opening 112 through which the light from the associated LED 204 is emitted. More specifically, the prismatic reflector 218 for a first one of the optical sensor assemblies 202 is mounted between the pair of webs 114, and the prismatic reflector 218 for the second sensor assembly is mounted between webs 116 and 118. A retaining ring 216 holds the prismatic reflector 218 between the webs with which the reflector is associated. The prismatic reflector 218 has a face that subtends an area that is greater than the area of the adjacent window. An O-ring 220 is disposed between the perimeter section of the reflector and the portion of the inner ring that surrounds the opening 110. The O-ring 220 thus provides a seal between the ring 107 and the prismatic reflector 218.

While specific arrangements of the optical sensor assemblies are described above and illustrated in the figures, alternative arrangements are contemplated.

Figure 18:
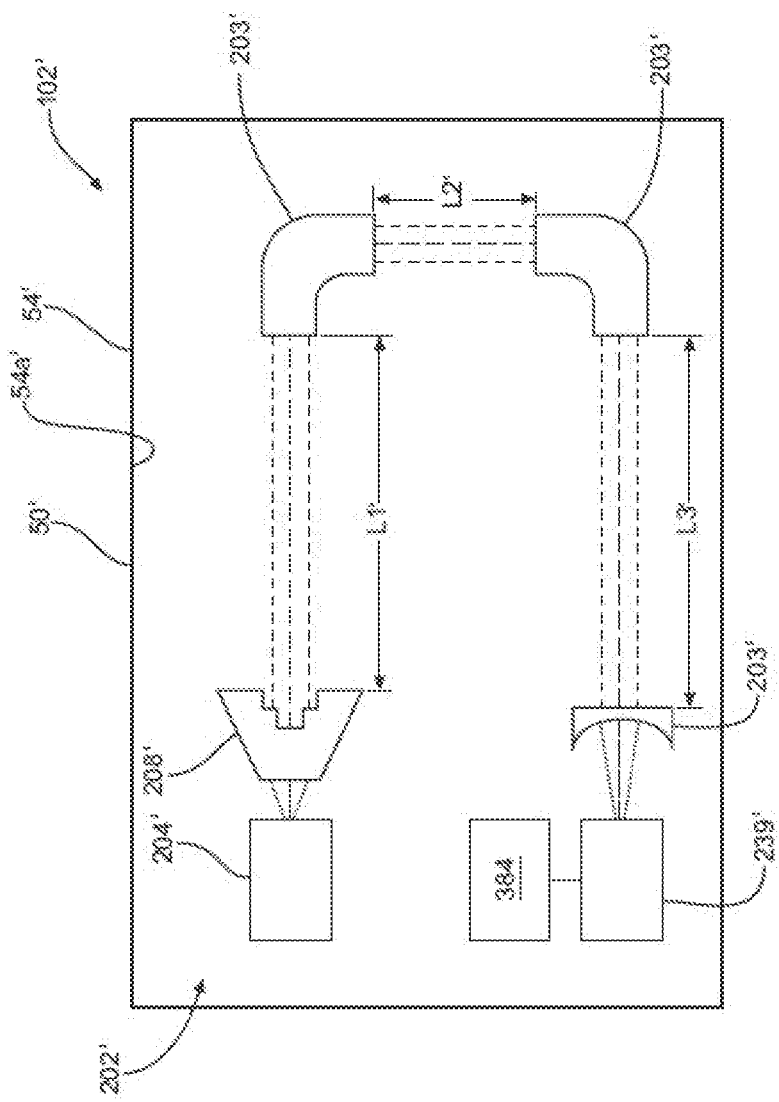
FIG. 18 is a schematic diagram of a portion of another exemplary sensor module, showing the sensor module comprising multiple light control elements, with the sensor module being configured to measure light absorption by multiple samples of one sterilant gas indicative of the concentration of the gas.

Referring to FIG. 18, another exemplary optical sensor assembly 202' can be configured to measure light absorption indicative of the concentration of sterilant gases along a multi-segmented path comprising two or more linear paths. By joining multiple linear paths, the total length of the ultimately detected light within the interior of the container can be greater than if only one segment of light is measured. In other words, as compared to the two light paths L1, L2 shown in FIGS. 12 and 13, three or more linear paths L1', L2', L3' can provide a longer light path for a larger sample of sterilant gas that absorbs more light at a wavelength corresponding with the sterilant gas. The comparably larger total amount of light absorption along a longer path can provide a more accurate determination of the concentration of sterilant gas.

As shown in FIG. 18, the exemplary optical sensor assembly 202' comprises multiple elements that are similar to the elements of the optical sensor assemblies 202 shown in FIGS. 14 and 17. However, in contrast to the previous examples, the optical sensor assembly 202' can further comprise multiple light wave guides, light pipes, fiber optic elements, reflectors, or various other light control elements 203' configured to redirect the light beam along two or more distinct linear paths to measure the concentration of a comparably larger sample of sterilant gases. These distinct linear paths may not necessarily be parallel or aligned adjacent with one another.

The distinct linear paths may be disposed within the sensor module 102 or within the container 50 to measure light absorption of the sterilant gas at various boundary conditions of the container 50. While the light paths L1, L2 of the previous examples shown in FIGS. 12 and 15 are configured to measure light absorption indicative of the concentration of sterilant gas adjacent to the filter medium 410, the optical sensor assembly 202' of FIG. 18 comprises multiple light control elements 203' configured to provide multiple light paths L L2', L3' adjacent to the inner surfaces 54a' of the panel 54' of the container 50'. Similar sensor assemblies may be coupled to each panel of the container 50'. In particular, each one of the light control elements 203' can be arranged on an end section of each panel of the container 50' opposite to an end section of the same planar panel 54' that carries the LED 204', the photodetector 239', or the other light control element 203'. More specifically, because light travels in a linear direction, each one of the LED 204', the two light control elements 203' and the photodetector 239' can be arranged on a corresponding one of the four quadrants of each planar quadrilateral panel 54', such that the linear paths L1', L2', L3' for the light beams are disposed along or adjacent to the inner surface of each planar panel 54' of the body 52, with the linear path L2' being disposed perpendicular to the linear paths L1', L3'. Moreover, these linear paths L1', L2', L3' may be disposed between the inner surface of the container 50' and the rack or the instruments carried on the rack, such that the optical sensor assemblies 202' do not occupy space required by the rack or the instruments.

The linear paths defined by the light control elements 203' are not particularly limited, and it is contemplated that the linear paths may be directed along the internal perimeter of the container along an inner side of three panels 54, 56 of the container and around the surgical instruments contained therein. Moreover, the light control elements 203' may be arranged to define linear paths that are directed near instruments having recessed portions or other surface configurations that are difficult to sterilize. Furthermore, the light control elements may be integral parts of various other optical sensor assemblies configured to measure the concentration of sterilant gases.

Continuing with the example shown in FIG. 17, each one of the optical sensor assemblies 202 further comprises the photodetector 239, as introduced above. The photodetector 239 is located on the side of the web 126 opposite the side adjacent to where the LED 204 is located. The photodetector 239 is thus located between the webs 124 and 126. The photodetector 239 is mounted to a circuit board 224, which is secured to the free ends of the webs 124 and 126. The LED 204 is also shown mounted to the circuit board 224. A filter 228 is shown outwardly of the opening 112 and between the webs 124 and 126. The lens 208 is shown between filter 228 and the adjacent photodetector 239. Spacers 230 and 234 are also located between the webs 124 and 126 to hold the filter 228 and lens 208 in the proper positions between the webs 124 and 126. An O-ring 227 is located between the inner face of the ring 107 that defines opening 112 and the filter 228. The O-ring 227 is compressed between the ring and the filter 228. The O-ring 227 thus provides a seal between ring 107 and the filter 228.

In this example, each one of the optical sensor assemblies 202 is configured to determine absorption of light indicative of the concentrations of a corresponding one of two different gases within the container 50. In particular, the photodetector 239 integral with a first one of the optical sensor assemblies 202 is configured to generate a signal representative of the absorption of light indicative of the concentration of a first gas. For example, if one of the gases to be measured is steam, the associated optical sensor assembly 202 will include components configured to measure the absorption of light at the 940 or 1360 nm wavelength, the wavelength of light absorbed by water vapor. Thus, in some examples, the filter 228 that is part of the first optical sensor assembly 202 filters out light other than light of the wavelength that is absorbed by the first gas. Moreover, the photodetector 239 integral with the second optical sensor assembly 202 can be configured to generate a signal representative of the concentration of a second gas different from the first gas. If the second gas that is being measured is vaporized hydrogen peroxide, the second optical sensor assembly 202 is assembled from components able to generate signals representative of the absorption of light at the 245 or 1420 nm wavelength. These wavelengths of light are absorbed by hydrogen peroxide. The filter 228 that is part of the second optical sensor assembly 202 filters out light other than light of the wavelength that is absorbed by the second gas.

While each one of the dedicated optical sensor assemblies 202, 202' of corresponding FIGS. 12-18 are configured to measure the absorption of light indicative of the concentration of only one sterilant gas, an optical sensor assembly configured to simultaneously measure light absorption indicative of the concentrations of multiple sterilant gases can be used in combination with a processor and a lookup table to determine whether the instruments inside the container have been exposed to a desired level of sterilization, i.e., whether the exposure time to a certain concentration of gas correlates to the desired level of sterility.

Referring to FIG. 19, another exemplary sensor module 102" comprises an optical sensor assembly comprising a micro-spectrometer 202". One such micro-spectrometer 202" is sold under the brand name C12666MA by Hamamatsu, of Bridgewater, N.J., United States. However, the optical sensor assembly can include any suitable micro-spectrometer, and other embodiments of the optical sensor assembly may not have a micro-spectrometer. Spectroscopy can analyze a narrower bandwidth of light frequencies that facilitates the ability to measure at single or multiple absorption peaks for various gases, as compared to the optical sensor assemblies 202, 202' of FIGS. 12-18. In particular, spectroscopy also yields a measurement having a selectable and more precise bandwidth tolerance as compared to conventional filters which have bandwidths of typically +/−10 nm or +/−5 nm). Also, spectroscopy allows measurements at multiple nominal frequencies, which can be used to measure a target gas to improve accuracy. As one example, both 940 nm and 1360 nm wavelengths can be used to determine water vapor concentration, and the processor 384 (FIG. 11) can use these measurements to calculate the concentration of sterilant gas based on the Beer-Lambert law. Thus, a spectrometer can be used to measure the light intensity of a light beam at multiple target wavelengths and analyze only a wavelength range of interest. Non-limiting examples of wavelength ranges can include 245 nm+/−0.5 nm, 245 nm+/−1.0 nm, or 1360 nm+/−1 nm. In other words, for examples using the spectrometer, the light does not have to be accurately filtered by the filters of the previous example, and the measurement accuracy around the target wavelength is programmable and calculated from a data curve generated during measurement.

The micro-spectrometer 202" is configured to measure the concentrations of multiple sterilant gases thus providing a comparably more compact sensor module 202" than sensor modules having more than one optical sensor assembly. Specifically, this micro-spectrometer 202" may comprise a light source, such as LED 204", configured to emit light having a range of distinct wavelengths and, optionally, a collimator lens 208" configured to collimate and direct the light beam along a first linear path L1". Furthermore, while the previous exemplary optical sensor assembly 202' of FIG. 18 comprises two light control elements 203' for re-directing the light beam through sterilant gases along a second linear path L2' between the two light control elements 203' and then re-directing the light beam along the third linear path L3' parallel to and aligned with the first linear path L1', the present exemplary micro-spectrometer 202" of FIG. 19 may further comprise one light control element 203" that comprises a single retro-reflector configured to receive the light beam from the first linear path L1" and re-direct the light beam along a second linear path L2" parallel to and aligned with the first linear path L1", thus resulting in a higher absorption value and increased resolution as compared to a single path for a light beam that is not re-directed by a retro-reflector. The higher absorption value and the increased resolution, as provided by the re-directed light beam, can be particularly useful in measuring water vapor when there is a lack of humidity, because humidity can have a substantial effect on the sterilization efficacy of the sterilant gas. Of course, the number of retro-reflectors, collimator lenses, and other components are not particularly limited, and any number may be suitably arranged to provide enhanced accuracy in determining the sterilization process conditions within the container.

The position of the micro-spectrometer, light source, and retro-reflectors is not particularly limited, so long as the micro-spectrometer is arranged to receive light emitted from the light source after the light has passed through a sufficient volume of gas present within the interior environment of the sterilization container. For example, the micro-spectrometer, light source, and retro-reflectors may be coupled to the lid, side panels, or bottom of the container, or may be coupled to the filter frame.

Furthermore, the sensor module 102" may further comprise another light control element 203" that comprises a Thermal infrared spectroscopy (TIR) collector, which is configured to receive the light beam from the TIR optic guide and narrow the same. The sensor module 102" of FIG. 19 can comprise a single transducer 239" configured to receive the narrowed light beam from the TIR collector and thus provide a signal and corresponding data for measuring the concentrations of multiple sterilant gases. The transducer 239" can be an IR spectrometer configured to send a signal indicative of measured data to the processor 384 (see FIG. 11) by wireless or wired transmission.

Referring to FIG. 20, another exemplary FTIR micro-spectrometer 202''' uses Fourier Transform Infrared (FTIR) spectroscopy to simultaneously collect high spectral resolution data over a wide spectral range and provide data to the processor 384 for determining the concentrations of multiple sterilant gases. This FTIR micro-spectrometer 202''' provides benefits similar to those provided by the micro-spectrometer 202" of FIG. 19. In particular, the FTIR micro-spectrometer 202' can measure and analyze a narrower bandwidth of light that facilitates the ability to measure at absorption peaks for various gases, as compared to the optical sensor assemblies 202, 202' of FIGS. 12-18. Moreover, a retro-reflector can be configured to re-direct a light beam so as to increase light absorption and resolution, as compared to a single path for a light beam that is not re-directed by a retro-reflector. The higher absorption value and the increased resolution, as provided by the re-directed light beam, can be particularly useful in measuring water vapor when there is low humidity, because humidity can have a substantial effect on the efficacy of the sterilant gas. The FTIR micro-spectrometer 202''' of FIG. 20 has multiple components, which are similar to components of the optical sensor assembly 202" of FIG. 19. However, while the optical sensor assembly 202" of FIG. 19 uses thermal infrared spectroscopy (TIR) spectroscopy to measure data corresponding with the concentrations of sterilant gases, the FTIR micro-spectrometer 202''' is an optical sensor assembly using FTIR spectroscopy to measure the data. In one example, the processor 384 (FIG. 11) can analyze this data in combination with data received from temperature sensors and pressure sensors to determine the sterilant gas concentration or steam saturation state. In other examples, more than one retro-reflector can be disposed between the LED 204''' and the transducer 239" so as to increase the cumulative length of the light path and thus increase the light absorption and resolution of the micro-spectrometer 202'''.

As shown in FIG. 11, the processor 384 may receive a signal from the transducer 239'', which in this example comprises a FTIR spectrometer. The processor 384 may generate an interferogram 205''' by making measurements of the light energy signal at many discrete positions 207''' of a moving mirror integral to the FTIR spectrometer. The Fourier transform can convert the interferogram into an actual spectrum. Fourier transform spectrometers offer significant advantages over dispersive (i.e. grating and prism) spectrometers. In particular, the FTIR spectrometer can monitor all wavelengths simultaneously throughout the entire measurement and increase signal-to-noise ratio, as compared to the optical sensor assemblies 202, 202' of FIGS. 12-18.

It should be further appreciated that suitable spectrometers other than those explicitly contemplated above may be utilized, and those spectrometers may use any suitable spectroscopy technique in order to analyze the light absorption data or other characteristics of the sterilant gases within the container.

Any of the gas concentration sensors, such as one of the optical sensor assemblies 202'', 202''', can be used in combination with a temperature sensor and/or a pressure sensor, as described below, to measure the steam saturation state, as described below, or other characteristics within the container during the sterilization process for determining whether a desired level of sterilization for the instruments has been achieved.

Figure 8:
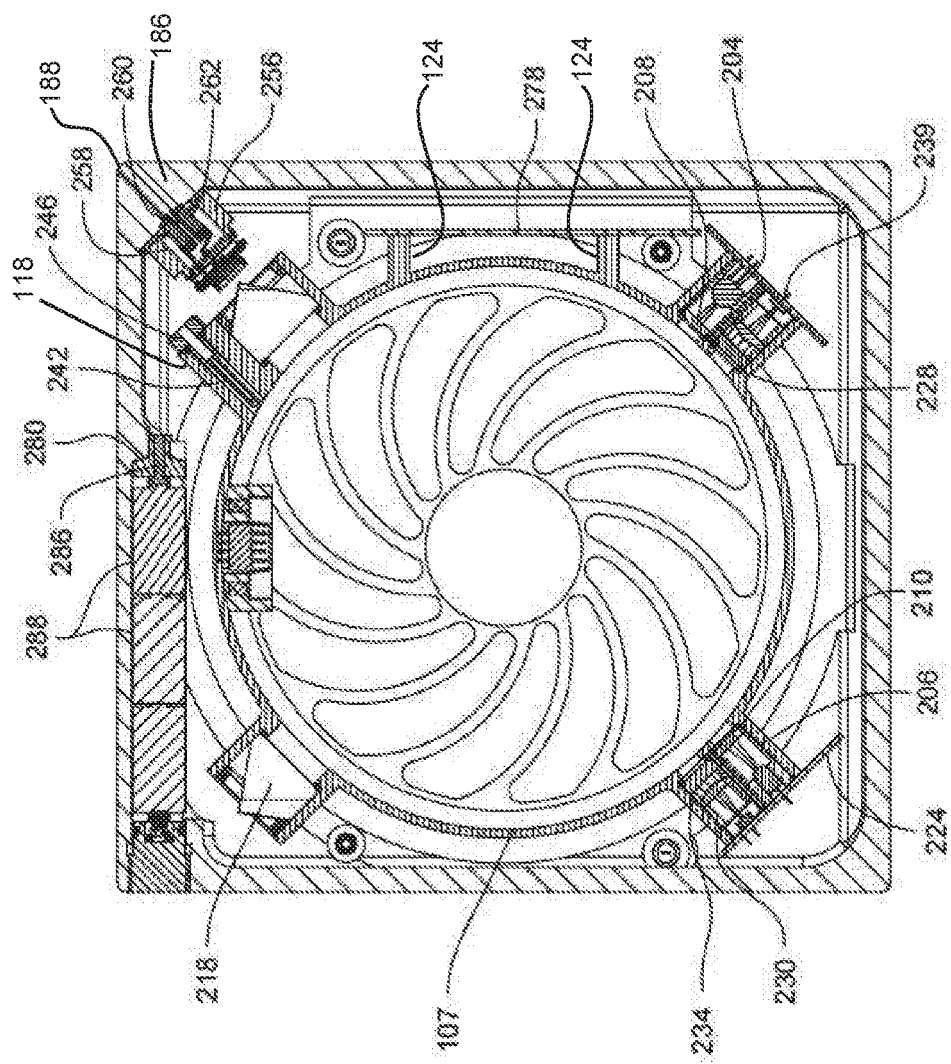
FIG. 8 is a cross-sectional view of multiple sensors being mounted to the base and shell of the sensor module of FIG. 3.
Figure 10C:
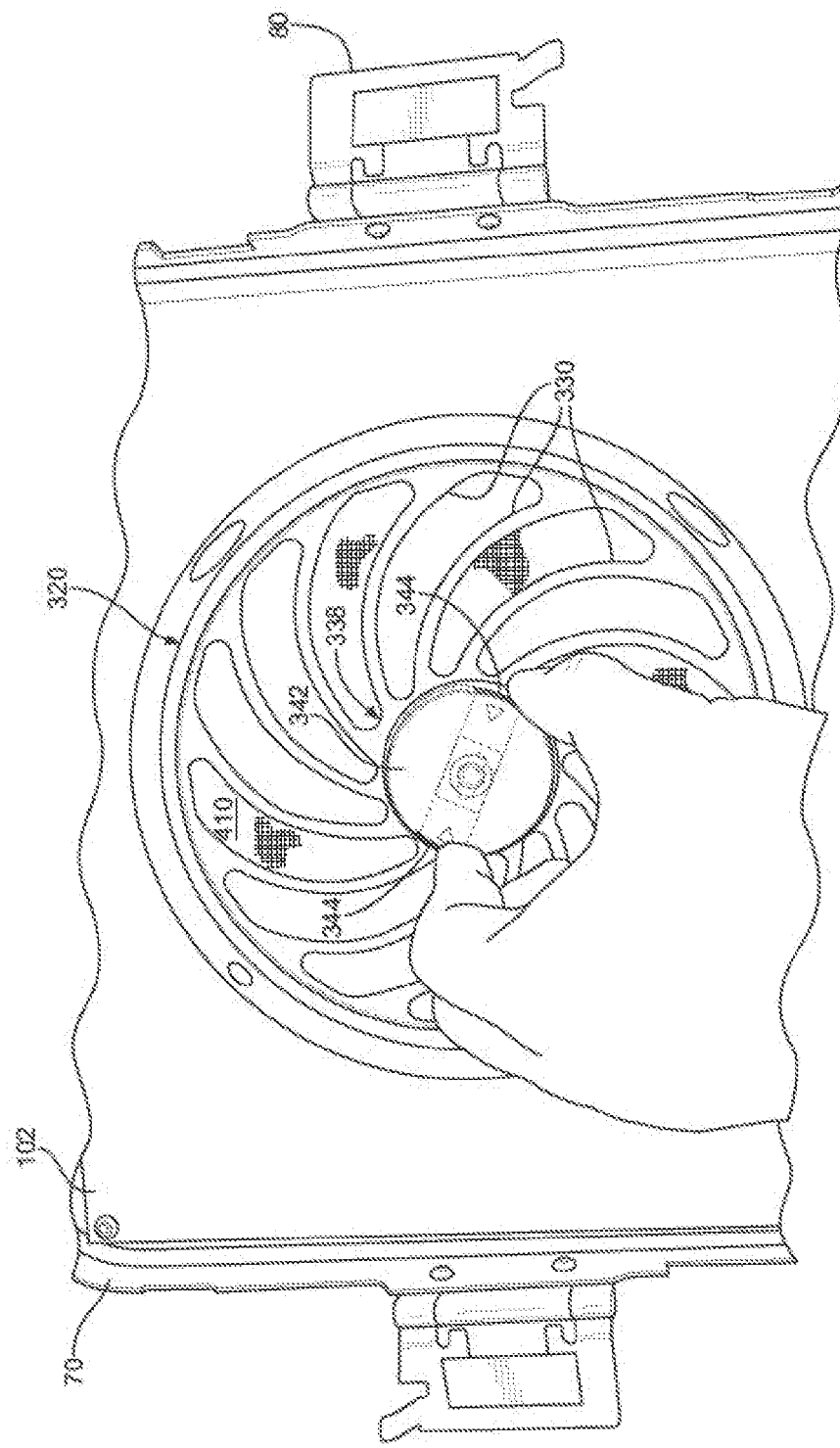
FIG. 10C is a bottom view of the filter frame of FIG. 10B, showing the latch assembly being actuated to release the filter frame, sensor module, and filter medium from the lid.
Figure 10D:
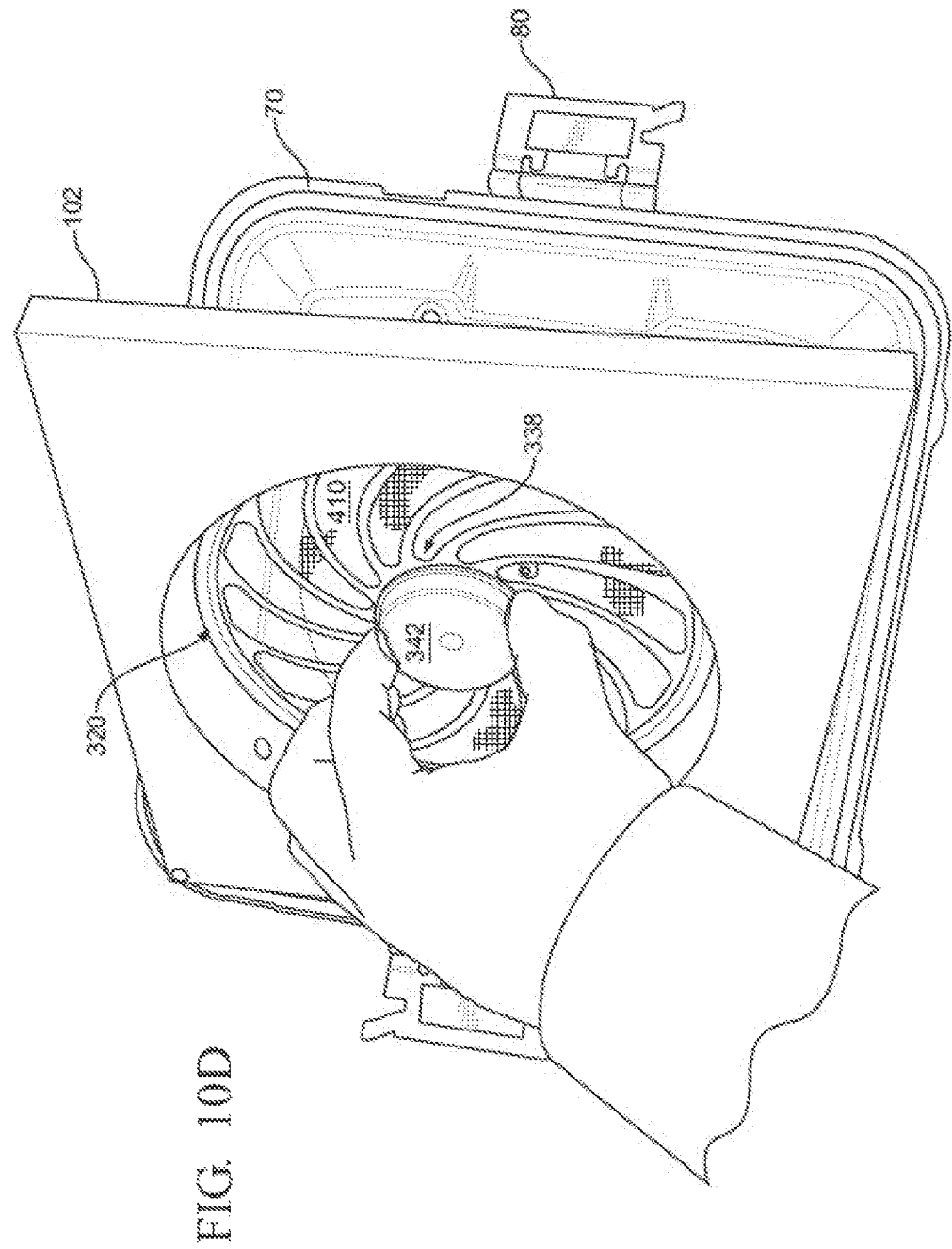
FIG. 10D is a bottom view of the lid of FIG. 10C, showing the sensor module and filter frame being removed from the lid while the filter medium remains positioned against the lid.
Figure 10E:
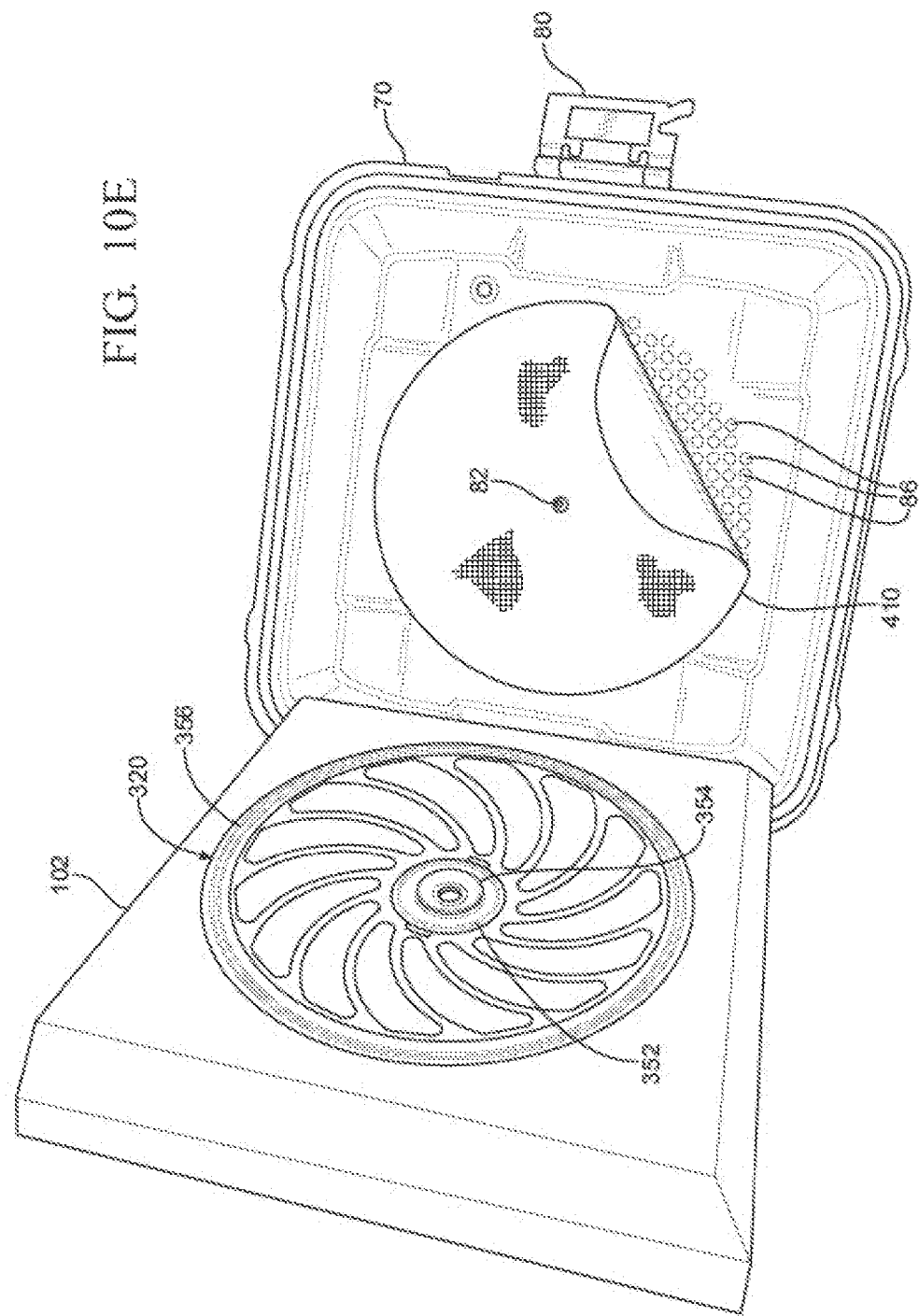
FIG. 10E is a bottom view of the lid of FIG. 10D, showing the filter medium being removed from the lid after the sensor module and filter frame have been removed from the lid.

Referring to FIGS. 5 and 8, the sensor module 102 can further include a temperature sensor 240. The exemplary temperature sensor 240 comprises a closed-ended tube 242 formed from material that is thermally conductive and will not corrode when exposed to the sterilant gases introduced into the sterilization container. One non-limiting example of the tube 242 is formed from aluminum and mounted in bore 120 so the closed end of the tube 242 is located adjacent the void space defined by ring 107. A fitting 246 holds the tube 242 to web 118. An O-ring 244 is disposed around the head of the fitting 246 adjacent the end of the web 118 spaced from ring 107. The O-ring 244 provides a seal between the web 118 and the fitting 246.

The temperature sensor 240 can include a temperature sensitive transducer disposed in the closed-ended tube 242. In some examples, the transducer can be a thermistor. The temperature sensor 240 can be configured to send a signal indicative of temperature to the processor 384 (FIG. 11) by wireless or wired transmission. It should be appreciated that any suitable type of temperature sensor may be utilized, including, but not limited to, thermocouples, resistive temperature devices, infrared sensors, bimetallic devices, phase change indicators, etc. Furthermore, the temperature sensor may be positioned in any suitable location relative to the sterilization container, so long as the temperature sensor is able to sense the temperature within the interior environment of the sterilization container.

Continuing still with the previous examples of FIGS. 5 and 8, the sensor module 102 may further comprise the pressure sensor 256. In the illustrated embodiment, the pressure sensor 256 comprises a small open-ended housing 258 mounted to the module shell so as to be disposed against the face of block 186 integral with shell 152. The housing 258 is sealingly mounted to the shell 152 so that bore 188 opens into the open end of the housing. Furthermore, while fluids may enter the housing 258 as condensate during a sterilization process or as fluids corresponding with washing or cleaning of the container, the housing 258 and components therein can be arranged in a configuration to permit those fluids to drain out of the housing 258, such that the accuracy of the pressure sensor 256 is maintained over time.

The pressure sensor 256 may further comprise two pressure-sensitive transducers 260, 262 contained within the housing 258. In some examples, both pressure-sensitive transducers 260, 262 are capacitor type transducers. The capacitance of each transducer 260, 262 varies as a function of the ambient absolute pressure. A first one of the transducers 260 provides relatively accurate measurements of ambient absolute pressure for relatively high pressures, such as a pressure above a minimum pressure of 20 to 50 Torr. A second one of the transducers 262 provides relatively accurate measurements of absolute pressure for relatively low pressures. For the purposes of this description, a relatively low pressure is a pressure below a maximum pressure of between 10 and 100 Torr. The transducer 262 provides accurate measurements of pressure to a pressure of 0.5 Torr, more ideally to at least 0.2 Torr and more ideally still to 0.05 Torr. Not shown are the conductors that extend from transducers 260 and 262 through housing 258. Also not shown are the components that sealingly holds housing 258 against block 186.

The type of pressure sensors that may be used in conjunction with the sterilization container is not particularly limited, so long as the pressure sensor is capable of determining the pressure within the interior of the sterilization container. Without being limited, the pressure sensor may comprise a force-type pressure sensor, a resonant frequency pressure sensor, or any other suitable pressure sensor. When the sensor module is used for monitoring a sterilant agent like steam, it is preferred to use a pressure sensor that determines the absolute pressure of the steam so that characteristics such as the saturation state of the steam is more readily determined. The pressure sensor 256 can be configured to send a signal indicative of the measured pressure to the processor 384 (FIG. 11) by wireless or wired transmission.

Processor 384 may further comprise a memory, which stores the operating instructions for the processor 384, including empirical data directed to various measured characteristics, such as benchmark light absorption values, temperature thresholds, pressure thresholds, and/or color changes empirically determined to ensure the desired level of sterilization. Also stored in the memory are the data acquired by and generated by the processor 384 during the operation of the sensor module 102.

An on/off switch 382 is shown connected to the processor 384. While not seen elsewhere in the drawings, the on/off switch 382 is typically mounted to either the base 104 or ring 107.

The processor 384 is shown as outputting the signals that result in the current flow through the LEDs 268, 270 to actuate the same and communicate various characteristics of the container 50 based on input received from the one or more sensor modules, such as the gas concentration sensor, the temperature sensor, the pressure sensor, other characteristics of the sterilant gas, or any combination thereof. The processor 384 may be further in communication with the notification device described herein through wired or wireless transmission.

Referring to FIG. 8, a circuit board 278 is shown mounted to the free end of webs 124. While not seen, the circuit board 278 is the component internal to the module to which the processor 384 and other components (not illustrated) that actuate the module are mounted.

Referring to FIG. 11, while the cells 288 are shown as just being connected to the processor 384, it is understood that the cells 288 may be connected to other power-consuming components of the sensor module 102. Often these connections are through one or more voltage regulators not illustrated in the figures. Terminal 132 is shown as being connected to the processor 384. This connection allows instructions to be written to the processor 384 and the data stored in the memory integral with the processor to be read out. In some examples, as a result of connections between some of the pins integral with terminal 132 and the cells 288, charging current is applied to the cells over the terminal 132.

In certain embodiments, the sterilization container may further comprise a filter presence detector 209, as shown in FIG. 11. By detecting the presence of the filter medium 410, the HCP can confirm that that filter is present in the container before initiating the sterilization process. In this example, the filter presence sensor comprises two conductive pins 276. As shown in FIG. 9, each one of the pins 276 is mounted to the module shell 152 and is moveably mounted in a separate one of the openings 170 formed in the shell 152. The sterilization container further includes a biasing member configured to move the conductive pins 276 toward the filter medium 410, which urges the pin outwardly so that the ends of the pins project away from the upwardly facing surface of shell top panel 154. The biasing member can be a helical spring 279 around the pin 276. At least a portion of the lid plate 72 can be made of electrically conductive material, and the filter medium 410 can be comprised of a non-conductive material. The presence of the non-conductive filter medium 410 can open a circuit comprising the processor 384, such that the processor 384 can determine that the filter is present and thus proceeds with a method for determining whether the instruments were exposed to the threshold process conditions to ensure the desired level of sterilization. Also, in response to determining that the filter is present (based on the input of the filter presence detector 209), the processor 384 can generate a signal indicative of the same. The processor 384 can send this signal by wireless or wired transmission to the notification device, which in one form comprises the LEDs 268, 270, being further configured to communicate to an HCP that the filter is present in the module. However, as will be described below, the notification device can be any suitable mechanism capable of notifying the HCP that the filter is present in the module, such as audible notification device. If the filter medium 410 has not been mounted in the container 50, the pins 276 contact the conductive lid plate 72 to close the circuit comprising the processor 384, such that the processor 384 determines that the filter medium 410 is not present and sends a signal to the notification device to communicate the absence of the filter medium 410. Other types of filter presence indicators are also contemplated, such as mechanical or electromechanical filter presence indicators.

Referring to FIGS. 2 and 10A-10E, use of the sterilization enclosure, such as container 50 typically starts with the rack 62 on which one or more instruments is loaded within the container body 52. A filter medium 410 is placed against the inner surface of the lid plate. The filter frame 320 is then placed over the filter medium 410. In this step, the cap 342 is fitted over and latched to post 82 to hold the filter frame 320 to the lid 70. As a result of this latching, the filter medium 410 is biologically sealingly compressed between the lid and filter frame 320. In the illustrated embodiment, the sensor module 102 is coupled to the filter frame 320. As such, attachment of the filter frame over the filter medium 410 also fixes the position of the sensor module 102 relative to the sterilization container 50. In another embodiment, the sensor module is constructed as an integral part of the filter frame 320 to both sealingly compress the filter medium 410 against the container 50 and position the sensors adjacent to the filter medium 410 as described above.

During the step of latching sensor module 102 and filter frame 320 to the lid 70, the indicia 138 prompts the individual performing this process to position the module so the module is correctly oriented relative to the lid 70. When the module 102 is so oriented, in one embodiment, each LED 268 and 270 is disposed under a separate one of the transparent domes 92.

A user input device, such as on/off switch 382, may be engaged to actuate the sensor module 102. In response to the actuation of the sensor module 102, the processor 384 initially evaluates the filter presence indicator, such as the circuit associated with pins 276, to determine whether or not the filter is present. In the illustrated embodiment, if the circuit is open, the pins 276 are abutting the non-conductive filter medium 410. Accordingly, if the circuit is open, the processor 384 considers the sensor module 102 to be in a state in which the module is disposed below a filter medium 410. The processor does not take any additional action. If, alternatively, the filter presence indicator does not identify that a filter is located above the sensor module 102, the pins 276 press against the lid plate 72, which is comprised of conductive material. The abutment of the pins 276 against the lid plate 72 therefore closes the circuit formed by the pins 276. Accordingly, if processor 384 determines the circuit is in this state, the processor 384 considers the container 50 to be in the state in which a filter is not disposed between the lid 70 and the sensor module 102. When the processor 384 determines that the container 50 is in this state, the processor 384 provides an indication of this state to the HCP. In some examples, the processor 384 provides this indication with the notification device, such as by alternatively cycling the LEDs 268, 270 on and off.

In an alternate example, one of the pins could be removed and the circuit continuity with the lid can be facilitated through an electrical path established when the sensor module is mounted or latched to the lid. The remaining pin, in conjunction with the electrical path established to the lid when it is mounted or latched, would function as the filter presence monitor as described above. In yet another example, the filter presence monitor could be used in conjunction with the filter holder and without the other sterilization process sensors contained in the sensor module described above.

Assuming the filter medium 410 is properly mounted to the lid 70 (or other portion of the container that includes one or more apertures), the lid 70 is latched over the open end of the container body 52. The container 50, with one or more instruments 60 disposed in the interior of the container 50, is placed in a sterilizer and subjected to the sterilization process.

During the sterilization process, the one or more sensor assemblies 202, 202', 202", 202''', 240, 256 measure the characteristics within the interior of the container and, optionally, generate signals indicative of the same. Based on these signals, the processor 384 compares the measured characteristics with the threshold process conditions to determine whether or not a desired level of sterilization for the instruments has been achieved. A "validated sterilization process" is understood to be a sterilization process that, based on past testing, is known to sterilize a particular instrument to a desired level of sterilization that essentially ensures any microbial material on the instrument would be innocuous. A surgical instrument is often considered sterilized if the instrument has a desired level of sterilization corresponding to a 6-log reduction in micro-organisms. This means that the microorganism population on the instrument was likely reduced by at least 99.9999%. U.S. Patent Publication No. 2015/0374868, hereby incorporated by reference, provides an explanation of how to obtain environmental measurements for a validated sterilization process.

If as a result of the evaluation, the processor 384 may determine whether one or more instruments were exposed to threshold process conditions that ensure a validated sterilization process, the processor actuates the notification device, such as LED 270. However, it will be contemplated that the processor can actuate the LED 270 or other notification devices when the instruments are exposed to other desired levels of sterilization. In addition, or as an alternative to relying on the notification device, the HCP may look at the one or more sensors included with the container to determine whether one or more instruments were exposed to threshold process conditions to verify a validated sterilization process.

In one possible implementation, the green light emitted by the LED 270, which is visible through the overlying dome 92 (FIG. 4), provides the personnel with the notice that the instruments in the container 50 have been exposed to the threshold process conditions that ensure the desired level of sterilization. Alternatively, as a result of the evaluation, processor 384 may determine that one or more instruments 60 were not exposed to threshold process conditions that ensure a validated sterilization process or other desired level of sterilization. If the processor 384 makes this determination, the processor actuates LED 268. The red light emitted by LED 268 provides an indication that even though one or more instruments were subjected to a sterilization process, the instruments were not exposed to threshold process conditions that ensure the desired level of sterilization. This indication serves as a cue that further action needs to be taken to sterilize the instruments.

In another possible implementation, the notification device could utilize alternative notification modalities, such as by emitting a noise, to alert the HCP that the instruments within the container have or have not reached the desired level of sterilization.

While the first exemplary sterilization container comprises sensors that are typically disposed within the container, a second exemplary sterilization container can comprise sensors that are disposed outside of the container, yet fluidly communicate with the interior of the container. The sensors may be coupled directly to an external surface of the container or be integral components of a sensor module removably and aseptically coupled to the container. It should be understood that any of the sensors described above as being disposed within the interior of the sterilization container could alternatively be disposed outside the container, yet communicate with the interior of the container.

Figure 21:
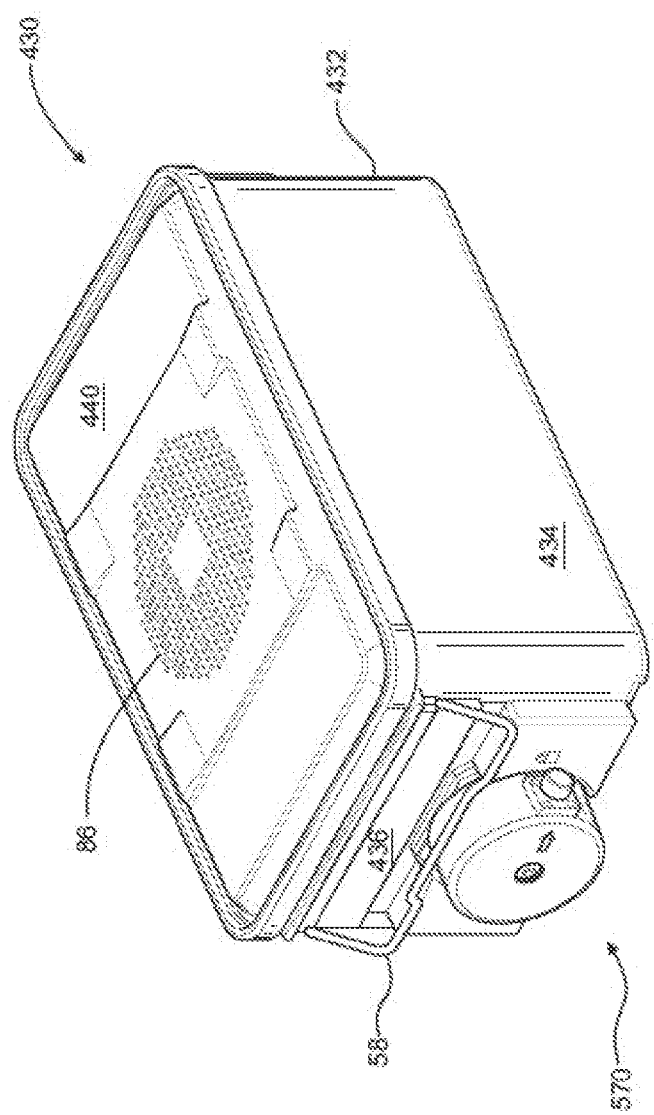
FIG. 21 is a perspective view of another example of a sterilization container, illustrating a sensor module coupled to an external surface of the container.
Figure 22:
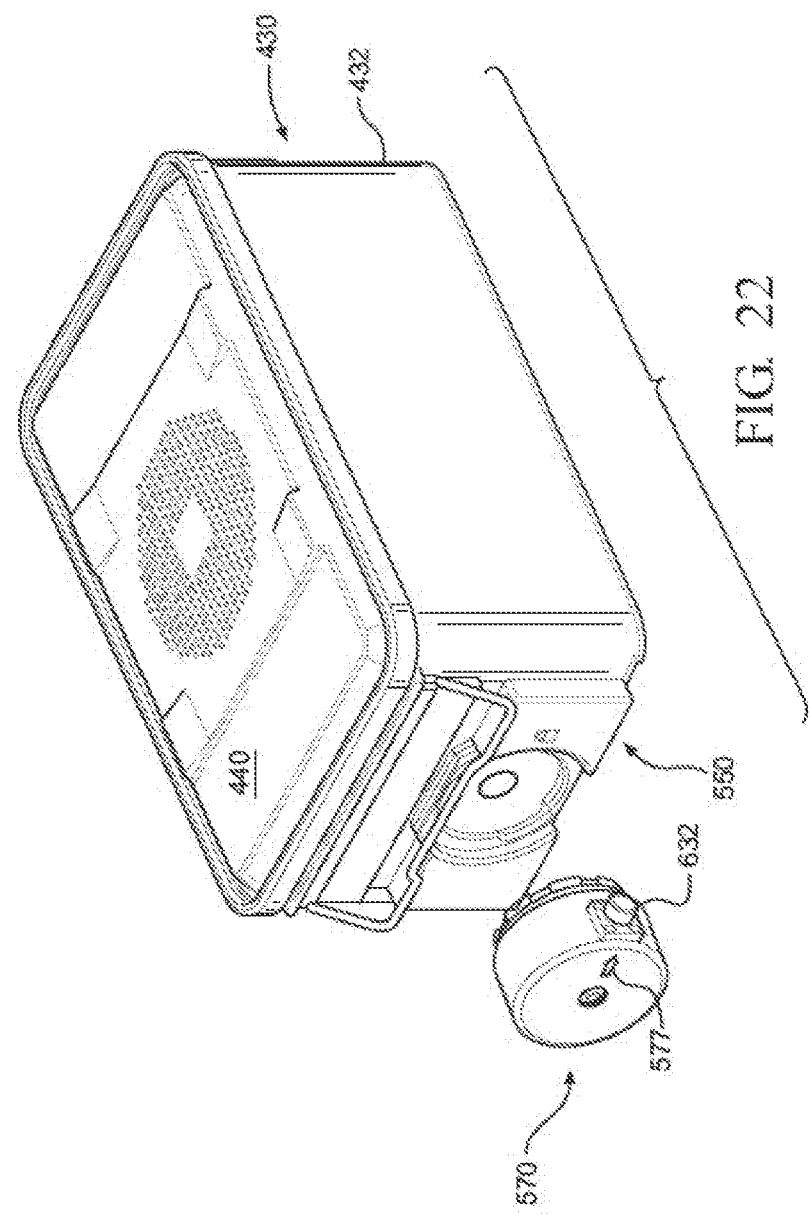
FIG. 22 is a perspective view of the sensor module spaced apart from the sterilization container of FIG. 21.

FIGS. 21 and 22 illustrate the second exemplary sterilization container 430 and a sensor module 570, which is removably coupled to the container 430 and contains one or more sensors that fluidly communicate with the container 430 as will be described below. In this example, the sensor module 570 is mounted to the outside of the container 430. In certain configurations, internal to the container is a valve 450 (See FIG. 23). Sensor module 570 is mounted to the container 430 adjacent the valve 450.

The sensor module 570 and container 430 may be arranged such that removably coupling the sensor module 570 to the container 430 opens the valve 450, such that sensors 620 (see FIG. 30) disposed within the sensor module 570 fluidly communicate with the interior of the container when the valve 450 is in the opened state. In turn, the sensor module 570 and the container 430 may be arranged and configured such that removing the sensor module 570 from the container 430 closes the valve 450, such that the fluid communication between the surrounding outside environment of the container 430 and the interior of the container is not established when the sensor module 570 is removed. In other words, the sensor module 570 and the container 430 are advantageously arranged such that the sensor module 570 can be decoupled from the container 430 without compromising the sterility of the interior of the container 430 and the instruments therein.

In the illustrated embodiment, container 430 includes a body 432 to which a lid 440 is removably attached. Body 432, like body 52, is formed from a number of panels that are arranged together to give the body a generally rectangular shape. A front panel 434 and a side panel 436 are identified in FIG. 21. Not seen are the back panel opposite the front panel 434 and the second side panel opposite the illustrated side panel 436. Also not seen is the bottom panel that extends between the front, back, and side panels. It is understood that bottom panel provides the body 52 with a closed-bottomed end. In other examples, the bottom panel could contain a filter and apertures similar to the filter and apertures on the lid, which allow sterilant gas to flow in and out of the container. The top of the body 52 is open. A handle 58, one seen in FIG. 21, is pivotally mounted to the outside of each of the side panels 436. Body 432 has a void space dimensioned to hold one or more surgical instruments. In another example, the body 432 can also include a rack that supports the instruments.

In the illustrated example, the valve 450 is mounted to the illustrated side panel 436 of the container body 432. The side panel 436 to which the valve is mounted includes a through opening 438, identified in FIG. 23. It is contemplated that the valve, and associated components, including the sensor module, may be coupled to any suitable location on the container, such as the lid, side panels, bottom panel, or other portions of the container. Furthermore, the sterilization container may optionally include two or more valve and sensor module assemblies.

Lid 440 is structurally similar to and functionally identical to the previously described lid 70 of the first exemplary container 50 illustrated in FIG. 3. Not seen are the components that latch the lid 440 to the top of the body 432 and that form a seal between the lid 440 and the body 432. The lid 440 is formed with apertures 86. Not seen is the filter, essentially filter medium 410, and the filter frame that removably holds the filter to the inner-directed face of the lid 440.

Referring to FIGS. 22-25, the valve 450 may be coupled to the body 432 of the container 430 and rotatable between an open state and a closed state. In this example, the valve 450 can comprise a valve cap 452 that is mounted to the body 432 against the inner surface of the associated side panel 436. The valve cap 452 can be generally planar in shape. More specifically, in this example, the valve cap 452 generally comprises a truncated disc. The valve cap 452 can have an inner face 454, which is directed toward the adjacent inner surface of the side panel 436. The valve cap 452 further can comprise a rim 460 that extends circumferentially around the inner face 454 and toward the adjacent surface of the side panel 436. The inner face 454 can comprise a circular groove 456 spaced radially inward from the rim 460.

The inner face 454 may comprise four ribs 458, which are disposed in and extend outwardly from the base of groove 456. These ribs 458 are equangularly spaced apart from each other. Each rib 458 can have a convex surface directed toward the side panel 436. More specifically, each rib 458 may extend arcuately from the base of the groove 456, such that the convex surface gradually curves toward the side panel 436 to a crest and then curves arcuately back to the base of the groove 456. Each one of the ribs 458 may be disposed entirely within the groove 456. Each one of the ribs 458 may extend across an entire cross-sectional width of the groove up to the inner perimeter of the rim 460. Of course, other configurations of the inner face are also contemplated.

The valve cap 452 further may comprise at least one hole 464 that fluidly communicates with the interior of the sterilization container. The hole 464 may extend from the inner face 454 to the opposed outer face 455. In the illustrated example, the valve 450 comprises four holes 464 equidistantly spaced from the center of the inner face 454. Furthermore, these holes 464 are equi-angularly spaced apart from one another. The inner face 454 of the valve cap 452 comprises four grooves 466 that surround a corresponding one of the four holes 464. The inner perimeter of each groove 466 is spaced radially outwardly from the outer perimeter of the corresponding hole 464.

The rim 460 may comprise an outer perimeter and a bore 468 that extends radially inwardly therefrom. While not seen in the Figures, bore 468 opens into the space immediately in front of the cap inner face 454.

The valve cap 452 may be coupled to the inner face of the side panel 436 of the body 432, such that the holes 464 in the valve cap 452 are equidistantly spaced radially outward from a central axis of the opening 438 in the adjacent side panel 436. Not illustrated is the assembly that holds the valve cap 452 static to the side panel 436. In some examples, the valve comprises fasteners (not shown) that extend through bores in both the side panel 436 and the valve cap 452 so as to hold the valve cap 452 to the side panel 436. Also, it should be understood that the valve cap 452 is secured to the side panel 436 so there is no gap between these components. In many examples, a gasket (not shown) may be disposed between the panel and the exposed face of the cap rim 460. The fasteners that hold the valve cap 452 to the side panel 436 can compress this gasket between the side panel 436 and the cap rim 460, such that the gasket comprises the seal between the side panel 436 and the valve cap 452.

A rotating valve plate 472 may be rotatable between an open state and a closed state relative to the valve cap 452. The valve plate 472 can include a bore 486 fluidly communicating with the holes 464 of the valve cap 452, which in turn fluidly communicates with the interior of the container, when the valve plate 472 is in the open state. When the sensor module 570 is rotatably coupled to the container 430, the sensor module 570 fluidly communicates with the bore 486 of the valve plate 472. In this example, the valve plate 472 is rotatably disposed between the inner surface of the side panel 436 and the adjacent inner face 454 of the valve cap 452. The valve plate 472 can comprise a circular base 474 and a rim 476 that extends circumferentially around the outer perimeter of the valve plate 472. A portion of the rim 476 extends inwardly, toward the valve cap 452. The valve plate 472 may be coupled to the valve cap 452, such that the rim 476 of the valve plate 472 seats within and is able to rotate in the groove 456 that surrounds the inner face 454 of the valve cap 452. The rim 476 also projects a slight distance in an outward direction from the face of the base 474 toward the adjacent inner surface of the container side panel 436.

The base 474 of the valve plate 472 may comprise an outer face adjacent to the side panel 436 and a boss 484 that extends from this outer face. The boss 484 has a cross-sectional shape that is non-circular. In the illustrated example, the boss 484 is the shape of a polygon and, more particularly, a hexagon. The boss 484 is dimensioned to rotate in opening 438 formed in the adjacent side panel 436. Also extending outwardly from base 474 is a step 483, which is circular in shape and surrounds the boss 484.

The valve plate 472 may comprise one or more channels 480 in fluid communication between the holes 464 of the valve cap 452 and the bore 486 of the valve plate 472 when the valve plate 472 is rotated to the open state. In particular, the valve plate 472 may comprise an inner face that is directed to the inner face 454 of the valve cap 452 and a plurality of channels 480. In the illustrated example, there are two channels 480, which bisect one another and intersect at the center of the plate base 474. The valve plate 472 is further formed so that when the plate is in a particular rotational orientation relative to the valve cap 452, each channel 480 is in registration with a separate one of the holes 464 formed in the valve cap 452. The width across each channel 480 is no greater than the diameter of the holes 464.

Figure 25:
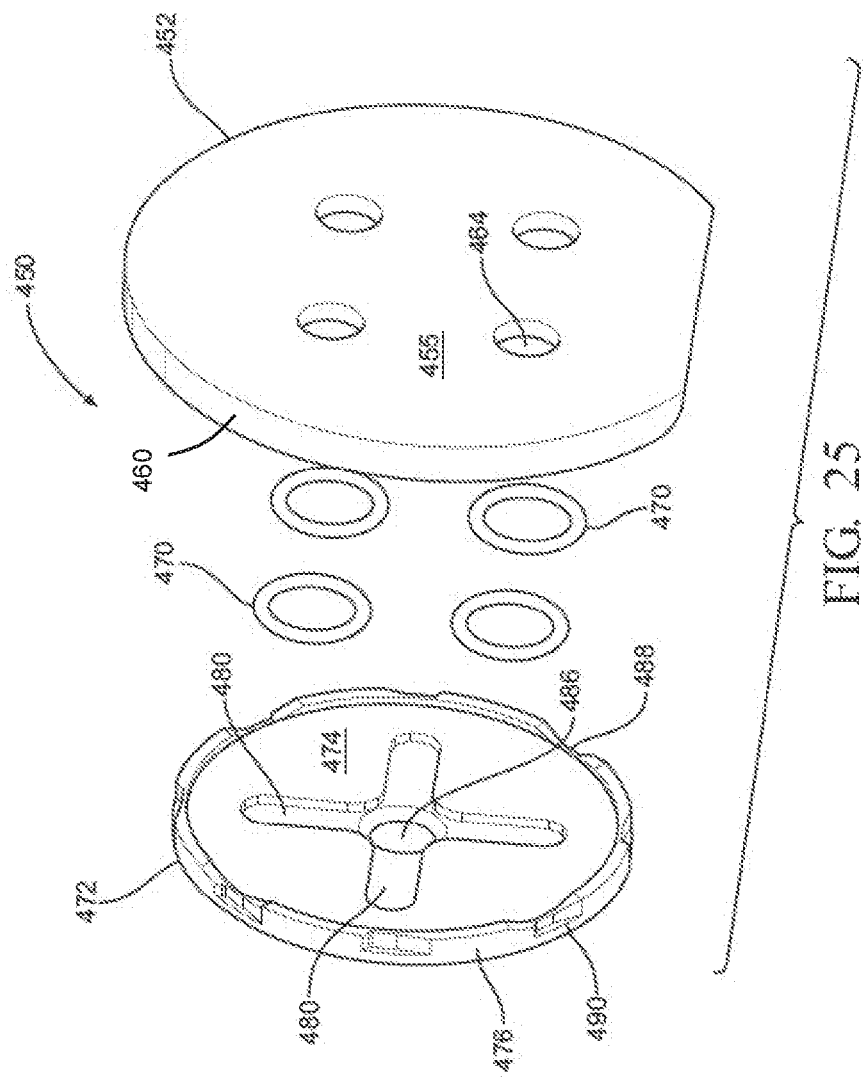
FIG. 25 is a second perspective view of the valve of FIG. 23.

The base 474 of the valve plate 472 may comprise the bore 486 extending from the inner face of the base 474 and outwardly through the boss 484. As best shown in FIG. 25, the rim 476 further comprises a number of arcuately spaced apart indentations 488 configured to receive a corresponding one of the ribs 458. Each indentation 488 extends inwardly from the face of the rim 476 that is located adjacent the base of the cap groove 456. Each indentation 488 can be concave in shape and complementary to the profile of the ribs 458. The number of indentations 488 can be equal to the number of cap ribs 458. The indentations 488 are angularly spaced apart from each other by the same angle about which the ribs 458 are spaced apart from each other.

While the valve 450 has been described in detail above, other configurations of the valve are contemplated so long as the valve is operable to establish fluid communication between the sensor module and the interior of the sterilization container when the sensor module is coupled to sterilization container, and is also operable to maintain sterility of the sterilization container when the sensor module is decoupled from the sterilization container.

In the illustrated embodiment, the valve plate 472 is configured to rotate in one direction relative to the valve cap 452. In particular, the rim 476 of valve plate 472 has an additional set of indentations 490, which extend radially inwardly from the outer circular surface of the rim 476. Some of the indentations 488 and indentations 490 intersect.

Figure 24:
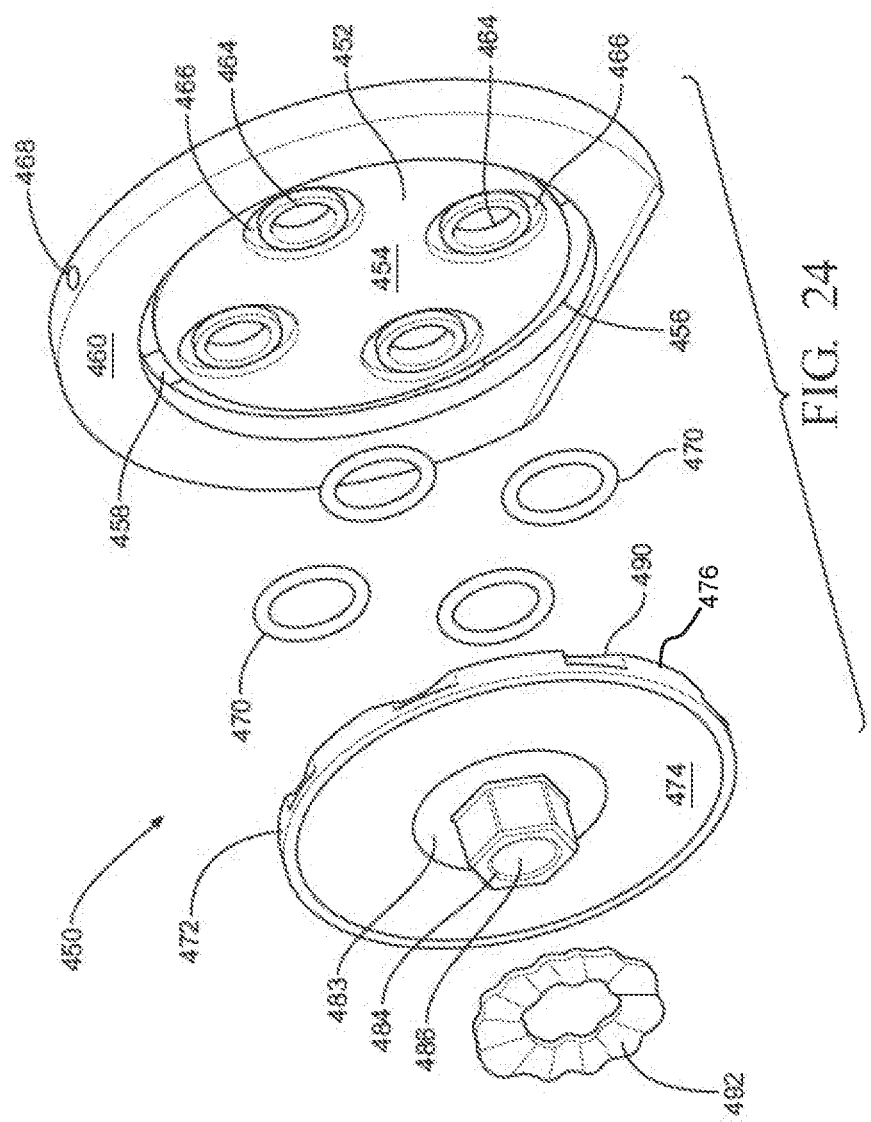
FIG. 24 is a first perspective view of the valve of FIG. 23.

When the valve 450 is mounted to the container body 432, in the illustrated embodiment, the valve plate 472 is disposed between the inner surface of side panel 436 and the valve cap 452. An O-ring 470 is seated in each of the grooves 466 internal to the valve cap 452. Boss 484 extends through the opening 438 formed in the panel. The components forming the valve 450 are dimensioned so that the valve plate 472 can engage in limited longitudinal movement between the surface of side panel 436 and the valve cap 452. As seen in FIG. 24, a biasing member, such as wave washer 492 is disposed around the boss 484. The wave washer 492 is compressed between the side panel 436 and the adjacent face of the valve plate base 474. The wave washer 492 presses the valve plate 472 toward the static inner face 454 of the valve cap 452. Other types of biasing members other than wave washer 492 may be used.

Figure 23:
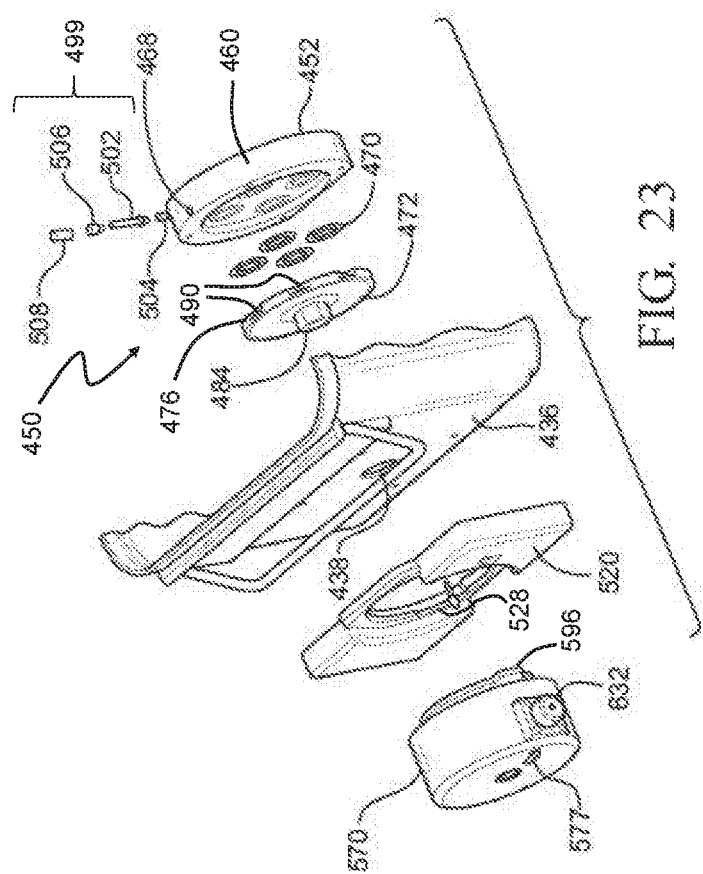
FIG. 23 is an exploded view of the valve of a portion of the sterilization container of FIG. 21, illustrating the container comprising a normally closed valve for aseptically and removably coupling the sensor module to the container.

Referring to FIG. 23, a valve locking assembly 499 may be provided to lock the valve into the closed state when the sensor module is decoupled from the sterilization container. The valve locking assembly 499 is generally operable to block the rotation of the valve plate 472 in one direction, and allow rotation in the opposite direction. The valve locking assembly 499 prevents the HCP from inadvertently establishing communication between the interior of the sterilization container and external environment while the interior of the container is in the sterile state. More particularly, the valve locking assembly 499 prevents the HCP from moving the valve plate to the open state from the outside of the sterilization container when the sensor module is decoupled from the sterilization container.

In one embodiment, the valve locking assembly 499 comprises pin 502, seen best in FIG. 23, slidably mounted in cap bore 468, along with spring 504 and a ferrule 506, which are disposed in the bore 468 and are positioned to exert a force on the pin 502 in a direction toward the center of the valve plate 472, such that the tip of the pin 502 will seat in indentations 490 formed in the valve plate 472 to block the rotation of the valve plate 472 in one direction and allow the rotation in the opposite direction. In this example, each indentation 490 can include a wall that extends perpendicularly to a tangent of the rim 476 and radially inward from the rim 476 toward a valley, such that the pin 502 is configured to contact this wall and prohibit rotation of the valve plate 472 from the closed state to an open state. Furthermore, each indentation 490 can include an opposing wall or ramp portion that extends radially inward from the rim 476 to permit the pin to slide along the ramp and out of the indentation 490, such that the valve plate 472 may be rotated from the open state to the closed state. A head 508 may be disposed over the free end of the pin 502, the end of the pin that projects outwardly of the valve cap 452. An individual can manually apply a force using his finger to overcome the force imposed by the spring 504, such that the pin can be withdrawn from the indentation 490 in which the pin 502 is seated thus permitting the valve plate 472 to rotate from the closed state to the open state. Put another way, the pin 502 and indentations 490 can function together as a manually-operated rotatable valve locking assembly that can selectively allow rotation of the valve 450 from the closed state to the open state when the container 50 is opened and an individual accesses the valve locking assembly 499 within the interior of the container. Other configurations of the valve locking assembly are also contemplated, such a frictional or camming engagement to prevent rotation of the valve plate in one direction upon engagement, i.e., after removal of the sensor module.

Figure 26:
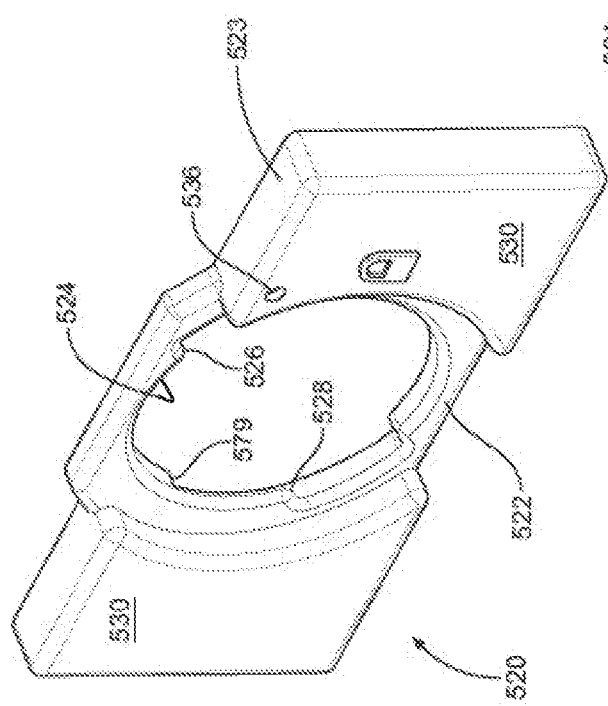
FIG. 26 is a perspective view of the valve bezel plate of FIG. 23.
Figure 27:
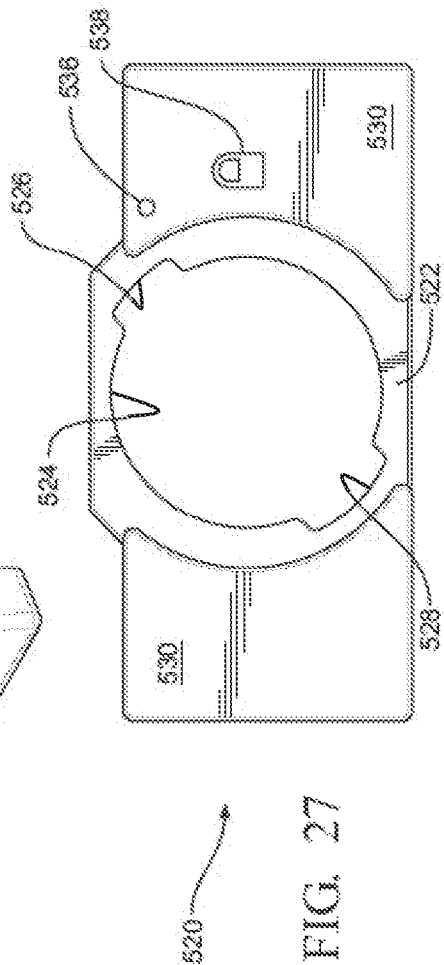
FIG. 27 is a plan view of the valve bezel plate of FIG. 26.

Referring to FIGS. 23, 26, and 27, the valve 450 may further comprise a bezel plate 520 configured to sealingly contain electrical components therein and attach the sensor module 570 to the body 432. The bezel plate 520 is disposed over the outer surface of the side panel 436 to which the valve 450 is mounted. The bezel plate 520 may include a ring-shaped core 522, and two planar wings 530 extend outwardly from the opposed sides of the core 522. In the illustrated example, the core 522 extends outwardly from the opposed top and bottom edges of the wings 530. A rim 523 extends circumferentially outwardly around both the core 522 and wings 530. The rim 523 also extends inwardly from the core 522 and wings 530. When valve 450 is mounted to the container 432, the bezel plate 520 is positioned so the inner planar face of the rim 523 is the portion that abuts the side panel 436. The rim 523 thus holds both the core 522 and wings 530 away from the adjacent surface of side panel 436. Thus, electrical components of the valve 450 can be sealingly contained within the wings 530 to protect those components from the effects of the sterilization process.

The bezel plate 520 is configured to removably couple the sensor module 570 to the valve 450. More specifically, in this example, the core 522 may define a center opening 524. The core 522 can further define two notches 526, 528 (see FIG. 27). The notches 526, 528 are diametrically opposed to each other relative to the center of opening 524. The notches 526, 528 each open into the opening 524. The notches 526, 528 subtend different arcs around opening 524. In the illustrated example, notch 526 subtends a relatively small arc, and the notch 528 subtends a comparably larger arc. The sensor module 570 comprises two tabs 596, 598 (see FIG. 29) configured to be received in a corresponding one of the two notches 526, 528, such that subsequent rotation of the sensor module 570 attaches the sensor module 570 to the valve 450 and container 430.

In the illustrated example, the bezel plate 520 may comprise one or more of the wings 530 including a hole 536, which is configured to receive an LED contained under the corresponding wing 530 and permit light to be emitted therethrough. The wings 530 can further comprise an icon 538 in the shape of a lock, which is positioned on the wings 530 so as to align with an icon 577 (see FIG. 28) in the shape of an arrow formed on the sensor module 570 when the sensor module 570 is rotated to a position that removably attaches the sensor module 570 to the body 432.

Figure 28:
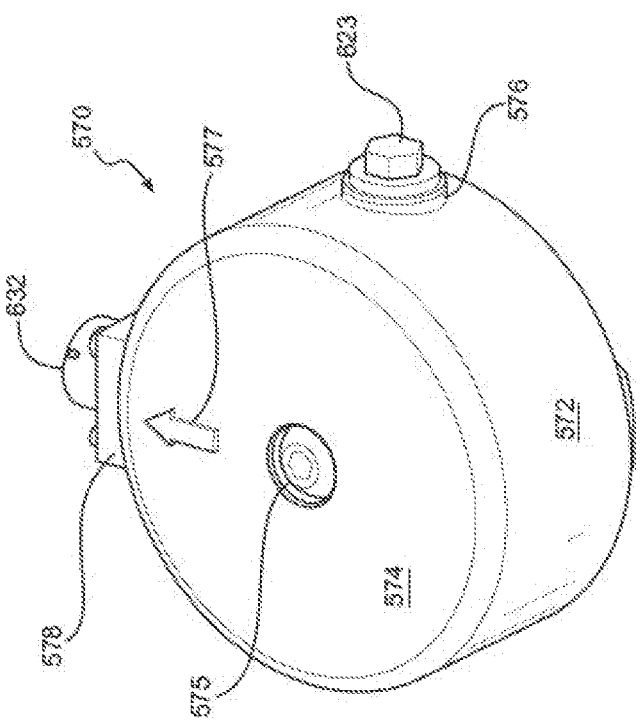
FIG. 28 is a perspective view of the outer surfaces of the sensor module of FIG. 23.
Figure 30:
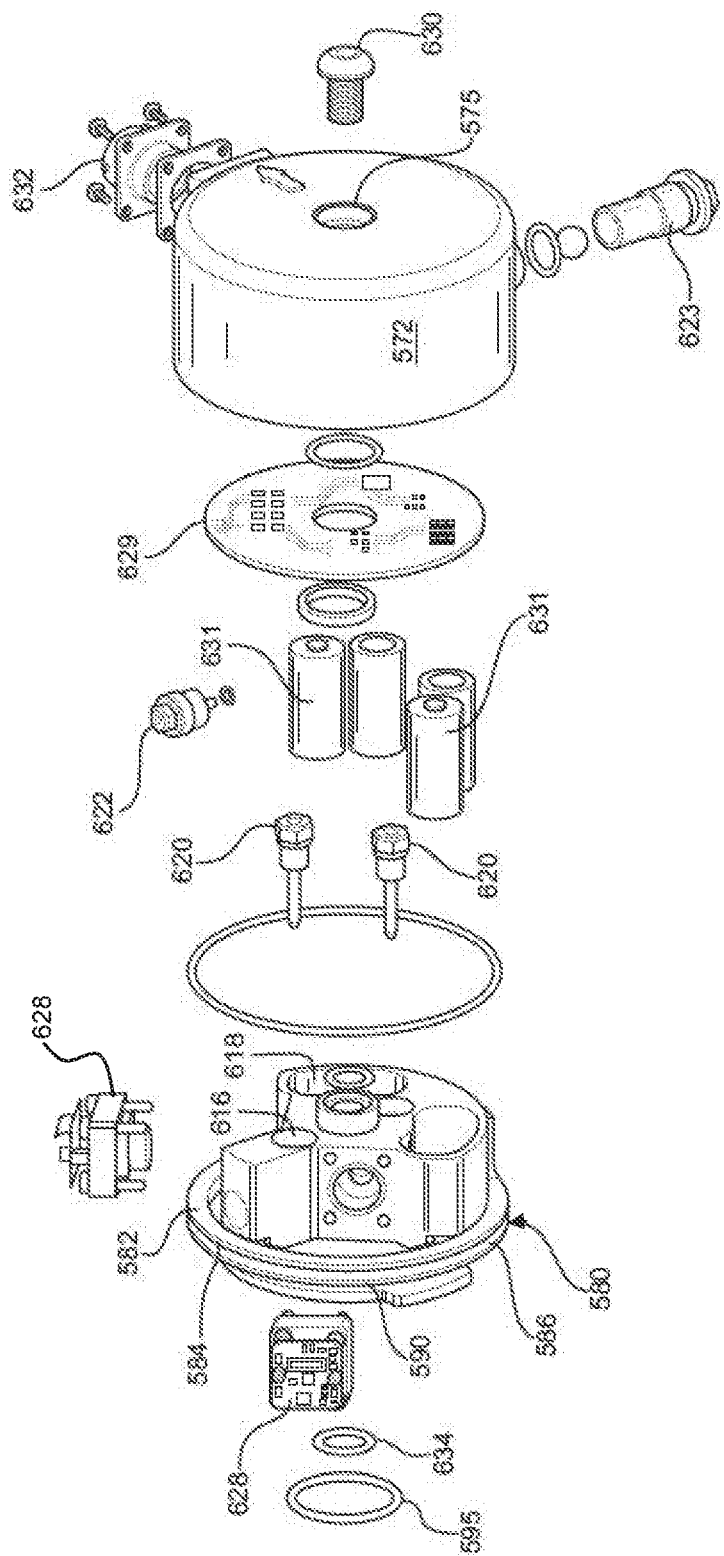
FIG. 30 is an exploded view of the sensor module of FIG. 28, illustrating the sensor module comprising a block and multiple sensors.

As shown in FIGS. 28 and 30, the sensor module 570 may comprise a shell 572 and a cap 580 mounted to the shell 572. The shell 572 may be generally cylindrical in shape. The outer diameter of the shell 572 is such that the shell 572 can be seated over and rotate over the core 522 of the bezel plate 520. The shell 572 comprises at one end a base panel 574 and is open at the opposing end. Two bosses 576, 578 project outwardly from the cylindrical sidewall of the shell 572. The boss 576 is round in shape, and the boss 578 is rectangular in shape. Each boss 576, 578 defines an opening into shell 572.

As shown in FIG. 30, the module cap 580 comprises a circular base plate 590. The base plate 590 is surrounded by a rim 582 that extends circumferentially around the plate 590. The rim 582 extends outwardly from the base plate 590 away from the surface of the plate that is directed toward valve 450. The rim 582 comprises a groove 584 that extends inwardly from the outer surface of the rim 582, and the groove 584 extends circumferentially around the rim 582.

Figures 31, 32A:
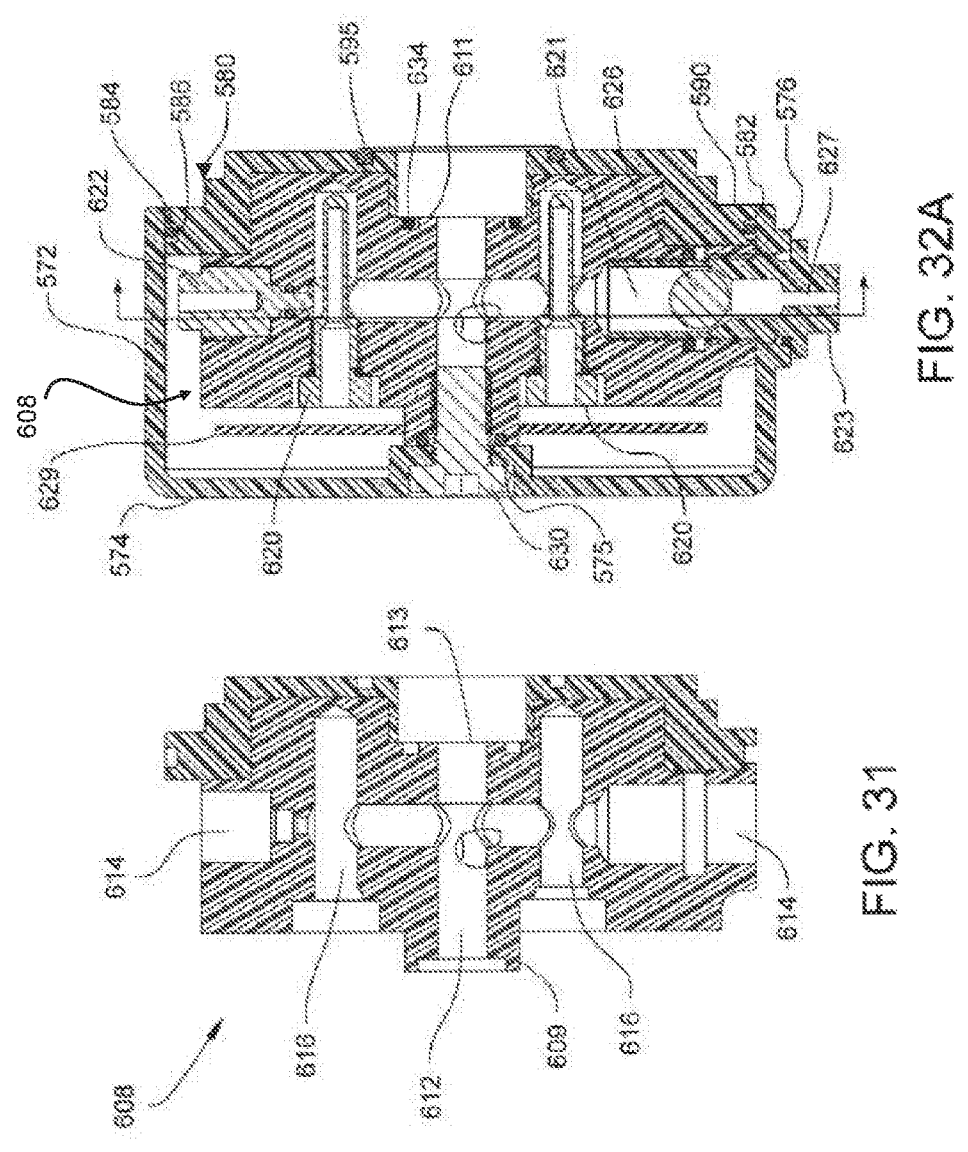

An O-ring 586 may be seated in groove 584 (see FIG. 32A). When the sensor module 570 is assembled, the cap rim 582 may be disposed adjacent the inner surface of the cylindrical wall of the shell 572. The O-ring 586 extends between the shell 572 and the cap 580 to provide a seal between these two components. Other configurations of the sensor module are also contemplated so long as the sensor module is able to sealingly enclose the electronic components and sensors so as to protect them from the sterilant agents while also permitting the sensors to measure the characteristics of the sterilant agent(s) and/or the interior of the container 50.

A pedestal 592 (see FIG. 29), also part of cap 580, extends outwardly from base plate 590 and toward the valve 450. Pedestal 592 may be circular in shape. The pedestal has a diameter that allows the pedestal to seat in and rotate in the center opening 524 internal to the bezel plate core 522. Forward of the pedestal 592, cap 580 has a circular face plate 594, which has a diameter slightly less than that of the pedestal 592. Two diametrically opposed tabs 596 and 598 are integral with and extend radially outwardly from the face plate 594. The tabs 596 and 598 subtend different arcs. Tab 596 is dimensioned to seat in notch 526 internal to the bezel plate 520. Tab 598 subtends an arc that does not allow the tab 598 to seat in notch 526 but will allow the tab 598 to seat in notch 528. Tabs 596, 598 and notches 526, 528 arranged as described provide a single orientation to the sensor module 570 when mounted to the body 432, such that one or more components of the sensor module 570 can be disposed in a specific configuration to perform their corresponding functions. In one example, as will be described below, the sensor module 570 includes a drain plug 623 (FIG. 32A), which is disposed at a lowermost location of the sensor module 570 when the sensor module 570 is mounted to the body 342, such that condensate within the sensor module 570 can flow away from sensors and other components toward the drain plug 623. However, the sensor module 570 can have other orientations when mounted to the body 432 and other components that perform corresponding functions based on the orientation of the sensor module.

Cap 580 is further formed so as to have an opening 602 in the center of the face plate 594. Opening 602 is non-circular in shape. More particularly, sleeve 604 has a shape that complements the shape of boss 484 that is integral with the valve plate 472. Opening 602 opens into the center void of the sleeve 604 formed integrally with cap 580. The sleeve 604 extends inwardly from the face plate 594. The components are arranged so that when the sensor module 570 is fitted to the container body 432, the boss 484 operatively snap-fits into opening 602 and seats in the sleeve 604.

While the specific exemplary embodiment as described above is directed to a configuration including the bezel plate removable coupling the sensor module 570 to the valve 450, it is contemplated that various other suitable devices and arrangements may be utilized to removably couple the sensor module 570 to the valve 450.

An O-ring 595 may be mounted to the cap face plate 594. The O-ring 595 is mounted in a groove that is spaced radially outwardly from and extends circumferentially around opening 602, (groove not identified). The O-ring 595 thus extends forward of plate 594 and extends around opening 602.

Referring to FIGS. 30-32A, a block 608 may be mounted to the inner face of the cap base plate 590. The block 608 is often formed from metal or a high temperature resistant thermoplastic able to repeatedly withstand the sterilization process conditions. The block 608, as seen in FIG. 31, is formed with a number of bores and voids. A bore 612 extends inwardly from the face of the block 608 located adjacent the cap 580. A counterbore 613 identified, extends around the section of bore 612 adjacent the cap 580. Counterbore 613 is positioned to receive sleeve 604 so that opening 602 opens into bore 612. In the illustrated example, bore 612 extends to the face of the block 608 spaced furthest from the cap 580. A raised boss 609 surrounds the open end of bore 612. The interior wall of block 608 that defines the section of bore 612 located inward of boss 609 may be threaded (threading not illustrated). The threading facilitates the engagement of a fastener 630, identified in FIG. 32A, in this section of bore 612. The fastener 630, which extends through the opening and counterbore 575 of the shell base panel 574, holds the shell to the block 608 and by extension, the cap 580. Not illustrated are the fasteners or other components that hold the block 608 to the cap.

A bore 614 intersects and extends perpendicularly to bore 612. Bore 614 is formed to have sections with different diameters, individual sections not identified. Two elongated voids 616 extend inwardly from the back face of block 608, the face of the block spaced furthest from cap 580. Each void 616 is centered on a longitudinal axis that is parallel to the longitudinal axis through bore 612. Each void 616 intersects bore 614. Each void 616 is formed with sections that have different diameters, individual sections not identified. The larger diameter sections of each void 616 are located adjacent the face of the block 608 spaced furthest from the cap 580.

Two additional voids, voids 618, one identified in FIG. 30, are also formed in the block. Voids 618 have longitudinal axes that are parallel to the longitudinal axis through bore 612. Each void 618 extends inwardly from the end of the block adjacent the shell base panel 574.

Figure 32B:
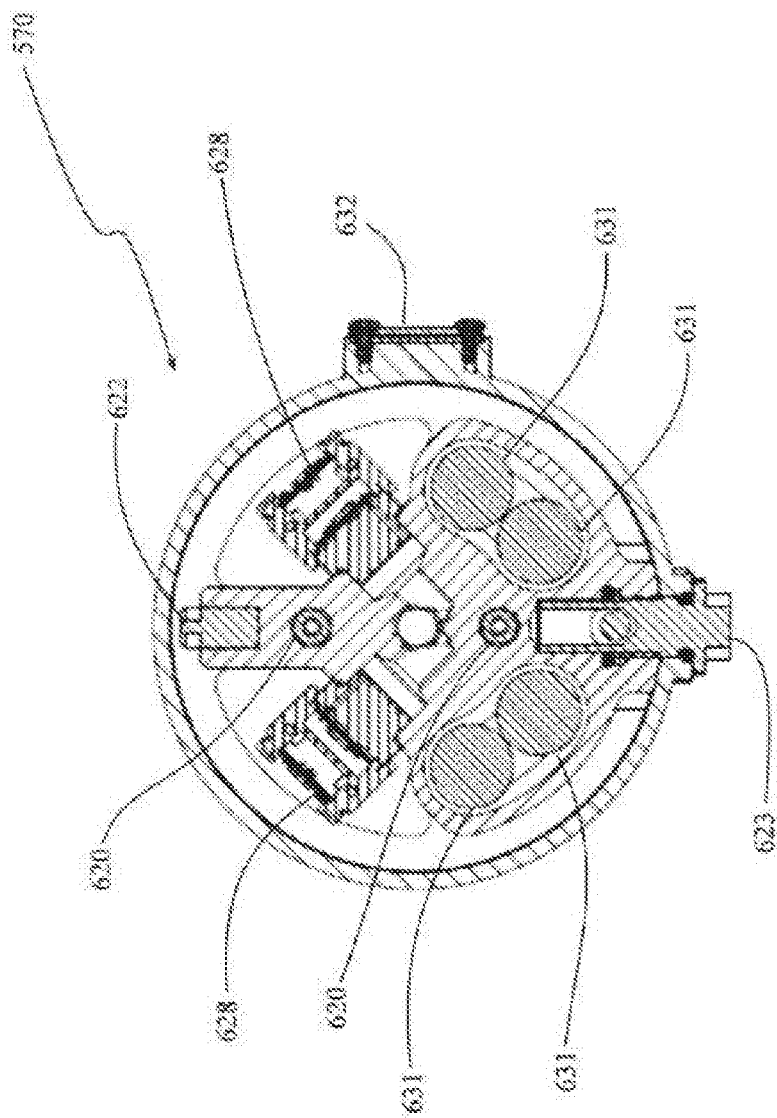
FIG. 32B is another cross-sectional view of the sensor module of FIG. 30, illustrating the drain plug in a lowermost portion of the sensor module when the sensor module is mounted to the container.

As mentioned above, the sensor module may include one or more sensors. In one potential implementation, the sensors are mounted to block 608 as seen in FIG. 32A. In the illustrated example, two temperature sensors 620 are mounted to the block 608. In the illustrated example, the temperature sensors 620 are substantially identical to the previously described temperature sensor 240 described with respect to FIGS. 5 and 8. Each temperature sensor 620 is mounted to the block so the elongated tube of the sensor 620 is fitted in the small diameter portion of one of the bores 614. Two pressure sensors 628 are also illustrated in FIGS. 30 and 32B. Pressure sensors 628 could measure gage pressure or absolute pressure, the latter being beneficial when using the measurement to accurately evaluate the steam saturation state. Pressure sensors 628 and temperature sensors 620 may be arranged so that condensate flows away from the same due to gravity so the sensors 620, 628 provide a more accurate reading that is not influenced by the amount of condensate on any corresponding one of pressure sensors 628 and temperature sensors 620. However, it is contemplated that the sensor module 570 can contain any one or more gas concentration sensors described above, such as the optical sensor assemblies 202, 202', 202", 202''', as described above, or any other sensor configured to measure characteristics within the container during the sterilization process, such as those described below.

Referring to FIGS. 30 and 32A, in one embodiment, the plug 622 is disposed within one of the open ends of bore 614 and is contained within the shell 572. The plug 622 is made from a metal to create a thermal mass and is configured to contain a temperature sensor (not shown). As shown in FIG. 32A, the plug 622 comprises a bore having an opening that faces the inner surface of the shell 572, and the bore is configured to receive the temperature sensor. The temperature sensor is configured to measure the rate of change of the temperature of the mass in order to determine the state of steam saturation of the sterilization process.

The opposite end of plug 622 may be sealed to stepped bore 614 and has a surface area for heat transfer from steam and gasses present in bores 612, 614, which are fluidly coupled to the inside of container during the sterilization process. A second plug 623 may be mounted to the opposite end of bore 614. The plug 623 is mounted to the sensor module 570 to project out of the boss 576. A plug 623 is configured to permit condensate to pass there through and be discharged from the sensor module 570. The plug 623 is formed to define a void 621 that is open to the bore 614. A float ball 626 is seated in the void 621. There is a small gap between the outer surface of ball 626 and the inner surface of the block 608 that defines the void 621, such condensate can flow around the ball as the ball floats upward along the void 621 axis and condensate flows out of the plug 622. A bore 627 extends from the base of the void 621 to the outer face of plug 623. Bore 627 has a diameter less than that of the ball. The float ball 626 is configured in a normally closed state due to gravity, such that air and gasses present in void 621 do not escape past the float ball 626. Float ball 626 functions to allow liquid condensate to lift the float ball 626 and allow condensate liquid to drain through bore 627. Alternative mechanisms to control condensate outflow from the sensor module may also be used.

In an alternate example, the thermal mass plug 622 can be located adjacent and above the condensate drain plug 623, below the lower sensor 620 with a surface area for heat transfer exposed within the stepped bore 614 between float valve drain plug 623 and sensor 620. In this example, the heat transfer rate to the thermal mass plug 622, as measured by the temperature sensor attached to the thermal mass, could aid in determining if there is a mixture of air or other gases with the steam sterilant present in the fluidly connected bores 612, 614 during the sterilization process. This alternate location could be advantageous in determining a more accurate steam saturation state of the sterilant present in the interior of the container 430 during the sterilization process.

A circuit board 629 may be also mounted to the block 608. Mounted to the circuit board are the below discussed components that control the operation of the sensor module 570 and that respond to the signals output by the temperature sensors 620, including the processor. Cells 631 may be disposed in the block 608 as seen in FIG. 30. In the illustrated example, two cells 631 are disposed in each void 618. The cells 631 provide the charge needed to power the electrically-actuated components internal to the sensor module 570. Cells 631 can include insulation, a phase change material, such as paraffin, urea, or other protective materials, so as to regulate heat transfer during the sterilization process and thus prevent overheating the cells 631 while they are operating within the container 430.

A terminal 632 is mounted to the boss 578 integral with the module shell 572. Terminal 632 performs the same function as the previously discussed terminal 132.

Referring to FIG. 32A, a number of O-rings are seen mounted in grooves formed in block 608. The majority of the O-rings and grooves are not identified. It is understood that these O-rings function as seals between the block 608 and the components mounted to the block 608 against which the O-rings are disposed. One O-ring that is identified is O-ring 634. The O-ring 634 sits in the step between counterbore 613 and bore 612. These O-rings create seals preventing sterilant gases from entering the cavities containing the electrical components of the sensor module 570.

Figure 33:
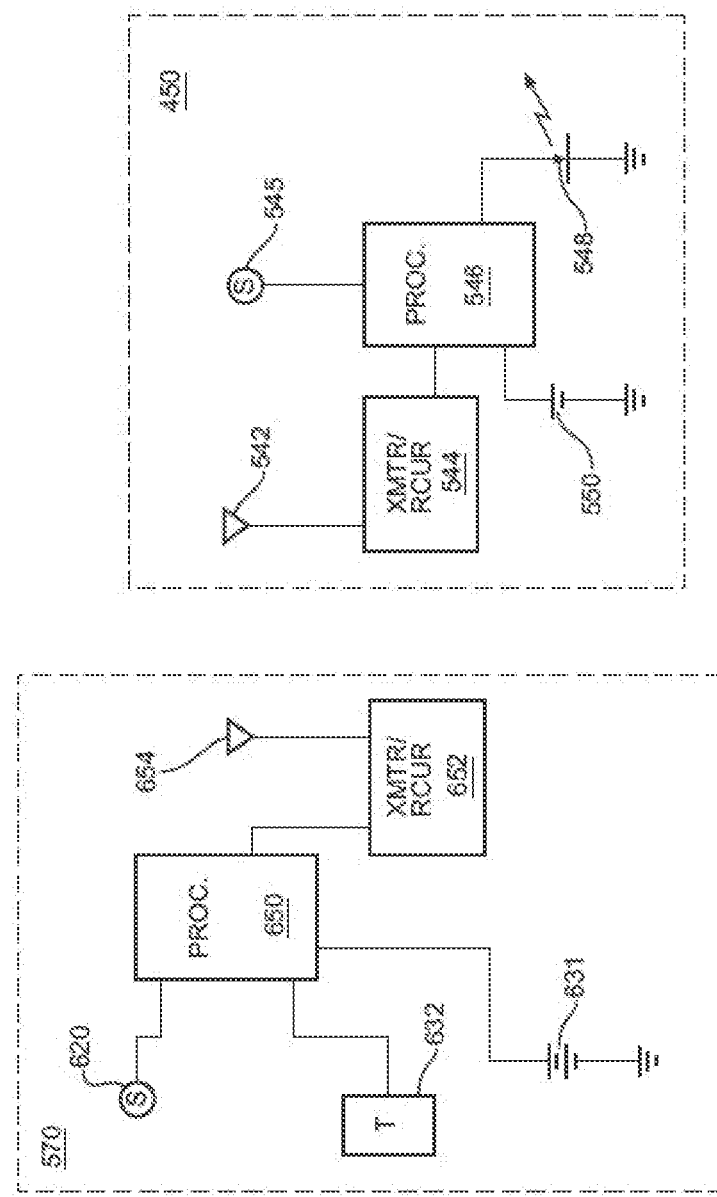
FIG. 33 is a block diagram of the complementary electrical components internal to the valve and sensor module of FIG. 23.

FIG. 33 is a block diagram of the electrical components mounted to both the valve 450 and the sensor module 570. The electrical components internal to the valve 450 are contained in a shell disposed below one of the wings 530 of the bezel plate 520 (shell not illustrated). It is understood that the shell is able to shield the components from the effects of the sterilization process to which container 430 is exposed.

One of the illustrated components is a communication device, shown as an antenna 542. Antenna 542 is able to broadcast signals to and receive signals from complementary antenna external from the valve 450. Antenna 542 is connected to a transmitter/receiver 544. The transmitter/receiver 544 converts received signals into digital signals. Transmitter/receiver 544 also formats digital signals into a form in which the signals can be broadcast by the antenna 542. A processor 546 is also mounted to the valve 450. Processor 546 receives the data signals from the transmitter/receiver 544 and transmits data to the transmitter/receiver. Not identified is the memory internal to the processor 546. Of course, other communication devices other than antennas may also be used to communicate from the processor 546, and the communication device may utilize any suitable communication protocol, such as RF, near-field, Bluetooth, cellular or Wi-Fi communication.

Another component that may optionally be connected to processor 546 is a lid sensor 545. Sensor 545 does not necessarily have to be disposed in the same shell in which the processor 546 is disposed. Sensor 545 monitors whether or not the lid 440 is attached to the body 432. In some examples, sensor 545 is a sensor sensitive to magnetic fields. One such sensor is a Hall Effect sensor. In these versions, a magnet (not illustrated) may be mounted to the lid 440. The magnet is mounted to the lid 440 so that when the lid 440 is mounted to the body 432 the magnet is in close proximity to sensor 545. Other types of lid sensors are also contemplated.

In the illustrated example described above, the notification device configured to communicate information to the HCP indicative of the sterilization state of the container 430 is an LED 548, i.e., whether acceptable sterilant agent(s) or sterilization process conditions have been achieved within the container. In some examples, the LED 548 is capable of emitting different colors of light and/or intermittently flash on and off depending on the sterilization state of the container. The LED 548 is mounted to the valve so the light emitted by the LED 548 is visible through the hole 536 in the bezel plate 520. A cell 550, only shown connected to the processor 546 also mounted to the valve, provides the power used to actuate the electrically actuated components of the valve 450. It is contemplated that the notification device can comprise any one or more of the notification devices described herein, or any other device configured to communicate the sterilization state of the container.

The sensor module 570 comprises a processor 650. The output signals generated by the sensors disposed therewith, such as temperature sensors 620, are applied to the processor 650. Processor 650 performs the same general functions as processor 384. Terminal 632 is also connected to the processor 650. It is contemplated the processor 650 can be configured to perform the same functions as the processor 546 to send signals to the same notification devices coupled to the valve 450 or similar notification devices coupled to other portions of the container 430 or otherwise used to communicate the sterilization state of the container 430.

Also shown internal to the sensor module can be a transmitter/receiver 652 and an antenna 654. The transmitter/receiver 652 responds to data and commands output by the processor by broadcasting appropriate signals over the antenna 654. Transmitter/receiver 652 receives from the antenna 654 the signals received over the antenna. The transmitter/receiver converts the received signals into a form in which the signals can be processed by processor 650. It should thus be appreciated that processors 546 and 650 are able to communicate wirelessly over antennae 542 and 654. Of course, other communication devices other than antennas may also be used to communicate from the processor 546, and the communication device may utilize any suitable communication protocol, such as RF, near-field, Bluetooth, cellular or Wi-Fi communication.

Terminal 632 is shown connected to the processor 650. Cells 631 are shown connected to the processor. This connection represents that the cells 631 power the chargeconsuming components internal to the sensor module 570 and cells can be optionally re-charged through terminal 632.

Figure 34C:
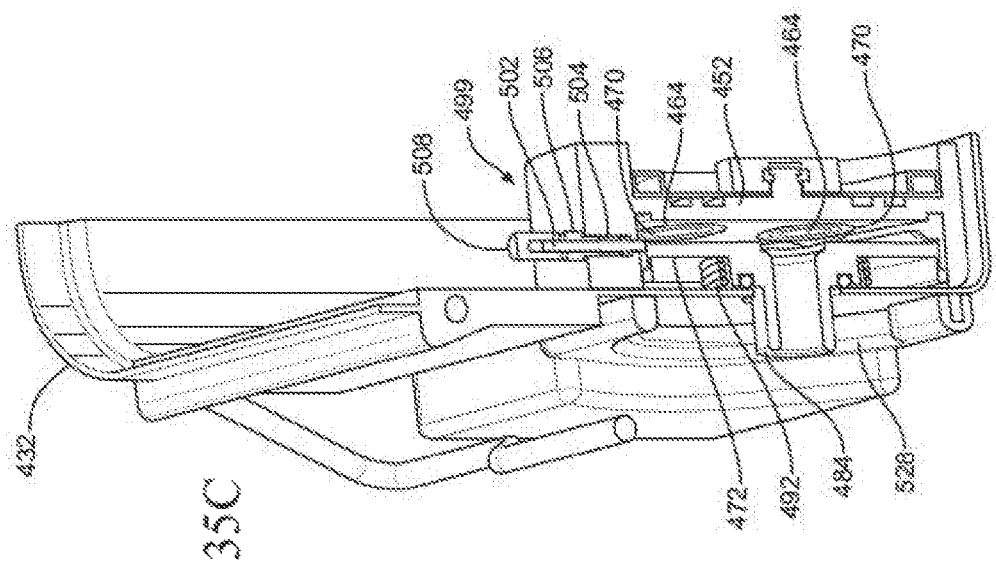
FIG. 34C is a perspective cross-sectional view of the container having the valve of FIGS. 34A and 34B in the closed state.

Referring to FIGS. 34A-34C, when the sterilization container 430 is initially prepared for use, the sensor module 570 is typically not attached to the container 430 and the valve 450 is in the closed and locked state. When the valve 450 is in the closed state, the valve plate 472 is typically in a rotational orientation relative to the valve cap 452, so that each of the indentations 488 associated with the valve plate 472 is disposed over one of the ribs 458 associated with the cap 452. As a result of the biasing force imposed by the wave washer 492 or other biasing device, the valve plate 472 is urged toward the valve cap 452 so that each rib 458 seats in the adjacent indentation 488 as seen in FIG. 34A. When the valve plate 472 is in this orientation, the plate channels 480 are not in registration with the holes 464. The base 474 of the valve plate 472 presses against the O-rings 470, which are located around the holes 464 of the valve cap 452 as seen in FIG. 34B. The O-rings 470 thus form seals between the valve cap 452 and valve plate 472, thus preventing the holes 464 of the valve cap 452 from fluidly communicating with the channels 480 and the bore 486 of the valve plate 472. The valve 450 is thus in a closed state. Other sealing members other than the aforementioned O-rings are also contemplated in alternative constructions.

Figure 35C:
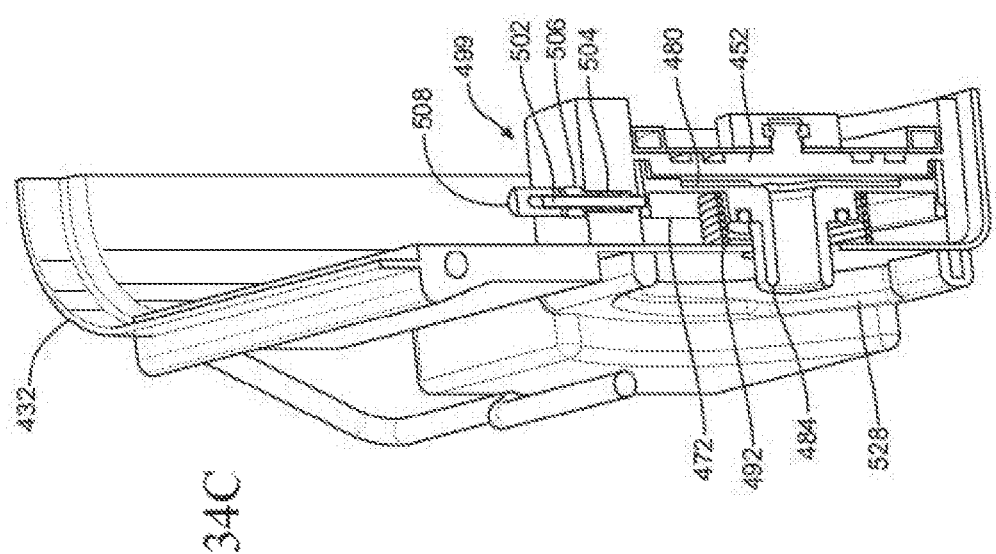
FIG. 35C is a perspective cross-sectional view of the container having the valve of FIGS. 35A and 35B in the open state.

Referring to FIGS. 35A-35C, the valve plate 472 provides clearance around the O-rings 470, or other sealing members, when the valve 450 is in the open state, such that a substantial portion of the O-rings 470 that interface with the valve 450 are exposed to the penetrating sterilant gases for sterilizing the O-rings, and the O-rings 470 can also wipe sterilant agent(s) onto a surface of the valve plate 472 when the valve 450 is moved from the open state to the closed state. Put another way, a significant portion of valve seal surfaces are exposed to sterilant gas by translating the valve plate 472 away from the valve cap 432. Rotating alone could allow contaminants residing outside the seal contact area during sterilization to survive the sterilization process, and the surviving contaminant could be smeared between the sealing surfaces during only rotational closing of the valve plate thus potentially contaminating the container interior surfaces, which may compromise the sterility of the instruments included in the interior of the container. However, with reference to FIG. 25, it is contemplated that other examples of the valve plate 472 may not be configured to provide a clearance for the O-rings 470 to expose a larger portion of them to the sterilant chemicals.

In one embodiment, when the valve 450 is in the closed state, the pin 502 is received in one of the indentations 490 in the valve plate 472. The presence of the pin 502 in one of the indentations 490 blocks the rotation of the valve plate 472 from the closed state to the open state. One or more instruments 60 are then placed in the interior of the container body 432.

The sensor module 570 is mounted to the valve 450, with the sensor module being a drive element moving between two positions and the valve 450 being a driven element movable between the closed and open states in response to the sensor module being moved between the two positions. In this example, the sensor module 570 is mounted to the valve 450 so as to transfer torque from the sensor module 570 to the valve 450, such that the sensor module 570 and the valve plate 472 rotate in synchronization with one another.

Figure 29:
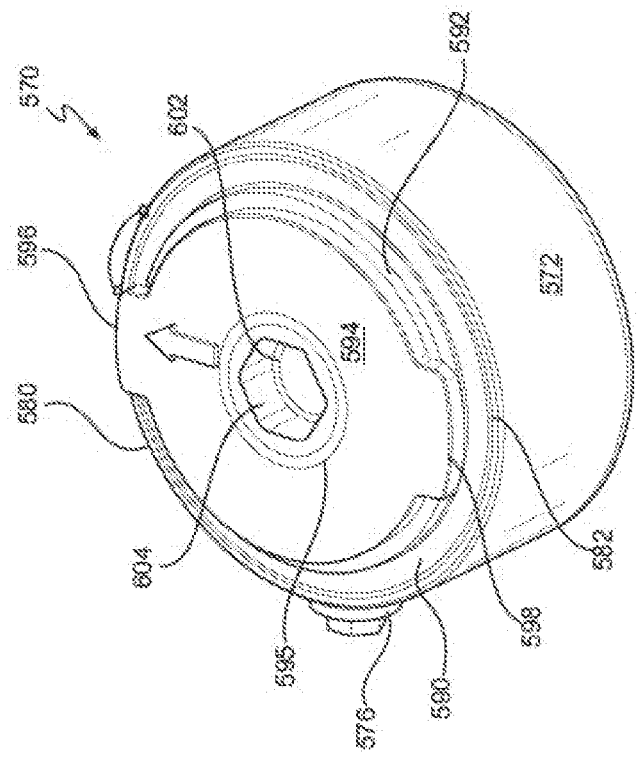
FIG. 29 is a perspective view of the inner face of the sensor module of FIG. 23.

Referring to FIGS. 23, 26 and 29, the sensor module 570 is aligned in a rotational position with respect to the bezel plate 520, such that the tabs 596, 598 (FIG. 29) are received through a corresponding one of the notches 526, 528 (FIG. 26) of the bezel plate 520, and the hexagonal boss 484 (See FIG. 23) of the valve plate 472 is received in the hexagonal bore 604 (See FIG. 29) of the sensor module 570. However, it is contemplated that the bore of the sensor module and the boss of the valve plate can have other suitable non-circular male and female connector configurations to permit the sensor module 570 to drive or rotate the valve 450. As but one example, the boss of the valve plate can have splines that mesh with corresponding grooves formed within an inner diameter surface of the sleeve of the valve plate. As still a further example, the boss of the valve plate can have a keyway that meshes with corresponding a key seat formed in the sleeve of the valve plate.

Once the sensor module 570 is rotatably mounted to the valve 450, the valve 450 can be moved from the closed state to the open state only when the valve locking assembly 499 is accessed from within the interior of the container 430 to disengage the valve plate 472 from a stationary container structure, such as the valve cap 452. In one example, the container 430 includes the lid 440 and the body 432, and the valve locking assembly 499 can be accessed only when the lid 440 has been removed from the body 432. Thus, the valve locking assembly 499, once engaged, may not be accessed until the sterility of the container has already been compromised.

More specifically, in this example, the valve locking assembly 499 may be operated by applying an upward force to the head 508 of pin 502, which in turn retracts the pin 502 from the indentation 490 in which the pin 502 is seated. This movement of the pin 502 away from the valve plate 472 allows the valve plate 472 to rotate from the closed state to the open state by rotating the sensor module 570 from its first position to its second position. Of course, other configurations of the valve locking assembly are contemplated other than pin mechanism described above.

The sensor module 570 is rotated from the closed state to the open state. In this example, this movement is made in the counterclockwise direction as viewed from the perspective of the interior of the container or in the clockwise direction as viewed from the perspective external to the container, until the module icon 577 aligns with the valve icon 538 on the bezel plate 520 and the valve 450 is positioned in the open state. At least one optional rotation stop 579 (one shown in FIG. 26) can extend from the plate core 522 toward the container exterior panel and positioned to engage tabs 596 and/or 598 to provide a physical rotation stop when module icon 577 aligns with valve icon 538 and the valve 450 is positioned in the open state. When the sensor module 570 is in this rotational orientation relative to the bezel plate 520, tabs 596 and 598 are disposed under the plate core 522. This positioning of the tabs 596 and 598 relative to the bezel plate 520 serves to releasably hold the sensor module to container 430.

In the described version, when the sensor module 570 is so aligned to the container, plug 623 is, by reference to the gravity plane, located at the bottom of block 608. This configuration positions the float ball 626 to allow liquid to drain from plug 623 as described earlier.

As a result of the rotation of the valve plate 472, the sections of the valve plate 472 that define indentations 488 rotate away from the ribs 458, and the valve plate 472 is displaced away from the adjacent inner face of the valve cap 452. This longitudinal displacement of the valve plate 472 is in opposition to a force placed on the valve plate 472 by the wave washer 492. The wave washer 492 is selected so all that is required to overcome the force of the washer is the manual force needed to rotate the valve plate 472. As a result of the displacement of the valve plate 472, the valve plate 472 rotates to an orientation in which each one of the cap holes 464 is in registration with one of the channels 480, and the O-ring 470 is not in contact with base 474. A fluid communication path thus exists from the void internal to the container body 432 through the holes 464, the channels 480, and bore 486 into the sensor module bore 612. The valve 450 is thus in the open state.

As a result of the sensor module 570 being locked to the valve 450, O-ring 595 is compressed between the valve plate 472 and the module cap 580. The O-ring 595 thus forms a barrier that surrounds the fluid communication path between the void internal to the container body 432 and the sensor module bore 612.

Also, once the sensor module 570 is mounted to the sterilization container the processor 546 may provide data to the processor 650, as illustrated in FIG. 33. These data describe the sterilization process conditions within the container 430.

Assuming a filter medium 410 is mounted to the lid 440, the lid is sealed over the open end of the body 432 of the container 430. Once the container 430 is in this state, the container 430 is ready to be placed in the sterilizer device.

Container 430 and the contents are subjected to the same sterilization process to which a conventional container is subjected.

During the sterilization process the sterilant gases and vapors that flow into the container void space flow through the valve 450 into the bores 612 and 614 internal to the sterilization module 570. The sensors within the sensor module, such as temperature sensors 620, are therefore able to measure the characteristics of the environment internal to the container 430.

In the illustrated example, container 430 is designed to hold instruments that are subjected to steam sterilization or other sterilization gas. The water vapor (steam) in the bores 612 and 614 may condense. This water will, owing to gravity, flow toward plug 623. The water will cause ball 626 to float. As a result of the ball floating, a sizable fraction of the water will flow out of the plug 623 through bore 627.

Referring to FIGS. 30 and 32A, based on the signals from the various sensors mounted within the sensor module 570, the processor 650, determines whether or not the instruments have been subjected to threshold process conditions that ensure a desired level of sterilization. As one example, the processor 650 can compare the measured characteristics from the sensors to data in a lookup table for threshold process conditions that ensure a desired level of sterilization. As shown in FIG. 33, the processor 650 informs the processor 546 of the results of this evaluation. If the evaluation is positive, the processor 546 actuates the notification device to communicate the status of the container 430 and instruments as being decontaminated to the desired level of sterilization. In this example, notification device comprises the LED 548, and the processor 546 actuates the LED 548 to emit a first color of light. If the evaluation is negative, the processor 546 actuates the LED 548 to emit a second color of light. The color light that is seen from the LED 548 thus provides an indication regarding whether or not the instruments 60 in the container have been subjected to threshold process conditions that would ensure a desired level of sterilization.

Once sterilization process has been completed and it is determined that the instruments have been exposed to threshold process conditions that ensure that the desired level of sterilization has been achieved, the sensor module 570 can be removed from the container 430, and the valve locking assembly 499 can prevent a contaminated sensor module from being attached to the container 430 and fluidly communicating with the interior of the container and the sterilized instruments therein. This step may be performed by first rotating the sensor module 570 counterclockwise from its second position to its first position, which in turn rotates the valve plate 472 counterclockwise from the open state to the closed state, such that the tabs 596, 598 (FIG. 29) of the sensor module 570 are aligned with the notches 526, 528 (FIG. 27) of the bezel plate 520 and the sensor module 570 can be removed from the valve plate. Of particular interest, because the valve plate 472 has been returned to the closed state, the indentation 490 is aligned with the bore 468 of the valve cap 452, such that the valve locking assembly 499 is actuated. In this example, the spring 504 moves a portion of the pin 502 into the indentation 490 and the valve locking assembly 499 engages the valve plate 472 to prevent the valve plate 472 from being rotated from the closed state to the open state, which is movement in a counterclockwise direction from the perspective within the interior of the container or in a clockwise direction from the perspective external to the container. In this respect, after the sensor module 570 has been removed from the valve 450, a contaminated sensor module may be mounted to the valve 450, but the valve locking assembly 499 prevents the valve plate 472 from being moved from the closed state to the open state, which in turn prevents the contaminated sensor module from fluidly communicating with the interior of the container and the sterilized surgical instruments contained therein. Again, as described above, the valve locking assembly 499 is accessible only from within the interior of the container 430 to disengage the valve locking assembly 499 from the valve plate 472 and permit the valve plate 472 to rotate from the closed state to the open state when the lid 440 is removed from the body 432.

More particularly, the valve plate 472 rotates so the indentations 488 are again placed in registration with the ribs 458. The wave washer 492 releases the potential energy stored in the washer. This potential energy pushes the plate base 474 back against the O-rings 470. The valve 450 is thus back in the closed state. Only when the valve 450 is so positioned are tabs 596 and 598 in registration with, respectively, the bezel plate notches 526 and 528. Only when the tabs 596 and 598 are in this rotational orientation is it possible to remove the sensor module 570 from the container 430. Thus, this version is constructed so that only after the valve 450 returns to the closed state is it possible to remove the sensor module 570 from the container 430.

After the sensor module 570 is removed from the sterilization container 430, the processor 546 continues to actuate the notification device to communicate the status of the container 430 and/or instruments therein. Continuing with the previous example, the notification device is the LED 548 configured to emit light indicating that the desired level of sterilization has been achieved for the instruments 60 in the container 430. Thus, the HCP wanting access to a set of instruments 60 that have been sterilized does not have to look for a container with sensor module attached. The HCP only needs to look for a container 430 with a notification device that is activated, such as LED 548 that is emitting light to indicate that the desired level of sterilization has been achieved for the instruments 60 in the container.

Also as a result of the rotation of the valve plate 472 back to the closed state, one of the indentations is rotated back into registration with pin 502. Spring 504 pushes the pin 502 back into the indentation 490. Thus the valve 450 returns to the locked state. This eliminates the likelihood that contact with the exposed sections of valve plate 472 and boss 484 could result in the inadvertent opening of the valve 450.

When it is time to use the instruments 60 in the container 430, the lid 440 is removed. Sensor 545 asserts a signal to the processor 546 indicating that the lid has been removed. In response to receipt of this signal, the processor 546 resets the notification device, such as LED 548 so the LED no longer asserts a signal indicating that the instruments in the container are sterile due to this breach in the sterile barrier formed by the container system.

A benefit of this version is that once a first sterilization container 430 and its contents have been sterilized, the sensor module 570 can be removed without contaminating the interior of the container. By examining the notification device, the HCP can determine the sterilization state of the container 430. Still continuing with the previous example, the notification device comprises the LED 548, and the HCP observes the light emitted from the LED 548 associated with the first container to indicate that the desired level of sterilization has been achieved for the instruments in the container 430. The sensor module 570 can then be attached to a second sterilization container that has not yet been subjected to the sterilization process, such that the sensor module 570 can be used to determine whether the desired level of sterilization has been achieved for instruments within the second sterilization container. This eliminates the need to provide each sterilization container with its own sensor module 570. In other words, the sterilization containers can be stored with their contents remaining in a sterilized state, with the sensor module being removed therefore.

FIGS. 36A-36E and 37 illustrate an alternative valve 450a that can be attached to a sterilization container 430. The valve 450a is substantially identical to the valve 450 shown in FIGS. 23-25. The most significant difference between the two valves is that valve 450a is configured to releasably hold a filter 676.

The valve 450a includes a valve cap 452a substantially identical to the valve cap 452 shown in FIGS. 23-25. The valve cap 452a is formed to have a rim 460a, which is similar to rim 460 because it extends outwardly from the inner face 454a of the valve cap 452a. Rim 460a also extends outwardly from the outer face 454b of the valve cap 452a, the face of the plate directed to the void space internal to the container body 432. The valve cap 452a also contains a post 672, which extends outwardly from the outer face of the valve cap 452a. This post 672 extends outwardly from the center of the valve cap 452a, and the post 672 is similar in structure and function to the post 82 of FIGS. 10A and 10E.

The filter 676 is shaped to seat over the outer face of the valve cap 452a and within the rim 460a. The filter 676 is formed with an opening (not identified) for receiving post 672. A filter frame 680 similar in function, though smaller in size than filter frame 320, is disposed over the outwardly directed surface of the filter. Filter frame 680 is dimensioned to seat within rim 460a and seat against filter 676. The filter frame 680 is releasably secured to post 672.

It should be understood that the version described by reference to FIGS. 36A and 37 is primarily for use when the presence of filter 676 will not appreciably affect the ability of the sensors internal to module 570 to measure characteristics within the container 430. For example, the concentration of a sterilant gas may be reduced as the sterilant gas flows through the filter 676. If an accurate measurement of the concentration of this sterilant gas inside the container 430 is required, the container should include the first described valve 450 of FIG. 23. This is because this valve 450 does not, when open, provide any barriers to the flow of the sterilant gas from the container void space to the module sensors.

FIGS. 36A-36E and 37 further illustrate an alternative valve locking assembly 499a, which is similar to the valve locking assembly 499 of FIG. 23 and includes similar components identified by the same reference numbers followed by the suffix "a". While the valve locking assembly 499 of FIG. 23 is generally operable to block the rotation of the valve plate 472 in one direction and allow rotation in the opposite direction, the valve locking assembly 499a is generally operable to block the rotation of the valve plate 472a in both the clockwise direction and the counterclockwise direction. More specifically, while the valve plate 472 of FIG. 23 has eight indentations 490 and each indentation 490 includes a wall or ramp portion that permits the pin 502 to slide along the ramp and out of the indentation 490, the valve plate 472a includes four bores 490a and none of the bores 490a include the ramp. Rather, each bore 490a includes opposing walls that extend radially inward and perpendicularly from a tangent of the rim 476a of the valve plate 472a, such that the pin 502 is configured to contact the walls and prohibit rotation of the valve plate 472a in any direction.

Figure 36B:
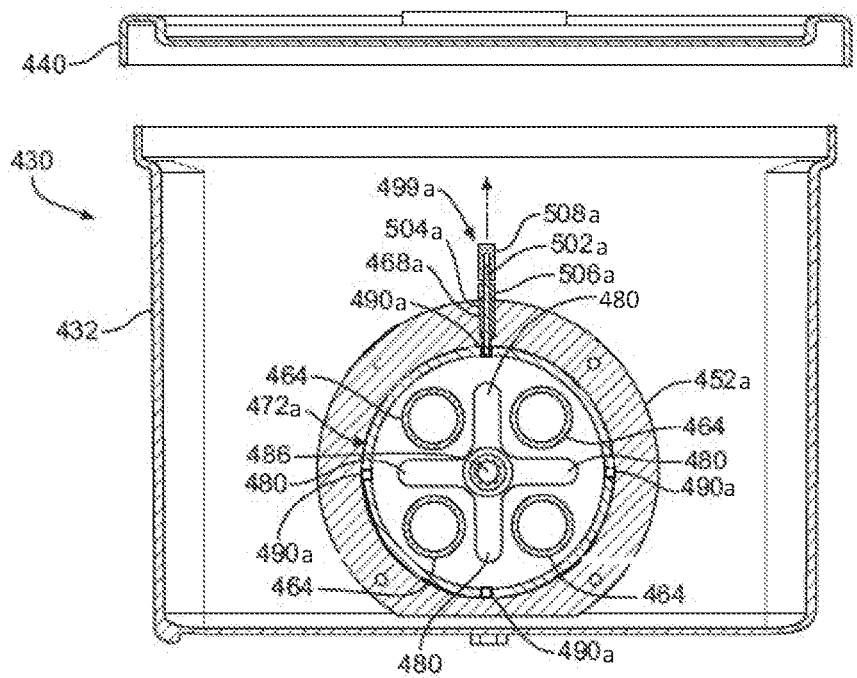
FIG. 36B is a cross-sectional view of the sterilization container of FIG. 36A, showing the normally closed valve positioned in a closed state with a valve locking assembly being accessed from within an interior of the container when the container is opened to permit the valve to rotate from the closed state to an open state.
Figure 36C:
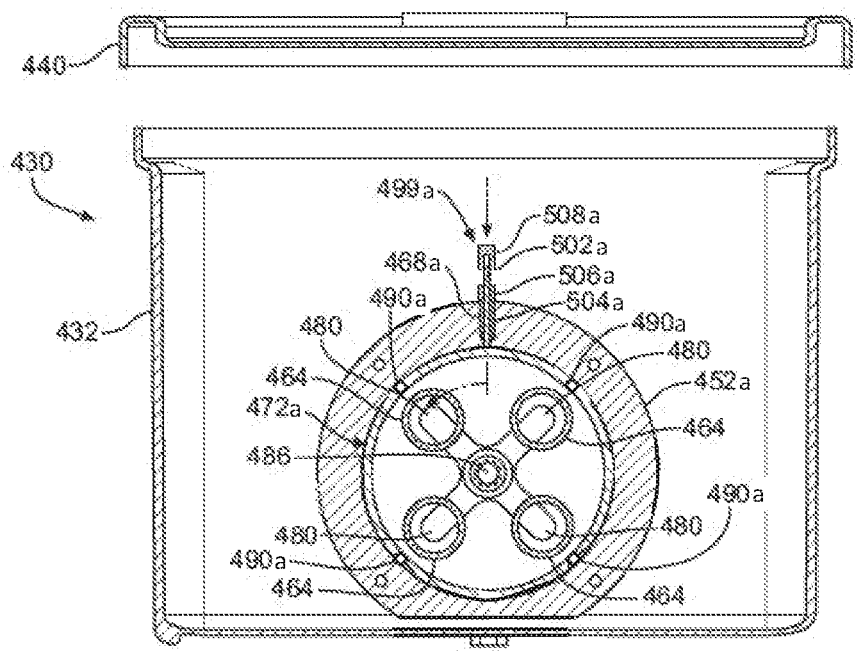
FIG. 36C is a cross-sectional view of the sterilization container of FIG. 36B, showing the valve being rotated from the closed state to the open state when container is opened and the valve locking assembly is accessed from within an interior of the container.

Referring to FIGS. 36B and 36C, once the sensor module 570 is mounted to the valve 450a, the valve 450a can be moved from the closed state to the open state only when the valve locking assembly 499a is accessed from within the interior of the container 430 to disengage the valve plate 472a from a stationary container structure, such as the valve cap 452a. In one example, the container 430 includes the lid 440 and the body 432, and the valve locking assembly 499a can be accessed only when the lid 440 has been removed from the body 432. Thus, the valve locking assembly 499a, once engaged, may not be accessed until the sterility of the container has already been compromised.

More specifically, as shown in FIG. 36B, the exemplary valve locking assembly 499a may be operated by applying an upward force to the head 508a of pin 502a, which in turn retracts the pin 502a from the bore 490a in which the pin 502a is seated. This movement of the pin 502a away from the valve plate 472a allows the valve plate 472a to rotate from the closed state to the open state (as shown in FIG. 36C) by rotating the sensor module 570 from its first position to its second position. Of course, other configurations of the valve locking assembly are contemplated other than pin mechanism described above.

Referring to FIG. 36C, the sensor module 570 has been rotated from the closed state to the open state by virtue of manually pulling the pin 502a out of the bore 490a and subsequently rotating the sensor module 570 from its first position to its second position. Once so rotated, the pin 502a is released and thereafter allowed to rest on an outer peripheral surface of the valve plate 472 until the valve plate 472a is moved back to the closed state as described further below, at which time the pin 502a rides along the outer peripheral surface until becoming again aligned with the bore 490a and accordingly biased back into the bore 490a to prevent both clockwise and counterclockwise movement. In this example, this movement is made in the counterclockwise direction as viewed from the perspective of the interior of the container or in the clockwise direction as viewed from the perspective external to the container, until the module icon 577 aligns with the valve icon 538 on the bezel plate 520 and the valve 450a is positioned in the open state. At least one optional rotation stop 579 (one shown in FIG. 26) can extend from the plate core 522 toward the container exterior panel and positioned to engage tabs 596 and/or 598 to provide a physical rotation stop when module icon 577 aligns with valve icon 538 and the valve 450a is positioned in the open state. When the sensor module 570 is in this rotational orientation relative to the bezel plate 520, tabs 596 and 598 are disposed under the plate core 522. This positioning of the tabs 596 and 598 relative to the bezel plate 520 serves to releasably hold the sensor module 570 to container 430.

Figure 36D:
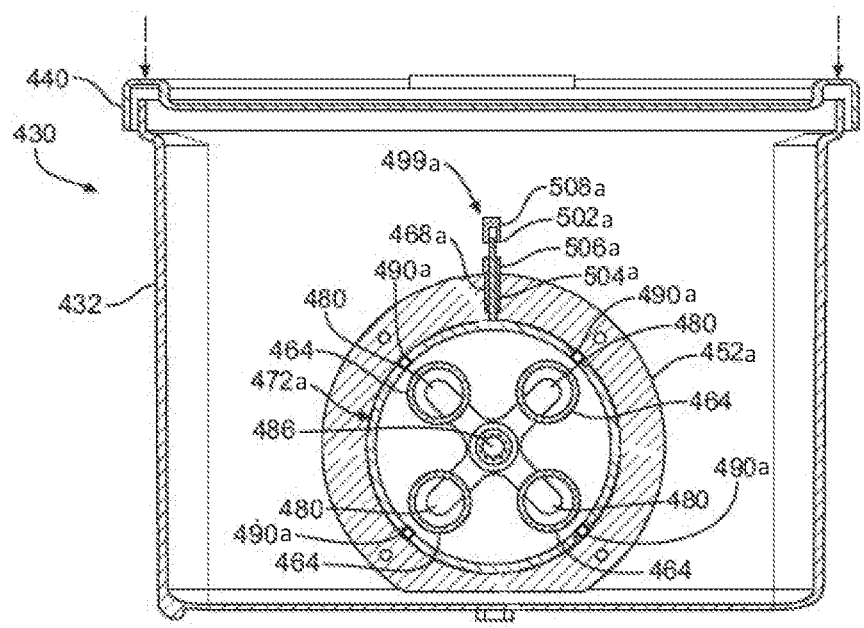
FIG. 36D is a cross-sectional view of the sterilization container of FIG. 36C, showing the valve positioned in the open state to permit the sensor module to fluidly communicate with the interior of the container when the container is closed.
Figure 36E:
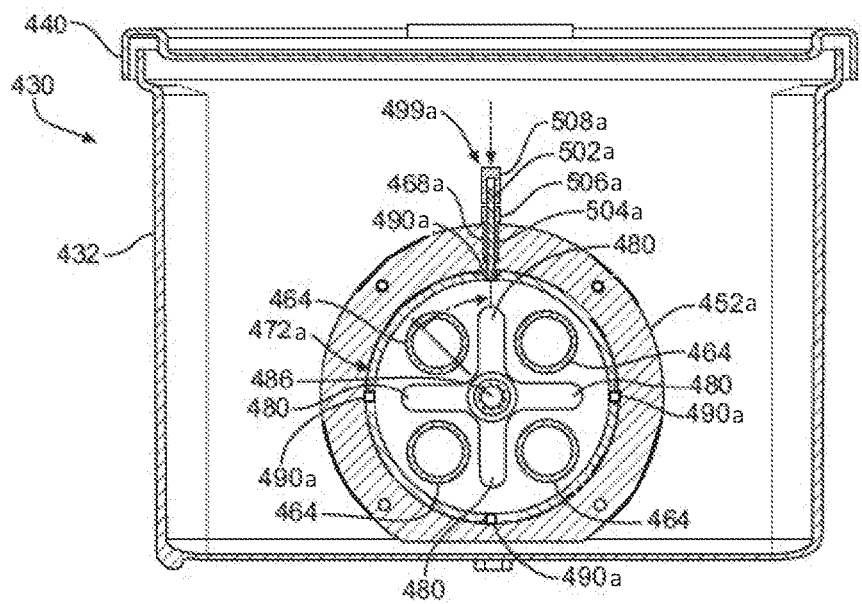
FIG. 36E is a cross-sectional view of the sterilization container of FIG. 36D, showing the valve rotated from the open state to the closed state, with the valve locking assembly preventing the valve from rotating to the open state and fluidly communicating a contaminated sensor module with the interior of the container without opening the container and accessing the valve locking assembly within the interior of the container.

Referring to FIGS. 36D and 36E, once the sterilization process has been completed and it is determined that the instruments have been exposed to threshold process conditions that ensure that the desired level of sterilization has been achieved, the sensor module 570 can be removed from the container 430, and the valve locking assembly 499a can prevent a contaminated sensor module from being attached to the container 430 and fluidly communicating with the interior of the container and the sterilized instruments therein. This step is performed by first rotating the sensor module 570 counterclockwise from its second position to its first position, which in turn rotates the valve plate 472a counterclockwise from the open state to the closed state, such that the tabs 596, 598 (FIG. 29) of the sensor module 570 are aligned with the notches 526, 528 (FIG. 27) of the bezel plate 520 and the sensor module 570 can be removed from the valve plate. Of particular interest, because the valve plate 472a has been returned to the closed state, the bore 490a of the valve plate 472a is aligned with the bore 468a of the valve cap 432, such that the pin 502a is received in both of the bores 490a, 468a in the locked position. In this example, the spring 504a moves a portion of the pin 502a into the bore 490a and the valve locking assembly 499a engages the valve plate 472a to prevent the valve plate 472a from being rotated in any direction. In this respect, after the sensor module 570 has been removed from the valve 450a, a contaminated sensor module may be mounted to the valve 450a, but the valve locking assembly 499a prevents the valve plate 472a from being moved from the closed state to the open state, which in turn prevents the contaminated sensor module from fluidly communicating with the interior of the container and the sterilized surgical instruments contained therein. Again, as described above, the valve locking assembly 499a is accessible only from within the interior of the container 430 to disengage the valve locking assembly 499a from the valve plate 472a and permit the valve plate 472a to rotate from the closed state to the open state when the lid 440 is removed from the body 432.

More particularly, the valve plate 472a rotates so the indentations 488 are again placed in registration with the ribs 458. The wave washer 492 releases the potential energy stored in the washer. This potential energy pushes the plate base 474 back against the O-rings 470. The valve 450a is thus back in the closed state. Only when the valve 450a is so positioned are tabs 596 and 598 in registration with, respectively, the bezel plate notches 526 and 528. Only when the tabs 596 and 598 are in this rotational orientation is it possible to remove the sensor module 570 from the container 430. Thus, this version is constructed so that only after the valve 450a returns to the closed state is it possible to remove the sensor module 570 from the container 430.

After the sensor module 570 is removed from the sterilization container 430, the processor 546 continues to actuate the notification device to communicate the status of the container 430 and/or instruments therein. Continuing with the previous example, the notification device is the LED 548 configured to emit light indicating that the desired level of sterilization has been achieved for the instruments 60 in the container 430. Thus, the HCP wanting access to a set of instruments 60 that have been sterilized does not have to look for a container with sensor module attached. The HCP only needs to look for a container 430 with a notification device that is activated, such as LED 548 that is emitting light to indicate that the desired level of sterilization has been achieved for the instruments 60 in the container.

When it is time to use the instruments 60 in the container 430, the lid 440 is removed. Sensor 545 asserts a signal to the processor 546 indicating that the lid has been removed. In response to receipt of this signal, the processor 546 resets the notification device, such as LED 548 so the LED no longer asserts a signal indicating that the instruments in the container are sterile due to this breach in the sterile barrier formed by the container system.

While the exemplary sensor modules described above are configured to measure characteristics within the interior of the container during a sterilization process, based on the concentrations of sterilant gases, temperature, and pressure within the container, another exemplary sensor module can determine whether the desired level of sterilization has been achieved based on a calculated steam saturation state in view of the temperature measurements of one or more thermal masses, the pressure measurements during the sterilization process, the length of the sterilization process, and/or any combination thereof. It is contemplated that one or more sensor modules can be used to determine sterilization process conditions within a container based on any combination of the concentrations of sterilant gases, temperature measurements, pressure measurements, the temperature measurements of one or more thermal masses, the pressure measurements during the sterilization process, and/or the length of the sterilization process.

One exemplary sensor module can be configured to measure characteristics within the interior of the container during a sterilization process and determine the steam saturation state based on the temperature of one or more thermal masses, the pressure during the sterilization process, the length of the sterilization process, and any combination thereof.

Pressures higher than atmospheric pressure are necessary to increase the temperature of the steam for destruction of micro-organisms that can be more difficult to kill. The saturated steam at a required temperature and time must penetrate and reach every surface of the items to be sterilized. When steam initially enters the container at a predetermined pressure, the steam condenses upon contact with comparably colder items, including the instruments within the container and internal surfaces of the container. This condensation releases heat, simultaneously heating and wetting surfaces exposed to the interior of the container. The instruments must be exposed to moist heat for a minimum time and at a minimum defined temperature in order to provide proper sterilization. For example, one type of instrument may require exposure to 100% saturated steam for 4 minutes at 270 degrees Fahrenheit to destroy the micro-organisms and another 20 minutes of evacuation to dry the instrument within the container so that condensation does not accumulate within the container. A minimum temperature-time and steam concentration relationship is required to be maintained as the threshold process conditions throughout all portions within the container and throughout the container to properly kill target micro-organisms and ensure that the desired level of sterilization has been achieved. The time, temperature, and steam concentration to destroy micro-organisms depend upon many characteristics measured within the container. For example, the size, surface area, thermal mass, orientations, and depths of internal cavities of the contents within the container as well as the steam penetration properties of the container can affect the efficiency of destroying micro-organisms. Ideal steam for sterilization is 100% saturated steam. Saturated steam (100% relative humidity) has a high heat content, and no water in the form of a fine mist is present within the saturated steam. The steam saturation state can be determined based on the rate of change in temperature of a known mass.

Figure 38A:
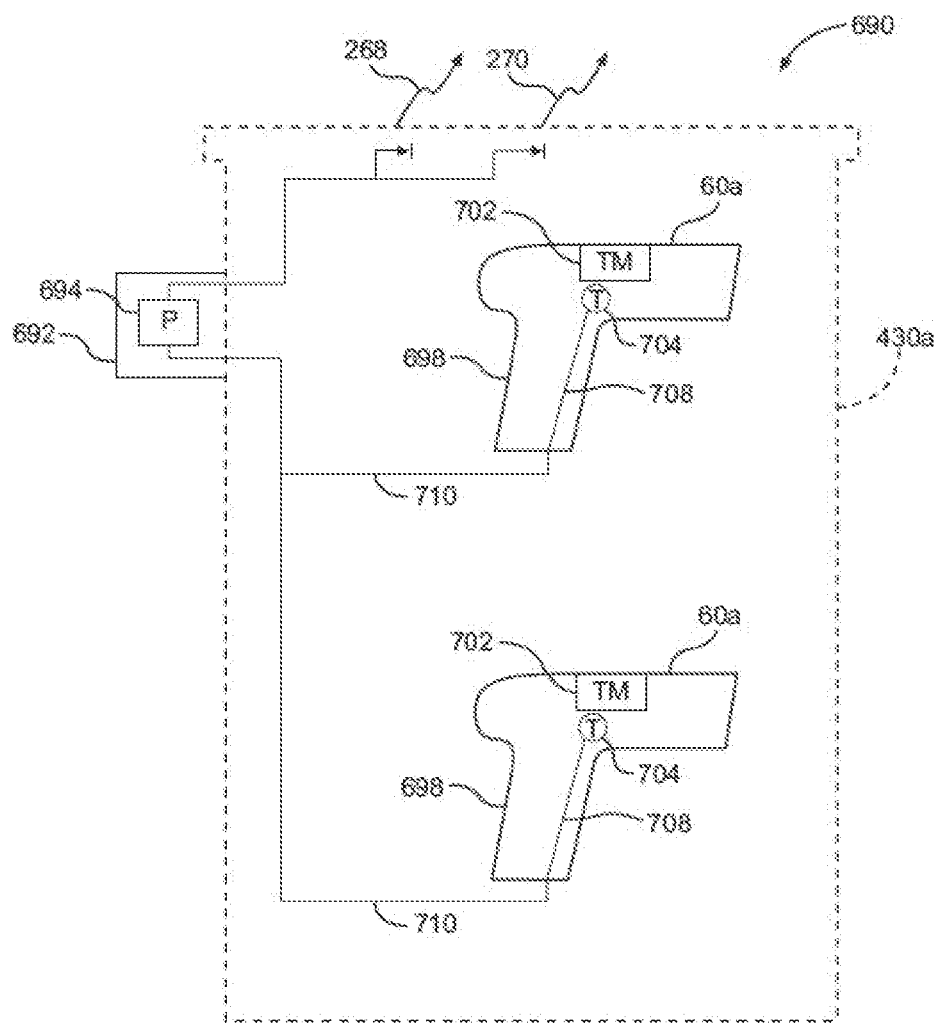
FIG. 38A is a block diagram of another example of a sterilization container and sensor module that comprises a series of sensors internal to corresponding instruments being disinfected to measure characteristics of the saturated steam to which the instruments are exposed.
Figure 36C:
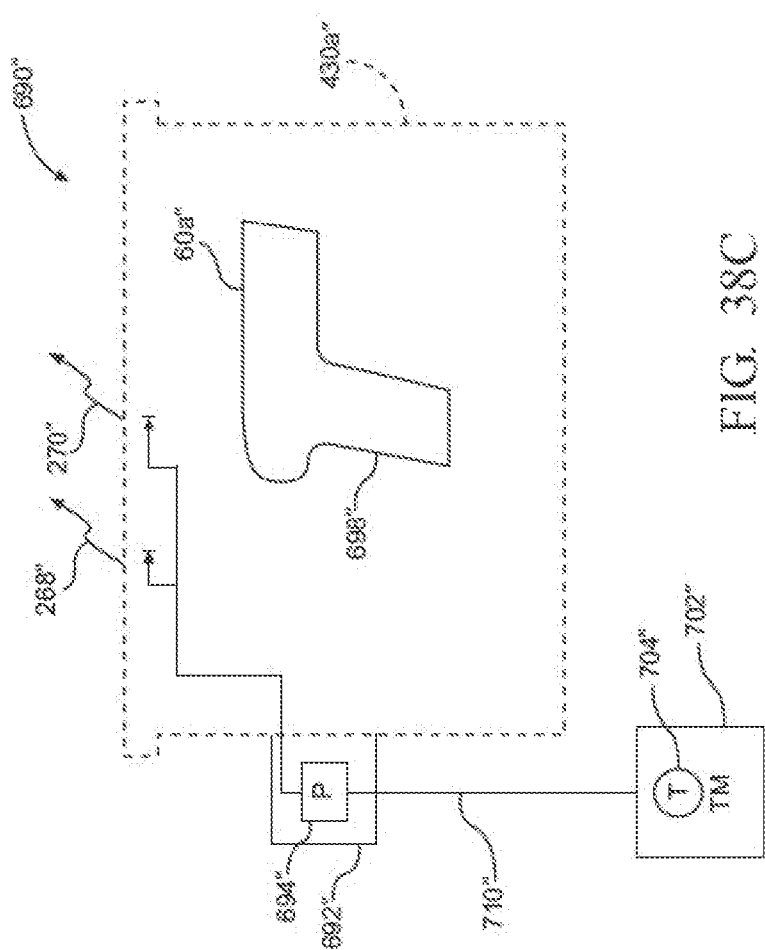

FIG. 38A depicts another exemplary sensor module 692 for measuring the characteristics within the container during the sterilization process. The measured characteristics include the temperature profile of multiple thermal masses within or outside of the container, the pressure within or outside of the interior of the container, the length of the sterilization process, or any combination thereof. While some of the prior described sensor modules comprise sensor assemblies configured to measure the concentration of sterilant gases, this sensor module 692 includes a sensor assembly 690 configured to measure a steam saturation state of the steam (water vapor) to which the instruments 60a are exposed. Saturated steam heat is one type of sterilant gas that can be used to destroy micro-organisms.

The sensor assembly 690 is configured to measure the steam saturation state within the interior of a container 430a similar to the previously described container 430 of FIGS. 21 and 22. More specifically, the sensor assembly 690 comprises one or more temperature sensors coupled to a corresponding one or more thermal masses that are disposed either within or outside of the container 430a.

Referring to the schematic example illustrated in FIG. 38A, the sensor assembly 690 can comprise multiple thermal masses 702, which in this form comprise at least a portion of multiple instruments 60a and each one of these instruments 60a can have a corresponding temperature sensor 704. More specifically, the sensor assembly 690 comprises a sensor module 692 that is removably mounted to an external surface of the container 430a. The module 692 has the same basic housing as the module 570. For reasons that are apparent below, there may not be any sensors in module 692. Module 692 can include a processor 694 similar to the processor 650. Each one of the thermal masses 702 can be located within at least a portion of the corresponding instruments 60a, and each thermal mass 702 comprises at least a portion of a body 698 of the instrument 60a. In some examples, the thermal mass is the body 698 of the instrument, and the temperature of no other thermal masses are monitored other than that of the instrument. Furthermore, the sensor assembly 690 can comprise one or more temperature sensors 704 disposed internal to the body 698 of a corresponding one of the instruments 60a.

The temperature sensor 704 may send a signal indicative of the temperature of the thermal masses 702 to the processor 694. This measured characteristic is useful because the temperature of the thermal mass, as well as the rate of change of the temperature of the thermal masses 702 over time, can be used to determine the state of the steam in the environment around the thermal masses 702. In particular, because the thermal mass 702 is part of the instrument 60a, the measurements from the temperature sensor 704 thus provide data regarding the nature of the steam environment to which the instrument 60a is exposed. For example, in some sterilization processes, for the process to be considered a validated process, the instrument needs to be in a saturated steam environment at a predetermined pressure for a predetermined amount of time. A saturated steam environment is one in which the majority of the gas in the chamber is water vapor (steam) with only trace amounts of the gases that normally make up air. Accordingly, based on the measurements from temperature sensor 704 and/or pressure sensor, the processor 694 determines whether or not the instrument 60a has been exposed to threshold process conditions that ensure that a desired level of sterilization has been achieved.

Based on the signals received from the temperature sensors 704 during the steam sterilization process, the processor 694 determines the rate of change in temperature of the thermal masses 702, the peak temperature of the thermal masses 702, the pressure within the container, or any combination thereof. The processor 694 can determine whether any one of these measurements meet empirically determined requirements indicative of sterilization process conditions by, for example, comparing the measurements to data stored in a reference lookup table or a suitable algorithm. Thus, by comparing, for example, the rate of change in temperature of the thermal mass 702 disposed within the instrument 60a with a known rate of change for the corresponding instrument which confirms the state of steam saturation, the processor 694 can determine whether the instruments have been properly sterilized. Similarly, by comparing the peak temperature of the thermal mass 702 with a known peak temperature which confirms validated state was achieved, the processor 694 can determine if the instruments 60a have been properly sterilized.

The temperature sensor 704 can send the signal to the processor 694 by wireless or wired transmission. In the example illustrated in FIG. 38A, the temperature sensor 704 sends the signal to the processor 694 over conductors 708, 710. In particular, the conductor 708 can extend from the sensor 704 through the handpiece body 698, and the other conductor 710 can be coupled to the former conductor 708 and be disposed within the container 430a. In other words, the conductor 710 extends from the instrument 60a to the module 692. Not illustrated are the terminals that connect conductor 708 to conductor 710 and that connect conductor 710 to module processor 694.

FIG. 38B depicts another exemplary sensor module 692' for measuring various characteristics within the container during the sterilization process, including the temperature attributes of the single largest thermal mass within or outside of the container, the pressure within or outside of the container, the length of the sterilization process, or any combination thereof. The sensor module 692' comprises multiple components, which are similar to those of the temperature sensor module 692 of FIG. 38A and are identified by the same reference numbers followed by a single prime symbol ('). However, while the sensor assembly 690 of FIG. 38A comprises multiple thermal masses 702 in the form of the separate instruments 60a including corresponding temperature sensors 704, the sensor assembly 690' comprises only the single largest thermal mass disposed within the container and one or more temperature sensors 704' coupled to the same. In other words, the only temperature sensors within the sterilization container are those coupled to the single largest thermal mass disposed within the container. In particular, the largest thermal mass can comprise the combination of the instrument 60a' and the rack 62 holding the instrument 60a'. The temperature sensor 704' can be a thermistor, which is coupled to the instrument 60a' and the rack 62 holding the instrument 60a'. By measuring the thermal mass of the largest thermal mass, it can be reasonably discerned that if the largest thermal mass has reached the threshold process conditions, the smaller thermal masses present in the container, i.e. smaller instruments, would have also reached the threshold process conditions.

Referring to FIG. 38C, still another exemplary sensor module 692" can comprise multiple components, which are similar to those of the temperature sensor module 692 of FIG. 38A and are identified by the same reference numbers followed by a double prime symbol ("). However, while the sensor assembly 690 of FIG. 38A comprises multiple thermal masses 702 and corresponding temperature sensors 704 within the container 430a, the sensor assembly 690" comprises only the single largest thermal mass 702" disposed outside of the container 430a" and one corresponding temperature sensor 704" coupled to the same. However, two or more temperature sensors can be coupled to one or more thermal masses disposed external to the container and within the sterilizer device.

Based on the signals received from any one or more of the temperature sensors 704" during the steam sterilization process, the processor 694" can determine the rate of change in temperature of the thermal mass, the peak temperature of the thermal mass, or any combination thereof. The processor 694" can determine whether any one or more of the measured characteristics meet or exceed the threshold process conditions by, for example, comparing the measurements to data stored in a lookup table. Thus, by comparing, for example, the rate of change in temperature of the thermal mass or other measured characteristic with a corresponding threshold process condition empirically determined to decontaminate the instruments to a desired level of sterilization, the processor 694" can determine whether the desired level of sterilization has been achieved. Similarly, by comparing the peak temperature of the thermal mass with a known peak temperature which confirms validated sterilization conditions, the processor 694" can determine if the instruments 60a" have been exposed to the threshold process conditions. Once the processor 694" has determined that the desired level of sterilization has been properly achieved, the processor 694" can send a signal to one or more notification devices to communicate the same. In some examples and instrument configurations, additional sensors like previously described absolute pressure sensors, sterilant concentration sensors, and sterilant/gas temperature sensors (not coupled to a thermal mass) may be added to the sensor assemblies 690, 690', and 690" to improve the data inputs to the processor which may improve the accuracy of measuring and determining the sterilization process conditions.

The temperature sensor can send the signal to the processor 694" by wireless or wired transmission. In the example illustrated in FIG. 38C, the temperature sensor 704" sends the signal to the processor 694" over conductor 710".

In addition to or in substitution of the electric gas concentration sensors, the temperature sensors, and/or the pressure sensors, other exemplary sensors can include one or more non-electric gas concentration sensors. Examples of the non-electric gas concentration sensors can include a biological indicator (BI) and/or a chemical indicator (CI), which can provide the combined functions of: (1) measuring concentrations of sterilant gases within the container; and/or (2) indicating or communicating the status of the instruments from a standpoint of desired sterile state. Alternatively, the BI and/or CI can cooperate with any one or more notification devices, as described below, such as LEDs, buttons, or other suitable notification devices, for communicating the status of the instruments.

The BI can comprise a collection of living spores resistant to the sterilant agent. A portion of these spores may be disposed in dry spore strips, discs in envelopes, sealed vials or ampoules, which are exposed to the sterilant gases. Another portion of the spores can be disposed in a control sample that is not exposed to the sterilant gases. The HCP and/or a scanning device, such as a camera, can analyze the BI, temperature, pressure, and/or elapsed time to determine the sterilization condition of the container.

The BI may be configured to determine whether the most resistant micro-organisms (e.g., *Geobacillus* or *Bacillus* species) are present rather than merely determine whether the physical and chemical conditions corresponding with the threshold process conditions necessary to ensure a desired level of sterilization are satisfied. Because the spores used in BIs can be more resistant and present in greater numbers than are the common microbial contaminants found on instruments, an inactivated BI can indicate that other less resistant pathogens on the instruments have also been killed.

The CI can comprise chemicals that are sensitive to the sterilant gases, temperature, and/or pressure to assess the environment within the container. One exemplary CI can comprise a heat-sensitive tape that is configured to change color rapidly when a given parameter is reached. Another exemplary CI can include a medium and an internal chemical indicator placed at a predetermined position within the medium to ensure that the sterilant gas has penetrated the medium and thus represent that the sterilant gases reached all portions of the instruments inside the container. Single-parameter internal CIs can provide information on only one sterilization parameter and are available for steam, dry heat, and/or unsaturated chemical vapor. Multi-parameter internal indicators can measure two or more parameters and can provide a more reliable indication that sterilization conditions have been satisfied. Examples of the CI can include: (1) tape, labels, and paper strips printed with an ink that changes color when exposed to one or more sterilization parameters; and/or (2) wicking paper having one end with an ink or chemical tablet that melts and wicks along the paper over time under desired process parameters. The wicking color from the ink or tablet can produce a color bar that reaches a predetermined "accept" area on the paper if proper sterilization parameters are satisfied.

As will be described below, one or more BIs and/or CIs can be: (1) disposed within the sterilization enclosure, such as the container; (2) removably coupled to an external surface of the enclosure but in fluid communication with the interior of the enclosure, (3) be exposed to sterilant gases propagating from the container through an airflow challenge cannula to the BI and/or CI; (4) be disposed within the sensor module described above. The BIs and CIs will be indicated collectively as a process indicator "PI". Thus, any reference to "PI" below should be interpreted to refer to the BI, the CI, or combinations thereof.

Referring to FIGS. 39 and 40, another example of the sensor module 570' comprises one or more PIs 57' and is removably coupled to an external surface of a container 430'. This sensor module 570' may comprise multiple components, which are substantially similar to the components of the sensor module 570 as shown in FIGS. 22, 23, and 30 and are identified by the same reference numbers as followed by a single prime symbol ('). However, while the sensor module 570 comprises two temperature sensors 620 received in corresponding voids 616, the present exemplary sensor module 570' can have one or more PIs 57' disposed behind one or more transparent windows 53 in the sensor module 570' (see FIG. 40). Accordingly, the HCP can read the PIs 57' through the transparent windows 53. It is of course contemplated that the sensor module 570 may include the transparent window. The shape and configuration of the transparent window is not particularly limited, so long as it is capable of withstanding the sterilization conditions within the sterilizer and maintaining the sterile environment within the sensor module when the sensor module is coupled to the sterilization container. The size and orientation of the window is not particularly limited.

Similar to the sensor module 570, the sensor module 570' can be aseptically and removably coupled to a normally closed valve 450' integrated in the container 430'. In particular, this container 430' may comprise the normally closed valve 450', which opens when the sensor module 570' is coupled to the container 430' prior to the sterilization process, such that the PI 57' is exposed to the steriliant gases in the container 430' during sterilization. In addition, the valve 450' closes in response to the sensor module 570' being removed from the container 430' after the sterilization process, so as to aseptically remove the sensor module 570' from the container 430' and prevent contaminants from entering the container 430' through the valve 450'.

FIG. 41 illustrates another example in which a trapdoor mechanism 750 is provided in substitution of the normally closed valve 450'. In particular, the trapdoor mechanism 750 is configured to expose the PI 57' to steriliant gases within the container when the sensor module 570' is coupled to the container 430'. More specifically, the trapdoor mechanism 750 can comprise a panel 436' defining an aperture 752 and a door 754, which is coupled to the panel 436' and configured to move to a closed position in order to sealingly close the aperture 752. The trapdoor mechanism 750 can further comprise a biasing member 756, such as a spring, configured to move the door 754 to the closed position. Moreover, the trapdoor mechanism 750 can also comprise a locking mechanism 758 configured to hold or lock the door 754 in the closed position. In particular, the locking mechanism 758 can comprise a latch 760, which is coupled to the panel 436' and movable to a latched position such that the latch 760 holds the door in the closed position, and the biasing member 756 that moves the latch to the latched position to sealingly close the door 754 when the sensor module 570' is removed from the container 430'. The locking mechanism 758 can further comprise a handle 762 disposed within the container 430' and configured to be accessible only from the interior, such that a removed or contaminated sensor module 570' cannot be re-inserted into or re-attached to the container 430'.

After the sterilization process has been completed, a HCP can analyze the PI to determine the characteristics of the PI and thus the characteristics of container during the sterilization to determine whether the instruments were exposed to threshold process conditions that would ensure a desired level of sterilization was achieved and communicate the same to the HCP. However, additional steps can be undertaken to utilize PIs for communication by other notification devices. In one example, the HCP can read the PI, determine the characteristics within the container based on the status of the PI, and manually record the characteristics on an external surface of the container. The HCP may attach a label to the external surface of the container, and the label can comprise unique identification information indicative of the sterilization conditions of the interior of the container. More specifically, the HCP can use an input device to enter the status of the PI, and a machine coupled to the user interface can print a label comprising a bar code, a QR code, or an alphanumeric identifier corresponding with the sterilization conditions of the container, and the HCP can attach the label to the container.

In other examples, a camera 65' or other image recognition device configured to capture images of the PI can assist in determining whether the PI has changed state to indicate the characteristics of the container during the sterilization process and/or the status of the instruments. In particular, in examples in which the PI is not visible, such as when the PI is located inside the container and the container does not include the window, the camera 65' can capture an image of the PI or other sensor after the sterilization process before the container is opened and the PI is accessible. In the example shown in FIG. 41, the camera 65' may be positioned to read the PI 57' external to the container to help identify or read the PI. A processor 67' can be coupled to the camera 65' to receive data corresponding with the image. The processor 67' can compare the image with empirical data or utilize an algorithm, which is stored within memory, to determine if the state and/or measurement of the PI or sensor corresponds with a threshold process condition that would ensure the desired level of sterilization. Based on this comparison, the processor 67' can send a signal to any suitable notification device, as will be described below, by wireless or wired transmission to communicate the results to the container.

Figure 42A:
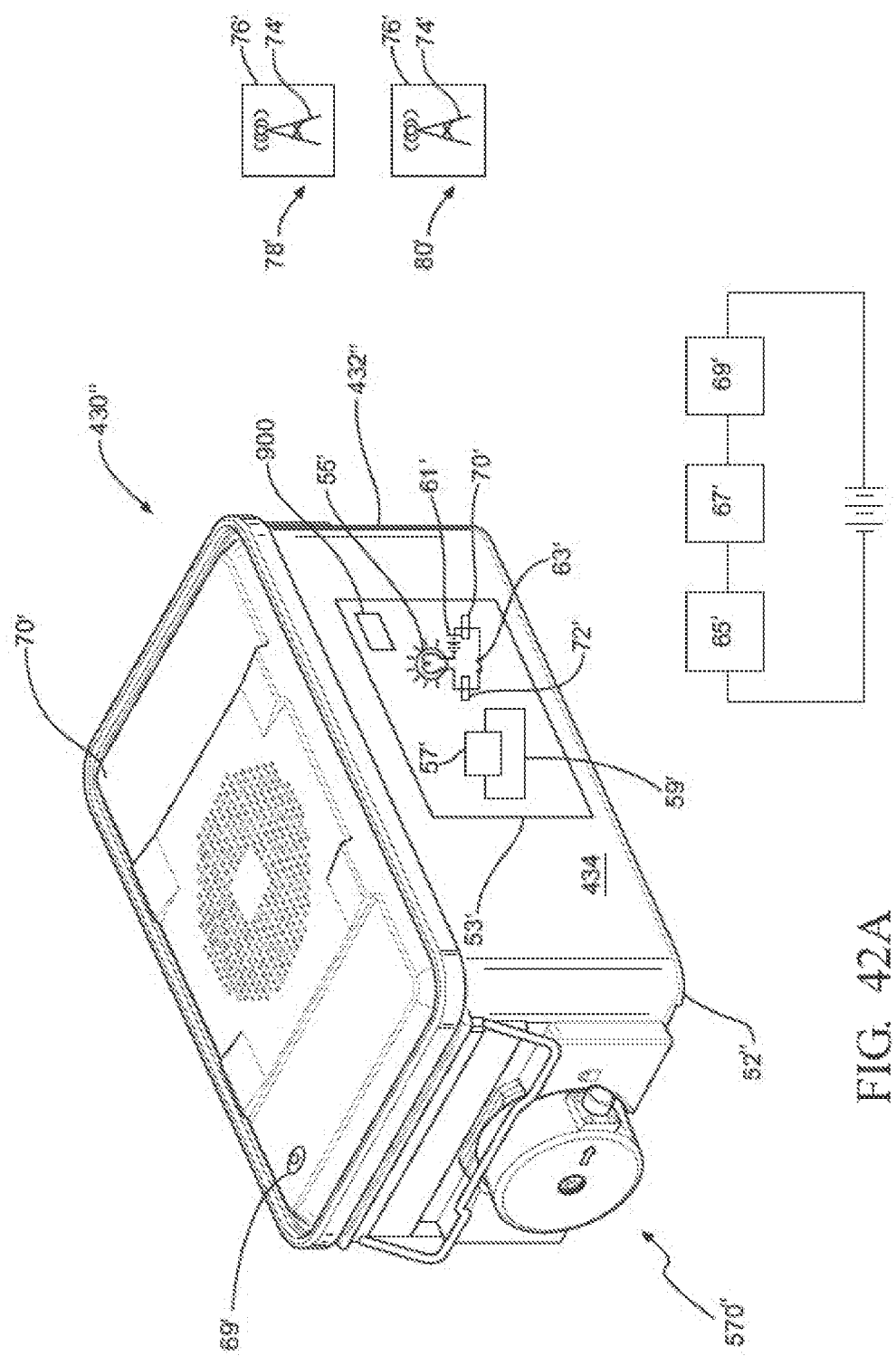
FIG. 42A is a perspective view of another example of a sterilization container, illustrating a sensor module comprising a non-electric sensor aseptically and removably coupled to an external surface of the container and a normally closed valve to fluidly communicate with the interior of the container.

Referring to FIG. 42A, an exemplary container 430" comprises a body 432" and other components, which are substantially similar to those of the container 430 shown in FIG. 21 and are identified by the same reference numbers as followed by the double prime symbol ("). However, in this example, the body 432" comprises a transparent window 53'. In addition, the container 432" further comprises a light source 55' and a PI 57', which are disposed within and/or coupled to the container 430", such that the PI 57' is directly exposed to steriliant gases within the container 430". The container 430" may further comprise a holder 59' or a mounting bracket configured to attach the PI 57' inside the container 430" adjacent to the transparent window 53', such that the HCP can see the state of the PI 57' and/or instruments within the container through the window 53' without opening the lid 70" and compromising the aseptic barrier. As described above, the location, size, orientation, and construction of the transparent window is not particularly limited, and the window may be located on any of the walls and/or lid of the sterilization container.

The light source 57' can be optionally configured to emit light at a predetermined wavelength range that optimally illuminates the PI 57' and the instruments positioned within the interior and provides a contrast in color to facilitate the HCP with inspecting the status of the PI 57' and the instruments through the transparent window 53'. The container 430" can further comprise one or more cells 61' coupled to the light source 55' for supplying power to the same, and a switch 63' configured to close a circuit comprising the cells 61' and the light source 55' to emit light on the PI and/or the instruments within the interior of the container 430". In certain examples, the light source 55' may be omitted.

After the sterilization process has been completed, the PI 57' can be analyzed by inspection through the transparent window 53' to determine the sterilization conditions within the container 430", thus serving to communicate the results to the HCP. In specific examples, the light source 55' can be selectively actuated by the HCP, so as to assist the HCP in reading the PI 57' and determining the sterilization process conditions within the container in view of the same, without compromising the aseptic barrier.

Furthermore, the PI 57' may be configured to measure characteristics of the sterilant gases entering through the container 430" over time. In such an example, the container 430" can comprise a camera 65' or other image recognition device configured to capture images of the PI 57' at predetermined time intervals during the sterilization process, to facilitate the HCP in determining when the PI 57' has changed state to meet or exceed a threshold process condition.

In particular, the camera 65' can capture an image of the PI 57' at a time interval at or near the end of the sterilization process. The processor 67' can be coupled to the camera 65' to receive data corresponding with the image. The processor 67' can compare the image with empirical data or utilize an algorithm, which is stored within a memory and indicative of the state of the PI corresponding with a desired level of sterilization. Based on this comparison, the processor 67' can send a signal to any suitable notification device, as will be described below, by wireless or wired transmission to communicate the results of the container 430".

Figure 43:
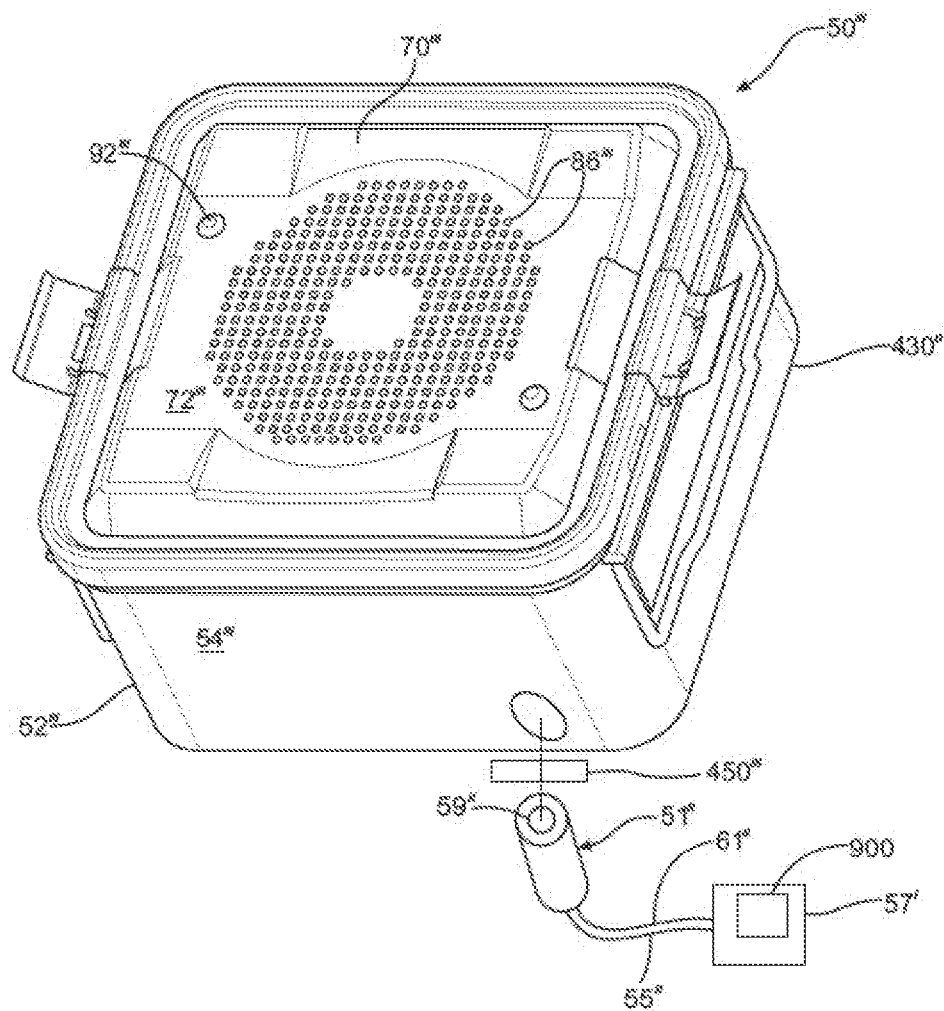
FIG. 43 is a perspective view of another example of a sterilization container comprising an airflow challenge cannula impeding airflow from an interior of the container to another embodiment of a sensor module.

Referring to FIG. 43, another exemplary container 50''' may comprise multiple components, which are substantially similar to those of the container 50 of FIG. 1 and are identified by the same reference numbers followed by a triple prime symbol ("'"). However, the container 50''' may further comprise a baffle or airflow challenge cannula 51" that impedes the flow or propagation of sterilant gases through the airflow challenge cannula 51" and to the PIs 57'. The cannula 51" can be removably and aseptically coupled to the container 50''', in any suitable fashion, and at any suitable location, such as any of the walls and/or lid of the sterilization container. The cannula 51" may also be mounted to the external walls of the container. This impedance to the flow of sterilant gases improves the reliability of determining if there are acceptable sterilization process conditions, particularly because the impedance simulates and corresponds with the sterilization of recessed portions of the instruments that may be comparably less exposed to the container than the outermost exposed surfaces of the instrument.

In particular, the cannula 51" can comprise a conduit 61" and a narrow or tortuous passage 55" that impedes the propagation of sterilant gases or steam to the PI 57'. In this example, the passage 55" of the cannula 51" terminates at one end with a port 59"' that fluidly communicates directly with the container 50'''. The passage 55" can further comprise an opposite end communicating with the PI 57'. The PI 57' can be disposed along the narrow passage 55" and spaced from the port 59"', such that a sterilant gas in the interior must propagate through the port 59"' and at least a portion of the passage 55" in order to reach the PI 57'. Alternatively, the PI 57' can be located at the opposite end of the cannula 51". Thus, in either case, the sterilant gas must displace any air trapped in the passage 55" to reach the PI 57', which corresponds with the sterilant gas displacing or propagating through air trapped in the recesses or pockets defined by surfaces of the instruments to sterilize those surfaces. The PI 57' disposed within this passage 55" can require comparably longer times to be exposed to sterilant gas than PIs disposed within the container or outside of the same because those PIs are exposed directly to sterilant gases within the container and the sterilizer without requiring the sterilant gases to first propagate through any passage before reaching the PI. Thus, a container comprising the PI disposed along or at the opposite end of the narrowed passage may require only a single PI because the PI disposed in the narrowed passage can improve the reliability in determining if proper sterilization process conditions obtained as compared to the PI disposed within the container or the PI disposed outside of the container.

In particular, the container 50''' can comprise a normally closed valve 450''', which is coupled to the port 59"' and removably coupled to the cannula 51". The cannula 51" can be removably coupled to the normally closed valve 450''', which can be configured to open in response to the same. Furthermore, the normally closed valve 450''' is configured to close in response to the cannula 51' or passage 53" or enclosure containing PI 57' being removed from the valve 450''', such that an aseptic barrier is provided.

While the PI may be used to determine if proper sterilization process conditions were achieved, the PI may be used in combination with or in substitution of the sensors previously described.

After the sterilization process has been completed, a signal corresponding with the status of the container and/or instrument can be electrically or non-electrically communicated to the HCP. The sensor module comprises one or more notification devices configured to communicate one or more characteristics within the container during the sterilization process and/or the status of the container and/or the instruments to the HCP. The characteristics can include the concentration of sterilant gases, the time of exposure to the same, the temperature, and/or the pressure. The notification devices can be coupled to the processor and configured to communicate the characteristics of the container and/or status of the container and/or the instruments, in response to receiving a signal from the processor directed to the same.

In one example, one or more notification devices can be in communication with the processor 384 (FIG. 11) in a manner such that one or more sensors disposed within the container can wirelessly communicate with the processor 384 and/or the notification devices to actuate the notification devices to communicate the characteristics within the container and/or the status of the container and/or the instruments therein, without compromising the aseptic barrier. As but one example, the processor 384 can receive a signal from any one or more of the optical sensor assemblies 202, 202', 202", 202''' and compare the measured concentrations of sterilant gases to empirically collected data corresponding with sterilization process conditions. If the processor 384 determines that the measured concentrations meet or exceed the empirically determined threshold process conditions that ensure a desired level of sterilization, the processor 384 can actuate LEDs 268, 270 or other notification devices to communicate the status of the container and/or instruments as being decontaminated to the desired level of sterilization. As a further example, the processor 67' (FIGS. 41 and 42) can receive signals from the camera 65' corresponding with captured images of the PI 57' during the sterilization process. If the processor 67' determines that one of those images corresponds with empirical data indicative of threshold process conditions that ensure the desired level of sterilization, the processor can actuate the LED 69' to indicate that the instruments have been decontaminated to the desired level of sterilization. However, the notification devices can be actuated by the HCP in response to manual inspection of the sensors or by various processors in response to signals received from any suitable sensors. Exemplary notification devices are provided below.

Referring back to FIG. 11, the exemplary sensor module 102 can comprise multiple notification devices, which can include the two LEDs 268, 270 that are coupled to the processor 384 and configured to emit light indicative of the characteristics within the container 50 during the sterilization process and/or the status of the container and/or the instruments therein. As one example, the LED 268 can be configured to emit red light indicative of the measured characteristics of the container 50 not meeting the threshold process conditions, in response to the LED 268 receiving a signal from the processor 384 corresponding with this condition. Furthermore, the LED 270 can be configured to emit green light indicative of characteristics of the container 50 meeting the threshold process conditions, in response to receiving a signal from the processor 384 corresponding with the same.

Referring to FIG. 4, each one of the LEDs 268, 270 can be seated in a separate one of the bores 164 formed in the shell top panel 154. More specifically, as exemplified in FIG. 4, the LED 270 may be seated in the associated bore 164, and O-rings 272 surround the LED 270. The O-rings 272 provide a seal between the LED 270 and the adjacent, inner cylindrical wall of the panel that defines the bore 164. Similarly, the LED 268 can be seated in the associated bore and surrounded by corresponding O-rings to provide a seal between the LED 268 and the adjacent inner cylindrical wall of the panel that defines the bore 164. The LEDs 268, 270 emit different colors of light indicative of a corresponding status of the container 50 and/or the instruments. Other examples of the sensor module (not shown) can include any number of LEDs configured to emit any colored light in a steady state or intermittent pattern to indicate any characteristic of the container.

Referring to FIGS. 44A and 44B, another notification device or filter presence notification device comprises an electro-mechanical notification device 1500, wherein, once it is actuated, does not require power and thus conserves the power of the cells 288 (FIG. 8) or other power source. The notification device 1500 is configured to assume at least two different positions, one indicating an acceptable condition and the other indicating a negative condition. More specifically, the notification device 1500 indicating the acceptable condition can indicate that the threshold process conditions for ensuring the desired level of sterilization were achieved or that the filter is present. The notification device 1500 indicating the negative condition can indicate that threshold process conditions were not satisfied to ensure the desired level of sterilization or that the filter is not present. In one example, the notification device comprises a button 1501 coupled to the container 50. The button 1501 is movable to a raised position indicative of the acceptable condition and a lowered position indicating the unacceptable condition. The notification device 1500 further comprises a biasing member 1502, such as a helical spring, configured to move the button 1501 to the raised position, and a detent 1504 configured to abut and hold the button 1501 in the lowered position. In certain examples, the notification device 1500 can further comprise an actuator 1506, such as a solenoid, to remove the detent 1504 from the button 1501, such that the biasing member 1502 moves the button 1501 to the raised position in response to the actuator 1506 receiving a signal from the processor 384 when the processor 384 determines that the acceptable condition is met, e.g. acceptable sterilization conditions have been met or via the pins 276 creating an open circuit indicating that the filter medium 410 is present.

Figure 45A:
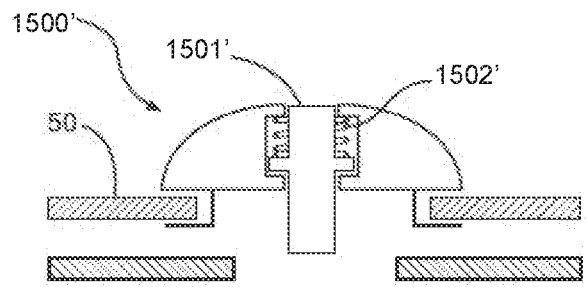
FIGS. 45A and 45B are schematic diagrams of another exemplary notification device having a button movable to a raised position for indicating the presence of a filter and a lowered position for indicating the absence of the filter.
Figure 45B:
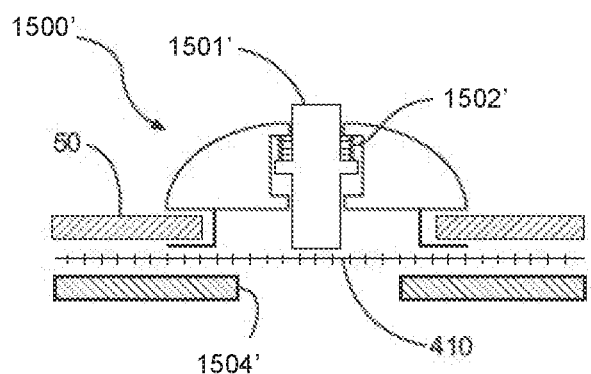

Referring to FIGS. 45A and 45B, another example of the mechanical notification device 1500', which does not require power and thus conserves the power of the cells 288 (FIG. 8) or other power source, comprises a button 1501', a biasing member 1502', and other components, which are substantially similar to those of the mechanical notification device 1500 and are identified by the same reference numbers followed by a single prime symbol ('). Preferably, the mechanical notification device 1500' is coupled to the container in a position that is visible to a user when the container rests on a shelf within the sterile inventory room. However, while the biasing member 1502 shown in FIGS. 44A and 44B is configured to move the button 1501 to the raised position, the biasing member 1502' of the present exemplary notification device 1500' urges the button 1501' to a lowered position. The filter medium 410 in this example holds the button 1501' in the raised position to indicate the presence of the filter medium 410. Furthermore, the container 50 further comprises an opening 1504' and/or other clearance permitting the button 1501 to move to the lowered position, so as to indicate the filter is not present. Still, other configurations of the filter presence sensor are also contemplated.

Referring to FIG. 46, the filter medium 410 can also be detected by a non-mechanical filter detector, such as an optical filter detector 101. The optical filter detector 101 may be integrated into the container, the sensor module, or other component, as shown. The optical filter detector 101 can transmit a signal to one of the aforementioned processors or other processor, which then sends a command signal to one or both of the LEDs 268, 270 or other indicator to emit light or otherwise indicate whether the filter medium 410 is present. The processor could also transmit a signal by wired or wireless communication to a docking station 1000 or other location to activate other notification devices configured to communicate characteristics of the container including the presence of a filter. The docking station 1000 may be configured to hold or carry the container on a shelf in a sterile inventory room.

In other examples, the docking station 1000 can further comprise its own filter presence sensor 1002 configured to detect whether the container has a filter mounted therein. In one example, the filter presence sensor 1002 can comprise an optical sensor 1004 that scans the container 430 and determines if the filter medium 410 is present. The docking station 1000 aligns the filter apertures 86 to the optical sensor 1004 on the docking station 1000 such that it can determine if a filter medium 410 is present.

Referring to FIG. 46, a handheld reader 2000 can be used to locate a container within a sterile inventory room. The handheld reader 2000 comprises an optical filter detector 2002 configured to scan the lid 70 to determine whether the filter medium 410 is present. More specifically, the optical filter detector 2002 can be aligned with one or more apertures 86 formed in the lid 70 of the container 430 to scan those apertures 86 and determine whether the filter medium 410 is present beneath the lid 70. The handheld reader 2000 can further comprise a processor 2004 that communicates with the processor in any one of the container, the sensor module, and/or the docking station 1000 to determine whether those components previously detected the presence of the filter.

The container can further comprise a PI presence sensor configured to detect the presence of the PI within the closed container, within the external sensor module, or within the airflow challenge cannula 51". One non-limiting exemplary benefit of verifying the presence of the PI is that this ensures that only containers including the PI are delivered to a sterile operating room for a surgical procedure. In other words, the lack of the PI within the container can prevent an HCP, who is preparing for a surgical procedure, from confirming that the instruments have been sterilized, thus requiring one or more additional containers to be delivered to the surgical room until the HCP can verify that the instruments have been sterilized. This can delay the surgical procedure and adversely affect the available resources of the hospital facility.

Figure 47A:
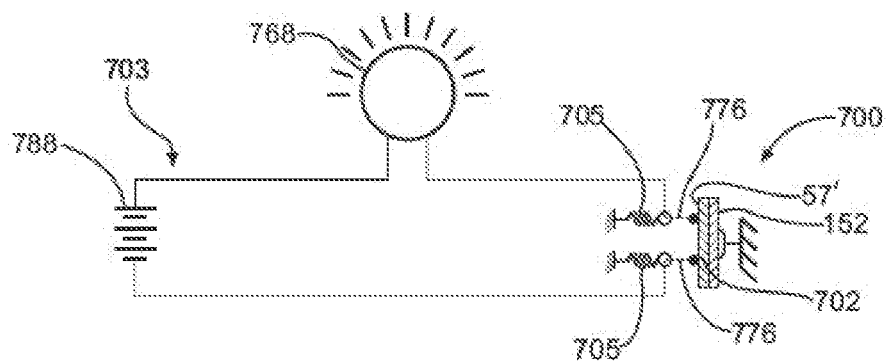
FIGS. 47A and 47B are schematic diagrams of an exemplary sensor assembly having a sensor for detecting the presence of a non-electric notification device comprising a conductive layer and emitting light to indicate the same.
Figure 47B:
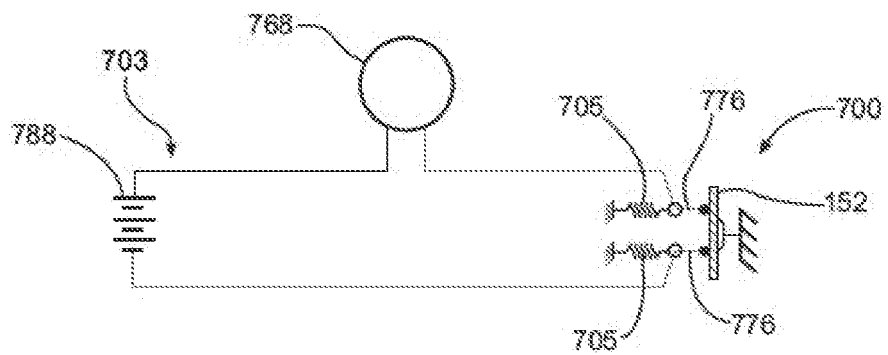

Referring to FIGS. 47A and 47B, one exemplary PI presence sensor 700 is configured to emit light when the PI 57' is present. In particular, the sensor 700 can comprise two conductive pins 776 and other components substantially similar to the conductive pins 276 and other components of the filter presence detector 209 shown in FIGS. 9 and 11. The conductive pins 776 of the PI presence sensor 700 can be urged toward a portion of the PI 57' when the PI 57' is present. In particular, the PI presence sensor 700 can include one or more springs 705 that urge the conductive pins 776 toward the PI 57'. Furthermore, a portion of the PI 57' that extends between the two pins 776 can include a conductive layer 702, such as a foil layer, which closes a circuit 703 when the pins 776 are urged into contact with the conductive layer 702. When the PI 57' and its conductive layer 702 are present, the circuit is closed to indicate the presence of the PI 57'. However, when the PI 57' and its conductive layer 702 are not present, the springs 705 move the pins 776 to abut against the non-conductive pad or shell 152, such that the circuit is open and the LED 768 does not emit any light thus indicating that the PI 57' is not present. The circuit can further comprise a cell 788 and a LED 768, which emits light in response to the circuit being closed so as to indicate that the PI 57' is present.

Figure 48A:
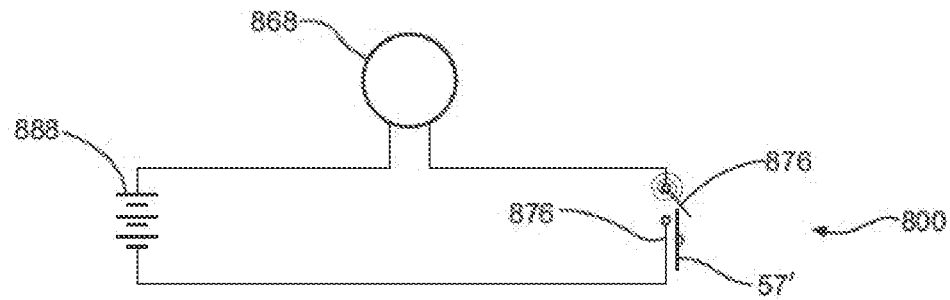
FIGS. 48A and 48B are schematic diagrams of an exemplary sensor assembly having a sensor for detecting the absence of a non-electric notification device comprising non-conductive material and emitting light to indicate the same.
Figure 48B:
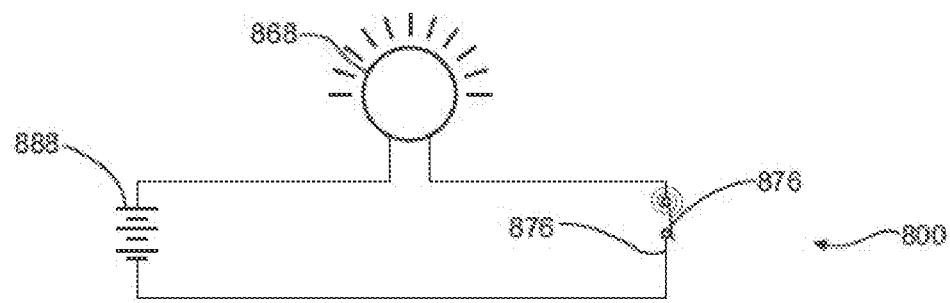

Referring to FIGS. 48A and 48B, another exemplary PI presence sensor 800 is configured to emit light when the PI 57' is absent. The sensor 800 may comprise components, which are substantially similar to the presence sensor 700 of FIGS. 47A and 47B and comprise similar components as identified by corresponding reference numerals increased by 100. However, while the PI presence sensor 700 of FIGS. 47A and 47B comprises a conductive layer 702, the present exemplary PI presence sensor 800 is comprised of a non-conductive material without any conductive layer. Moreover, while the sensor 700 of FIGS. 47A and 47B comprise a pair of opposing pins 776 urged into contact with the conductive filter medium 410, the sensor 800 comprises a normally closed switch 876 configured to receive the PI 57', which urges the switch 876 to an open position. In this example, the PI 57' is comprised of non-conductive material without any conductive layers exposed on the exterior of the PI 57'. Thus, when the non-conductive PI 57' is disposed within the switch 876, the switch 876 does not close and the circuit remains open with no current being supplied to the notification device, which in this example is the LED 868. However, when the PI 57' is absent, the switch closes and power is supplied to the notification device, which in this form is the LED 868 emitting light to indicate that the PI 57' is absent. Of course, other configurations of the PI presence sensor are contemplated.

While other exemplary containers can include speakers for communicating the sterilization process conditions, it may be preferred that the speakers or other sound emitters be used for assisting the HCP in finding the container in a sterile inventory room when prompted by the HCP, as described below.

The notification device may be further configured to alert an HCP of the location of the container and instruments sealingly contained therein, such that the HCP can efficiently retrieve the container from a sterile inventory room and deliver the same to a sterile operating room for use during a surgical procedure.

In addition to, or in substitution of, using LEDs to visually indicate to the HCP the status of a container, a speaker can be configured to emit a sound, such as an intermittent beep. The LEDs and speakers can be coupled to any of the cells previously described to provide power thereto to permit the HCP to find the corresponding container and the instruments therein. However, the LEDs and the speakers can be coupled to other power sources that are integrated in the containers, the sensor module, or other devices to receive power from the same.

Referring again to FIG. 42A, the exemplary container 430" can further comprise a remotely-detectable element 72' configured to wirelessly communicate with at least one remote detecting antenna 74' of a reader 76', such as a docking station 78' or a hand-held wand 80' manipulated by the HCP. The remotely-detectable element 72' can comprise an RFID element, a bar code, a QR code, or any suitable machine-readable element, which includes unique identification information corresponding with the container and/or the instruments disposed within the container. In one example, the unique identification information can comprise a serial number or other unique identifier. The reader 76' can transmit a signal including data indicative of the serial number corresponding with an inventory roster of instruments within a corresponding container to be retrieved from the sterile inventory room and delivered to a sterile operating room where the container is opened, such that the HCP can use the designated sterile instruments for a surgical procedure.

In one example, the notification device can comprise one or both of the LEDs 268, 270 (FIG. 11) as described above, which is further configured to intermittently emit light to assist the HCP in finding the container 50 within the sterile inventory room. Thus, once the reader 76' is in proximity with the remotely-detectable element 72', the LEDs 268, 270 of the notification device can be configured to emit light for a predetermined amount of time and then turn off as the notification device enters into a sleep mode, thus conserving the power of the cells 288.

The remotely-detectable element 72' and the notification device can be integral parts of a stand-alone device, such as a puck or disk-shaped body, which is removably coupled to the container. However, the stand-alone device can have any suitable shape. The reader 76' can have a memory storing the unique identification information of the remotely-detectable element 72' with the corresponding container and designated instruments therein prior to the sterilization process, such that the data can be modified in response to the processor receiving signals from any one of the sensors, as described above, during the sterilization process to communicate the sterilization condition of the container and corresponding instruments after the sterilization process has been completed. Furthermore, the notification device can be configured to receive a signal from the sensor module indicative of the sterilization process measurements or conditions, and the device can be further configured to transmit a signal to the reader 76', such that the reader 76' can store the same corresponding with the unique identification information. The remotely-detectable element 72' and the notification device can be integral parts of any one of the sensor modules as described above.

The sensor module further comprises one or more notification devices configured to communicate the characteristics within the container during the sterilization process and/or the status of the instruments and/or the container. Based on the measured characteristics, the processor can determine if the threshold process conditions have been met or exceeded to ensure that the desired level of sterilization has been achieved. The notification device can be any suitable notification device, including any one or more of the same notification devices, as described above, for communicating the sterilization process conditions and/or location of the container. However, the sensor module can comprise any number of other suitable notification devices.

Figure 42B:
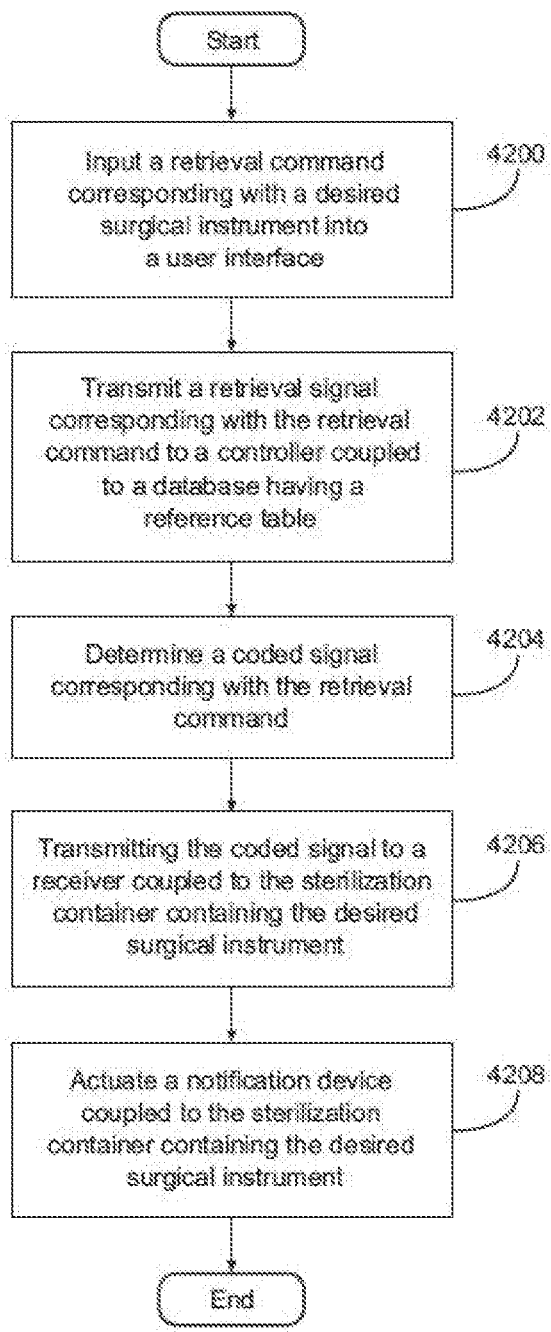
FIG. 42B is a flow chart of a method for retrieving the sterilization container of FIG. 42A containing a desired surgical instrument.

FIG. 42B is a flow chart of a method for retrieving a sterilization container containing a desired surgical instrument. At step 4200, a retrieval command corresponding to the desired surgical instrument is inputted into a user interface. The user interface can be a tablet computer, a smart phone, a desktop computer, a laptop computer, or any other suitable user interface.

At step 4202, a retrieval signal is transmitted from the user interface to a controller that is coupled to a database. The retrieval signal corresponds with the retrieval command, and the retrieval signal may be transmitted through wireless or wired communication from the user interface to the controller. In one example, the controller and the database are components of a server or high performance computer configured to process multiple requests to retrieve containers having desired surgical instruments from multiple user interfaces. More specifically, the database has stored therein a reference table including a plurality of reference retrieval commands and corresponding reference coded signals. Each one of the reference coded signals may be indicative of a container, a surgical tool contained therein, and/or a status of the surgical instrument. Exemplary statuses of the surgical instrument can include sterile, contaminated, or various other statuses.

At step 4204, a coded signal corresponding with the retrieval command is determined. In particular, the controller can access the database and utilize the reference lookup table and the retrieval command to determine the coded signal.

At step 4206, the coded signal is transmitted from the controller to a receiver coupled to the sterilization container containing the desired surgical instrument. In one embodiment, the coded signal can be transmitted to an RFID tag coupled to the sterilization container. The surgical instrument within the container may not have an RFID tag associated therewith. In addition, the controller can transmit the coded signal with sufficient power to reach the sterilization container within an inventory room having multiple other surgical containers therein or to a sterilization container located in any portion of a hospital or other medical facility. In other embodiments, the sterilization container and/or the surgical instrument may include a receiver that communicates with a protocol other than radio-frequency communication.

At step 4208, a notification device that is coupled to the sterilization container having the desired surgical instrument can be actuated in response to the receiver receiving the coded signal. The notification device can be any of the notification devices described above, including one or more light sources coupled to the container. In one example, the light source can be an LED 69' positioned external to the interior of the sterilization container. In another example, the light source can be an LED 55' positioned within the interior of the container and be visible through the transparent window 53'. The container's light source can be turned on to visually indicate to the HCP the location and/or status of the container having the desired surgical instrument. In addition, the light source can illuminate the contents of the instruments positioned within the interior of the container, such that the contents can be verified by manual inspection through the transparent window 53'. This is advantageous as the contents of the sterilization container may have been mistakenly entered into the user interface when initially loaded. Thus, if the HCP were to identify the sterilization container that supposedly included the desired surgical instrument, and opened that sterilization container, the HCP would not see the desired surgical instrument. Furthermore, the misidentified sterilization container would no longer be sterile as it was opened by the HCP seeking the desired surgical instrument. By visually inspecting the contents of the sterilization container without compromising sterility of the same, this type of resource-wasting activity can be mitigated.

These contents can include the desired surgical instrument and/or the PI 57'. In one example, the controller can actuate the LED to intermittently flash on and off. In addition to, or in substitution of, using LEDs, the speaker can be actuated to emit a sound, such as an intermittent beep. The LEDs and speakers can be coupled to any of the cells previously described above to provide power thereto and permit the HCP to find the corresponding container containing the desired instrument.

When the contents of the container or the status of those contents is changed, a status update command can be inputted into the user interface, and the status update command can indicate the container, the instrument contained within the container, and the status of the instrument. The notification device may then be activated allowing easy retrieval of the desired sterilization container from an inventory room. The user interface can transmit a status update signal corresponding with the status update command to the controller. The controller can update the reference coded signal corresponding with the surgical instrument and the container containing the surgical instrument.

Figure 49A:
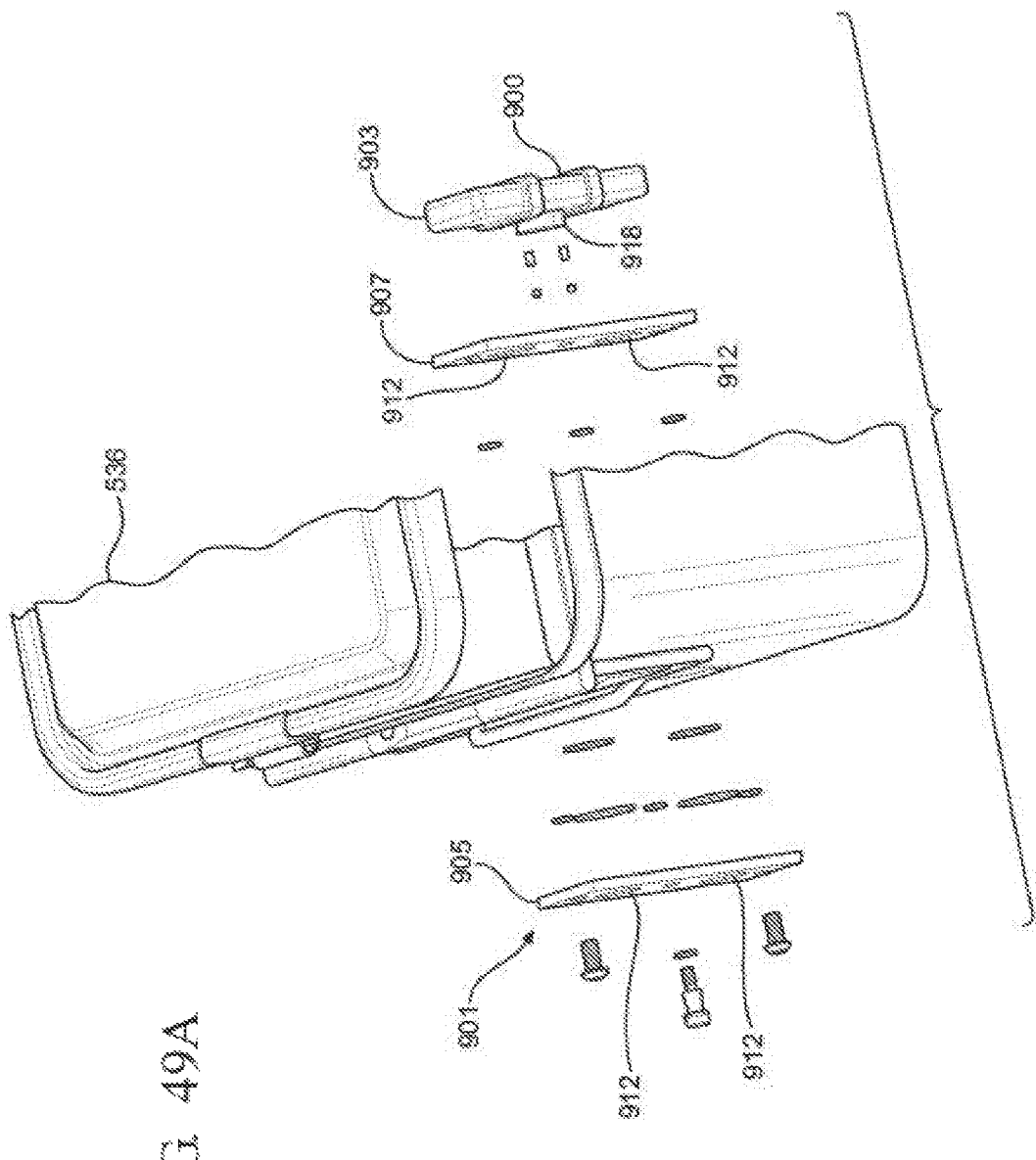
FIG. 49A is an exploded view of another sensor module, taking the form of a phase change material (PCM) notification device coupled to one side panel of the sterilization container to position the PCM notification device within the interior of the sterilization container.

Referring to FIG. 49A, one exemplary stand-alone sensor/notification device can comprise a phase change material (PCM) device 900. The PCM device may be coupled to, disposed within, or adjacent to, any suitable sterilization enclosure, such as container 50. The PCM device may generally function to indicate the amount of heat energy that was received by the phase change material disposed therein, which correlates to the amount of heat energy that has been transferred to the instruments present within the sterilization container by the sterilizer. This correlation may enable the HCP to determine whether the instruments or other contents of the sterilization container have reached predetermined threshold process conditions to ensure that the desired level of sterilization has been achieved. While one example of sufficient heat energy for achieving predetermined standard sterilization can be 133° C. saturated steam for 4 minutes, the PCM notification device 900 can be configured to indicate if other conditions are present for achieving a predetermined level of steam sterilization. Furthermore, the PCM device can be used to monitor process conditions in any suitable device/system other than in the context of sterilization of surgical instruments.

As shown in FIG. 49A, the PCM device 900 includes a mounting assembly 901 for attaching the PCM notification device 900 to the container. In this example, the PCM notification device 900 is positioned within the interior of the container 50. In one example, the mounting assembly 901 enables rotatable mounting such that the PCM device may be rotated relative to the sterilization container. In one configuration, the mounting assembly 901 is arranged for vertical mounting of the PCM notification device 900 to the sterilization container 50. In the illustrated embodiment, the mounting assembly 901 includes an external plate 905 positioned external to the interior of the container, an internal plate 907 positioned within the interior of the container. Of course, other types of mounting configurations are contemplated.

Each one of the plates 905, 907 may have one or more transparent windows 912 through which the PCM device 900 can be visible. Alternatively, the transparent windows 912 can be integrated within any portion of the body or the lid of the container 50 to permit inspection of the PCM device 900 positioned within the interior of the container 50. The transparent window 912 may include one or more markings that correspond to desired sterility levels as will be described below. Furthermore, it is contemplated that the PCM notification device 900 can be positioned in any suitable location within the interior of the container, external to the same, or as an integral portion of any panels forming lid or the body of the container. In addition, the PCM notification device need not be mounted to the container, but may be merely placed within the container before the container is placed into the sterilizer.

Figure 49B:
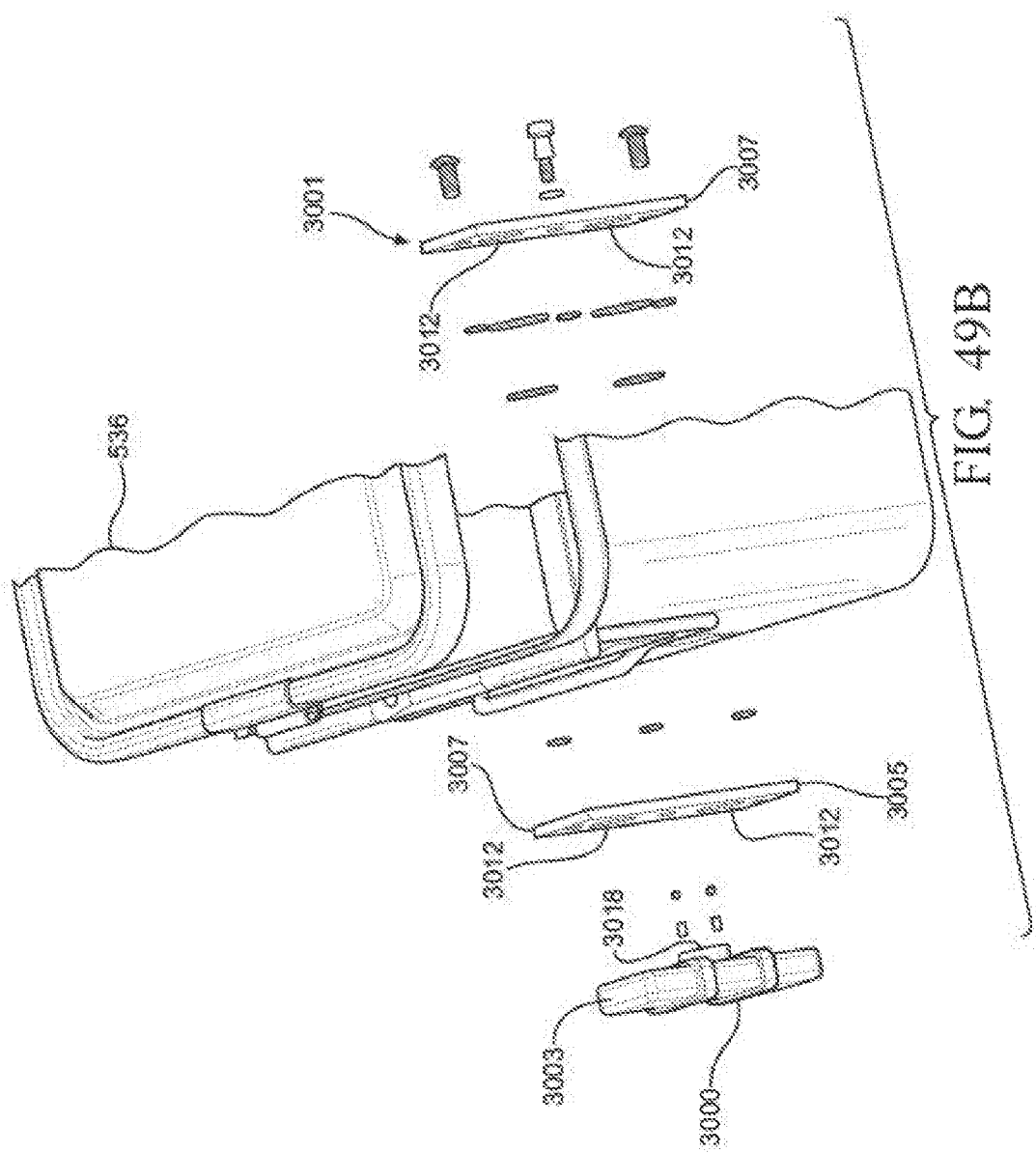
FIG. 49B is an exploded view of the PCM notification device of FIG. 49A coupled to one side panel of the sterilization container to position the PCM notification device external to the interior of the sterilization container.

Referring to FIG. 49B, another embodiment of the PCM notification device 3000 is similar to the PCM notification device 900 of FIG. 49A. However, while the PCM notification device 900 is FIG. 49A is placed within the interior of the container 50, the PCM notification device 3000 is positioned external to the interior of the container. As one example, the PCM notification device 3000 can be coupled to an external surface of the front panel or side panel. As a further example, the PCM notification device can be a separate component positioned within the sterilizer and spaced apart from the container's walls.

Figure 49C:
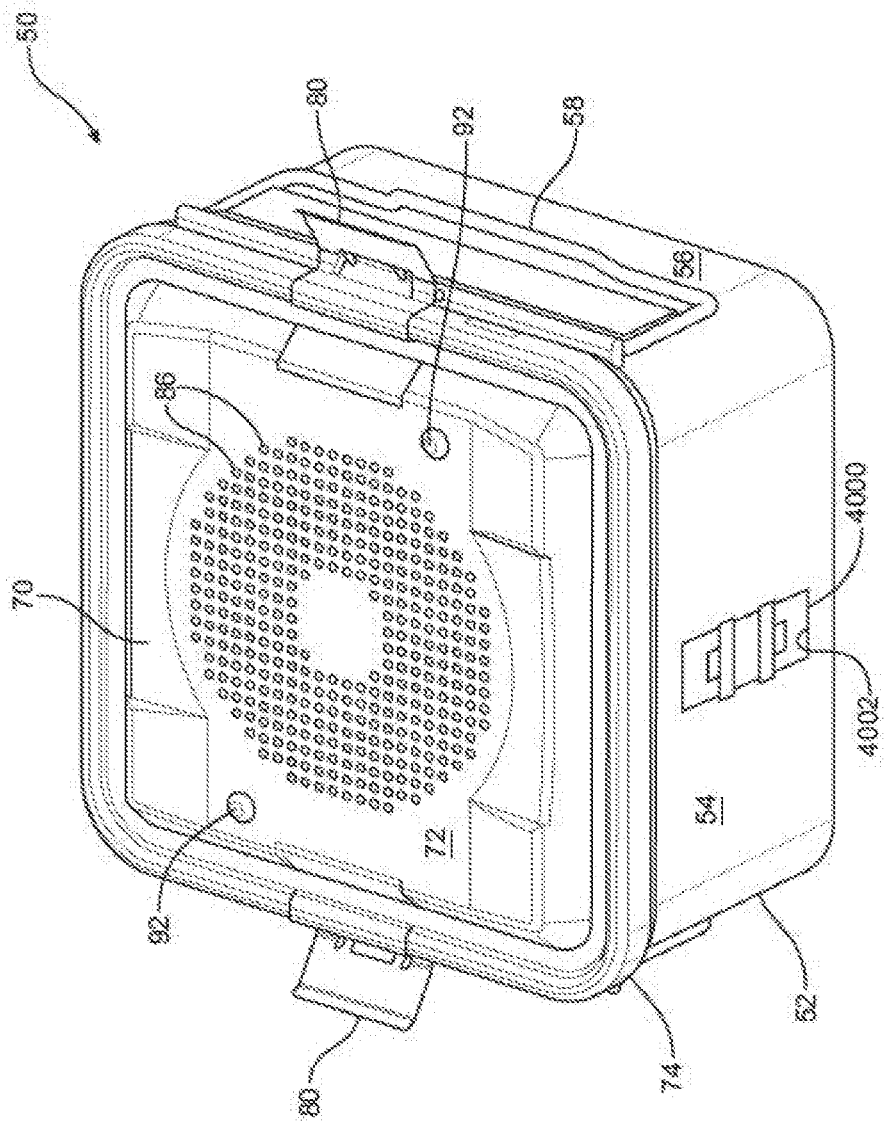
FIG. 49C is a perspective view of the PCM notification device of FIG. 49A integrated within the side panel of the sterilization container.

Referring to FIG. 49C, still another embodiment of the PCM notification device 4000 is similar to the PCM notification device 900 of FIG. 49A. While the PCM notification device 900 of FIG. 49A is placed within the interior of the container 50, the PCM notification device 4000 is an integral portion of the container 50. In particular, the front panel 54 of the container 50 can define an opening 4002 and the PCM notification device 4000 can be aseptically received within the opening 4002 and coupled to the container 50 to sealingly block the opening 4002. The location of the opening 4002 and corresponding PCM device 4000 is not particularly limited. Furthermore, it is contemplated that the PCM device could be an integral component of the container, yet still be rotatably mounted and be aseptically received.

The PCM notification device 900 can comprise a phase change material (PCM) 902 that undergoes a phase change and moves in a predictable manner in response to the conditions within the container. In one example, the PCM device includes a phase change material that melts when exposed to predetermined conditions, such as 133° C. saturated steam for 4 minutes, so as to communicate the same to the HCP examining the phase change notification device 900. It should be appreciated that the type and amount of PCM utilized in the PCM device is selected to correspond to the desired conditions sought to be monitored and/or achieved. For example, if a higher amount of heat transfer is desired to be measured, the PCM included in the PCM device may have a higher melting point than a PCM used to measure a smaller amount of heat transfer. Along the same lines, if a higher amount of heat transfer is desired to be measured, the amount of PCM included in the PCM device may be higher than the amount of PCM used to measure a lower amount of heat transfer.

The PCM may comprise a solid-liquid phase change material, a material that transforms from the solid phase to the liquid phase at a defined temperature, and absorbs energy during this process. The PCM may be selected from the group comprising a salt, such as eutectic salts, a salt-based hydrate, an organic compound, or combinations thereof. The salt-based hydrate may be selected from the group of hydrated calcium chloride or hydrated sodium sulphate. The organic compound may comprise paraffin. Non-limiting examples of the PCM 902 may further include urea, carbamide, carbonyldiamide, and combinations thereof. In certain embodiments, the PCM is the same color in both the melted state and the solid state, i.e., no color change results from melting the PCM. Generally, paraffins have can have lower fusion energy than salt hydrates but may not have similar challenges in repeatedly transitioning between solid and liquid states. While paraffin only physically changes and keeps its composition when heat is released or gained, hydrated salt chemically changes when heat is released or gained. However, the low thermal conductivity of paraffins decreases the rate of heat stored and released during the melting and crystallization processes.

In some embodiments, the PCM may be configured to fully melt within a narrow temperature range, such as within a range of 10 degrees Celsius above or below a temperature point, within a range of 5 degrees Celsius above or below a temperature point, within a range of 1 degrees Celsius above or below a temperature point, or within a range of 0.5 degrees Celsius above or below a temperature point. In other words, in these embodiments, the PCM fully melts within a narrow band of temperatures, such as temperature bands spanning 20, 10, 2, or 1 degrees Celsius. In some cases, the PCM may be configured to fully melt at a sharp melting point, i.e., at a discrete temperature point. Of course, the PCM may be configured to melt within any suitable range from any melting point. Non-limiting examples of melting ranges can include 100 to 150° C., 120 to 140° C., 130 to 140° C., 130 to 135° C., 133 to 135° C., or 134 to 135° C.

In still another example, the PCM can be embedded inside a graphite matrix, thus considerably increasing the heat conductivity of the composition without significantly reducing the energy storage. Filler materials other than graphite are also contemplated to be mixed with the PCM to adjust the desired thermal conductivity of the mixture and tune the PCM notification device to indicate when certain process conditions have been experienced by the PCM notification device, i.e., those process conditions that correlate to a desired level of sterilization.

The PCM used in the PCM notification device 900 may preferably have a specific repeatable temperature that produces a reversible phase change, solid to liquid for example, to allow it to move or flow in a predictable manner. In another embodiment, the PCM used in the PCM notification device 900 can be a thermoset material that undergoes an irreversible phase change.

Figure 50B:
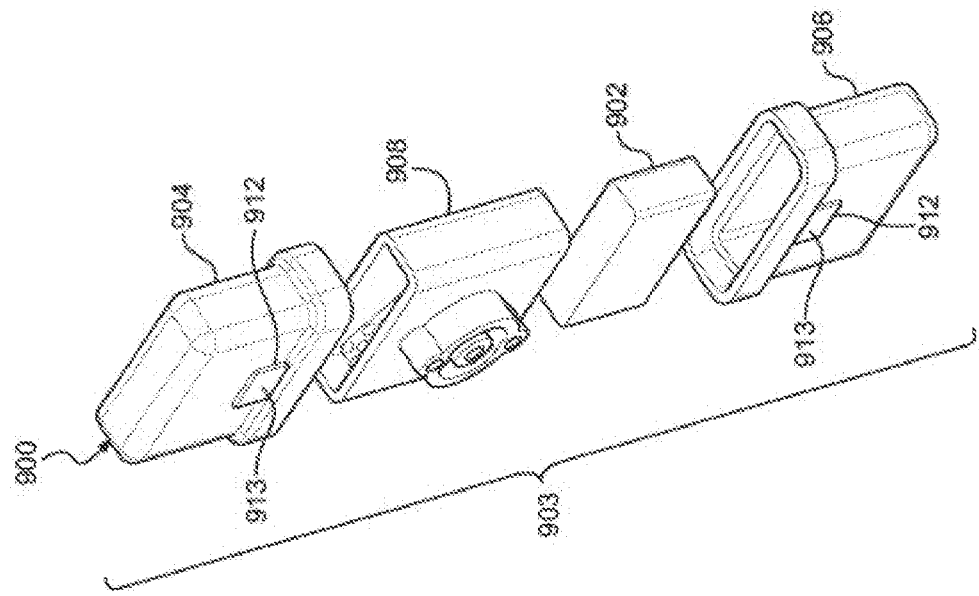
FIGS. 50A and 50B are exploded views of the exemplary PCM notification device of FIGS. 49A-C, illustrating the PCM in a corresponding one of upper and lower chambers of the PCM notification device.
Figure 50A:
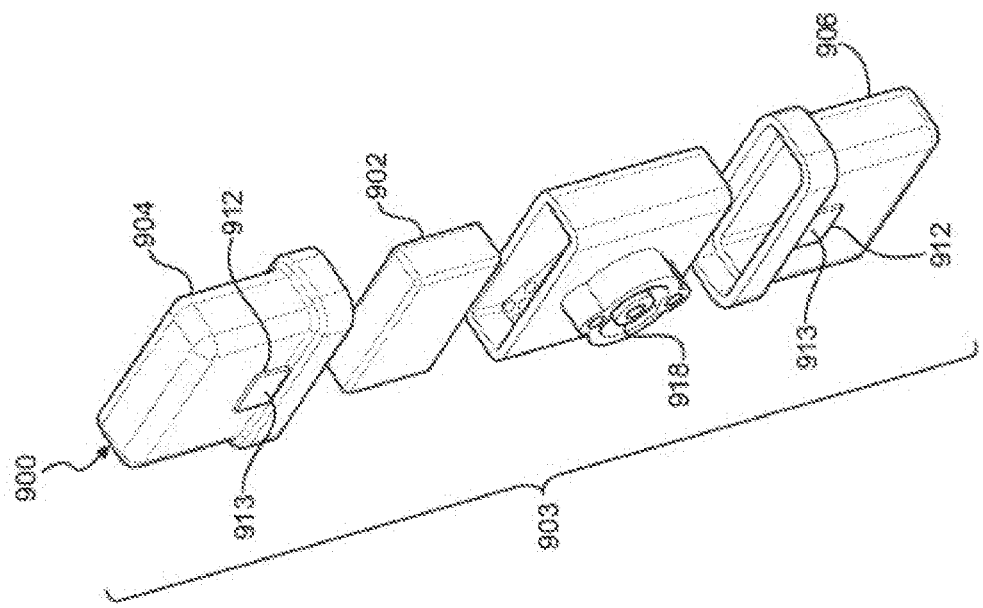

Referring to FIGS. 50A and 50B, in another example, the PCM notification device 900 can comprise a housing 903, which comprises an upper chamber 904 and a lower chamber 906, and the force of gravity can transfer the PCM 902 that has undergone a phase change from the upper chamber 904 to the lower chamber 906 to thus indicate a steam sterilization state.

The portions of the housing 903 comprising the upper and lower chambers 904, 906 can be fully or partially transparent, or may include transparent window 912 shown, such that visual inspection of the upper and lower chambers 904, 906 can reveal how much of the PCM 902 is present in the upper chamber and/or the lower chamber. It is also contemplated that any components of the PCM device, such as the housing, comprises transparent material and no distinct window is included. Any suitable transparent component or component of the PCM notification device adjacent to a transparent component may include the one or more markings described below.

The void space 911 (FIG. 51A) in the PCM housing assembly 903 may comprise a specific gas or gas mixture that makes up the volume of space inside the PCM housing assembly that surrounds the PCM. This gas may preferably be an inert gas, a dry gas or a gas that does not react, mix or change the PCM characteristics throughout the useful life of the PCM notification device If the threshold amount of PCM has transferred to the other chamber, typically the lower chamber, it can be determined that the PCM notification device has been exposed to the threshold process conditions to ensure that the desired conditions have been achieved in the environment surrounding the PCM notification device. In certain instances, the threshold amount is all of the PCM that is included in the PCM device that is visually detectable. In other words, if all of the PCM included within the PCM device that is initially present in the upper chamber before exposure to the process, such as the sterilizer, undergoes a phase change and is now present in the lower chamber, it can be concluded that the threshold process conditions have been achieved. The amount of phase change material included in the PCM notification device may have a heat of fusion, in the aggregate, that corresponds to the amount of heat energy necessary to achieve the threshold conditions that correspond to a desired level of sterilization for the surgical instrument included in the sterilization container.

Figure 51C:
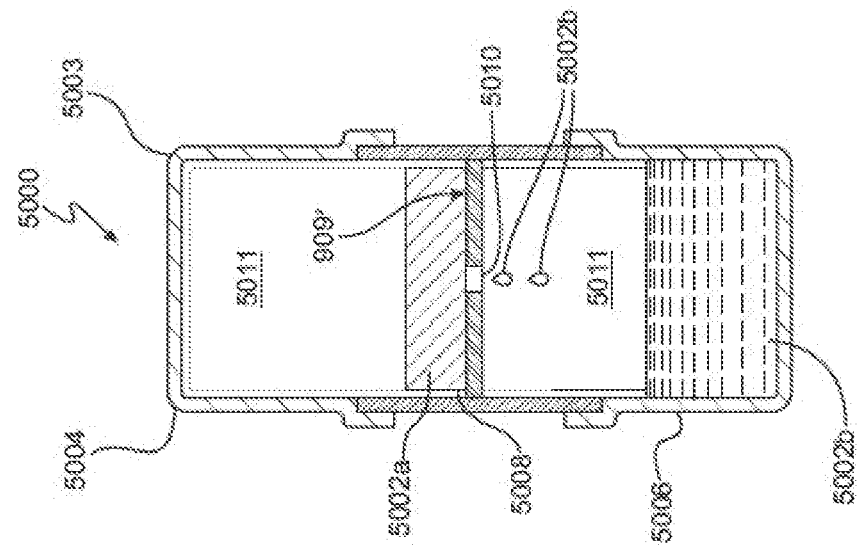
FIG. 51C is a cross-sectional view of another exemplary PCM notification device, illustrating the PCM notification device having a baffle in the form of a plate having a single orifice, with a portion of the PCM being unmelted and positioned within an upper chamber above the baffle plate and a portion of the PCM being melted and transferred through the orifice into a lower chamber beneath the baffle plate.
Figure 51B:
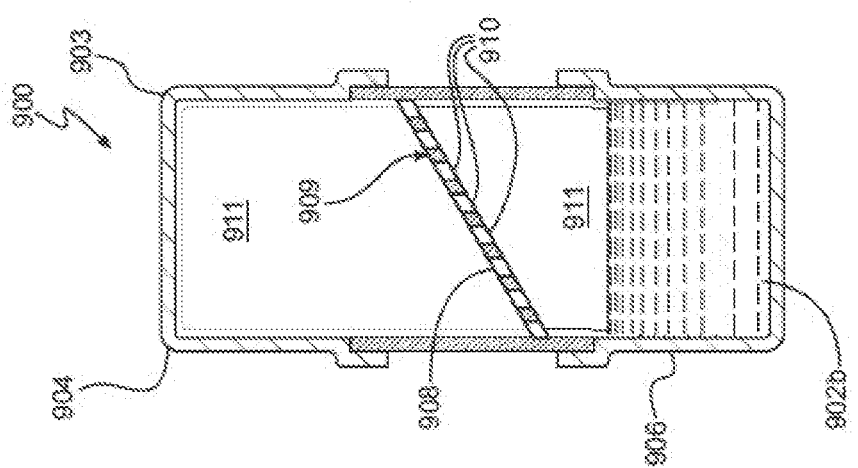
FIG. 51B is a cross-sectional view of the PCM notification device, illustrating the entire amount of PCM being fully melted and transferred from the upper chamber to the lower chamber so as to indicate that the instruments have been exposed to the threshold process conditions for ensuring a desired level of sterilization.
Figure 51A:
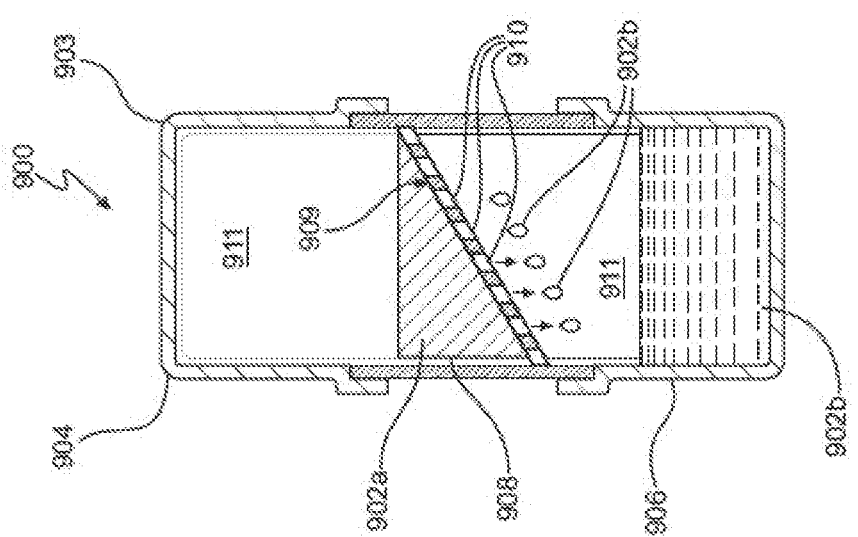
FIG. 51A is a cross-sectional view of the PCM notification device, illustrating one portion of the PCM being unmelted and disposed in the upper chamber and another portion of the PCM being fully melted in the lower chamber.

Referring to FIGS. 51A and 51B, the PCM notification device 900 can further comprise a baffle 909 positioned between the upper chamber 904 and the lower chamber 906 to selectively allow phase change material that has undergone a phase change to move from the upper chamber 904 to the lower chamber 906 at a predetermined rate and a predetermined amount when the PCM device 900 has been exposed to sufficient heat energy, i.e., heat energy in an amount that correlates to the desired level of sterility. The baffle 909 may comprise a plate (FIG. 51C), a screen, or a grating (FIG. 51B). The baffle may also be integral with the housing.

By controlling the configuration of the baffle 909, i.e., the orientation, the texture, and/or the number of openings, the rate of flow of the PCM 902 from the upper chamber 904 to the lower chamber 906 can be controlled. In other words, by controlling the rate of flow from the upper chamber 904 to the lower chamber 906, the amount of time that it takes for PCM 902 to move from the upper chamber 904 to the lower chamber 906 is adjusted. The amount of time can be adjusted by changing the configuration of the baffle 909 to match the amount of heat energy necessary to achieve the threshold process conditions that correspond to the desired level of sterility.

Referring to FIGS. 51A and 51B, the grate 908 of the baffle 909 comprises a plurality of openings 910 that allows material to move from the upper chamber 904 to the lower chamber 906. The size and shape of the opening 910 may be tuned to correspond to the size of solid particles that can pass from the upper chamber to the lower chamber. If a smaller opening is provided by the baffle 909, large aggregates of PCM present in the upper chamber 904 cannot pass through the opening 910 in the solid state. Thus, the opening prevents solid PCM from moving from the upper chamber 904 to the lower chamber 906 if the solid PCM 902a has dimensions larger than the opening. It is also contemplated that the openings 910 may be sized to allow semi-solid phases to transfer from the upper chamber to the lower chamber.

These openings 910 can be a series of circular apertures, a series of longitudinal slots arranged parallel to one another, or other orifices having any suitable shape to allow gravity flow of the PCM when in a melted, viscous or liquid state. In addition, by permitting fully melted PCM 902b to transfer from one chamber 904 to another chamber 906, the baffle 909 can prevent fully melted PCM 902b from pooling around unmelted portions of PCM 902a, and influencing their ability to melt.

The size/shape of the opening(s) 910 may be configured according to the desired rate of mass transfer desired, i.e., the rate of mass transfer that is correlated to the amount of heat transfer to achieve threshold process conditions. For example, each opening 910 in the baffle 909 may have a width no greater than 1, 2, 3, 4 or 5 mm. In other embodiments, the opening 910 in the baffle 909 may have widths ranging from 0.1 to 5 mm.

In certain embodiments, the baffle 909 takes the form of a grating 908 comprising a plurality of openings 910 that are configured to prevent phase change material that has not undergone a phase change from moving from the upper chamber 904 to the lower chamber 906. In this non-limiting example, the openings 910 are configured to permit PCM 902a in a liquid state or a gel state to pass from one chamber 904 to another chamber 906, while also preventing still unmelted or only partially melted portions of PCM 902 exceeding a predetermined size or viscosity from passing therethrough. The number of openings and size of the openings is not particularly limited, so long as the size and number of openings is tuned for PCM 902 to the desired rate of mass transfer. Furthermore, the openings in the grating may be uniform or non-uniform, i.e., the openings in one part of the grating may be different from the openings in the other part of the grating.

Furthermore, the grating 908 can be horizontal or may be disposed at an angle that is not horizontal, (as shown in FIG. 51A) in order to facilitate melted PCM 902b in passing through the openings 910. In particular, the grating 908 can include a top surface that extends from the housing 903 by a non-perpendicular angle, such that the force of gravity can pull the melted PCM 902b across the top surface of the grating before the PCM 902b flows through one of the openings 910. It is contemplated that the other embodiments, may include components oriented at any angle. For example, the plate or screen may also be oriented at an angle in the same way as the grating described herein.

As shown in FIG. 51B, the slanted grating 908 is a planar wall comprising a plurality of openings 910 and disposed in a non-horizontal position, to prevent un-melted particles of PCM 902 from transferring from the upper chamber 904 through the openings 910 to the lower chamber 906. The slanted grating 908 can reduce the amount of fully melted PCM 902 that adheres to the grating 908 thus providing a comparably higher mass transfer than that with a horizontal grating. The openings 910 may also include chamfers, lead-ins, radius and the like to further facilitate fully melted PCM 902 to pass through openings 910 while reducing the amount that adheres to the grating. In another example, multiple gratings (not shown) symmetrically spaced above and below the center grating 908 can be included. These multiple gratings can also have different shaped and/or sized openings, similar to openings 910, to further regulate or stratify the size of the un-melted PCM that transfers from the upper chamber toward the lower chamber.

Referring to FIG. 51C, another embodiment of the PCM notification device 5000 can have components, which are substantially similar to the components of the PCM notification device shown in FIG. 51A. The PCM notification device 5000 includes a baffle 909' comprising a plate 5008 defining a single opening 5010 for preventing a bulk portion of the phase change material, exceeding a predetermined size and that has not undergone a phase change, from moving from the upper chamber 5004 to the lower chamber 5006. The size of opening 5010 may be advantageously selected to prevent PCM in the solid state from passing from the upper chamber to the lower chamber.

Referring to FIGS. 52A-52F, another example of the PCM notification device 900' can have components, which are substantially similar to the components of the PCM notification device shown in FIGS. 51A and 51B and are identified by the same reference numbers followed by a single prime symbol ('). However, while the PCM notification device 900 comprises the grating 908 and multiple openings 910 for communicating the upper and lower chambers 904, 906 with one another, the PCM notification device 900' comprises a cylindrically shaped hourglass configuration including single tuned orifice 910' through which all of the fully melted PCM 902b must pass, thus requiring that any unmelted PCM 902a, which blocks the orifice 910', to melt before the entire amount of PCM 902a transfers from one chamber 904' to the other chamber 906'. While the PCM notification device 900 of FIGS. 51A and 51B include the baffle in the form of the grating 908, the PCM notification device 900' includes a baffle 909" in the form of a tapered passage formed by the walls of the housing that is in fluid communication between the upper chamber 904' and the lower chamber 906'.

Referring to FIGS. 52B-52F, the PCM notification device 900' includes transparent window 912', which allows the HCP to assess how much PCM is in the upper chamber and/or the lower chamber of the PCM notification device. The transparent window 912' may comprise one or more markings 913', 913", 913'" to allow the HCP to compare the amount of PCM in the upper chamber 904' and/or the lower chamber 906' of the PCM notification device to one or more predetermined levels. It should be appreciated any configuration of the PCM notification devices described above may include one or more of the markings described below.

Figure 52A:
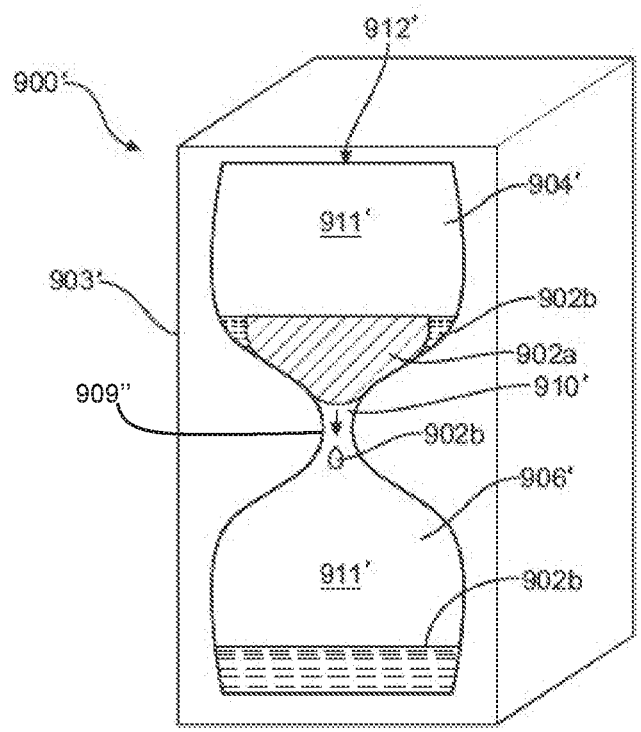
FIGS. 52A-52F are various cross-sectional views of still another exemplary PCM notification device, illustrating the PCM notification device comprising an hourglass configuration with a single tuned orifice, and the PCM in various positions.
Figure 52B:
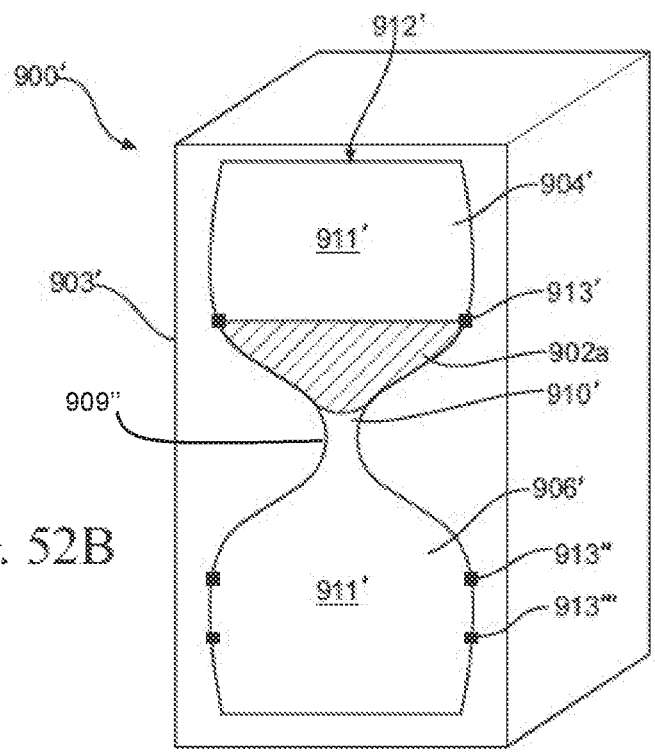
Figure 52C:
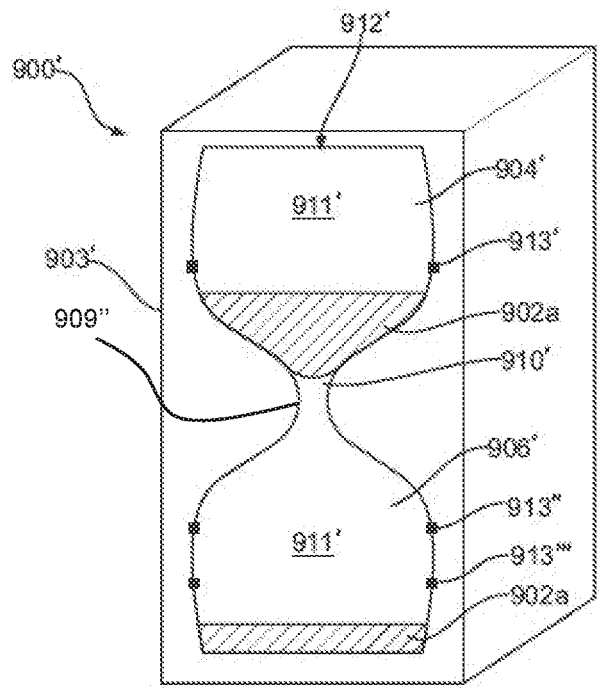

In one embodiment, referring to FIGS. 52B and 52C, the PCM notification device 900' may include a ready state marking 913' on the upper chamber 904' correspond to a 'ready' state. Thus, if the PCM 902a is present in the amount in the upper chamber 904' to reach the ready state marking 913', the HCP can confirm that the PCM notification device 900' is ready to be used (See FIG. 52B), after for example the PCM notification device 900' had already been used such that at least a portion of the PCM 902a previously transferred from the upper chamber 904' to the lower chamber 906'. If the PCM 902a is not present in the upper chamber 904' in the amount sufficient to reach the ready state marking 913', the HCP can determine that the PCM notification device 900' needs to be reset before it is ready to be used (See FIG. 52C). As can be seen in FIG. 52C, the solid PCM in the upper chamber 904' is not at a level that reaches the ready state marking 913', as there is some solid PCM 902a remaining in the lower chamber 906'. In one embodiment, the PCM notification device 900' can be placed in a sterilizer to be reset, or otherwise heated, such that enough PCM is in the upper chamber 906 to reach the ready state marking 913'.

Once the HCP confirms that the PCM notification device 900' includes enough PCM 902a in the upper chamber 904' to be in the ready state, the PCM notification device 900' and sterilization enclosure are placed in the sterilizer for the desired sterilization cycle. Once the sterilization cycle is complete, the HCP can inspect the PCM notification device 900' to confirm what amount of PCM has been actually transferred to the lower chamber of the PCM notification device, and whether that amount of PCM corresponds to the desired level of sterility. To aid in this confirmation, referring to FIGS. 52D-52F, the PCM notification device 900 may further comprise one or more markings 913", 913'" corresponding to threshold process conditions that are indicative of desired sterility levels. More particularly, each volumetric marking may correspond to a given amount of heat transferred to the PCM during the sterility cycle. These amounts of heat transfer may correspond to process conditions which have been validated to achieve the desired sterility levels. The sterility markings 913", 913'" may coincide with the transparent window 912' on the lower chamber 906' of the PCM notification device 900'.

In one exemplary configuration, the lower chamber 906' of the PCM notification device 900' may include a first sterility marking 913" corresponding to a 6-log reduction in micro-organisms, and a second sterility marking 913'" corresponding to a 3-log reduction in micro-organisms. When the HCP removes the sterilization container and the corresponding PCM notification device 900' from the sterilizer after the cycle has been completed, the HCP visually inspects the PCM notification device 900' to confirm how much of the PCM 902b is present in the lower chamber 906', i.e., how much PCM melted and transferred from the upper chamber 904' to the lower chamber 906' during the sterilization cycle. If the amount of PCM 902b in the lower chamber 906 corresponds to the first sterility marking 913" or the second sterility marking 913'", the HCP can confirm that the surgical instruments have been exposed to the threshold process conditions that are indicative of the desired level of sterility. Of course, it is contemplated that any number of sterility markings could be included. Furthermore, it is also contemplated that the both the upper chamber 904' and the lower chamber 906' can include the ready marking 913' and the sterility markings 913", 913'", which enables the HCP to avoid the need to re-melt the PCM before the PCM notification device can be re-used.

Referring specifically to FIG. 52C, after the sterilization cycle is completed, the HCP can inspect the PCM notification device 900' and determine that the amount of PCM in the lower chamber 906' does not reach the first sterility marking 913", nor the second sterility marking 913'". Based on the level of PCM as compared to the sterility markings 913", 913'", the HCP can determine that the sterilization container has not been exposed to the threshold process conditions that have been validated to achieve the desired sterility levels.

Figure 52D:
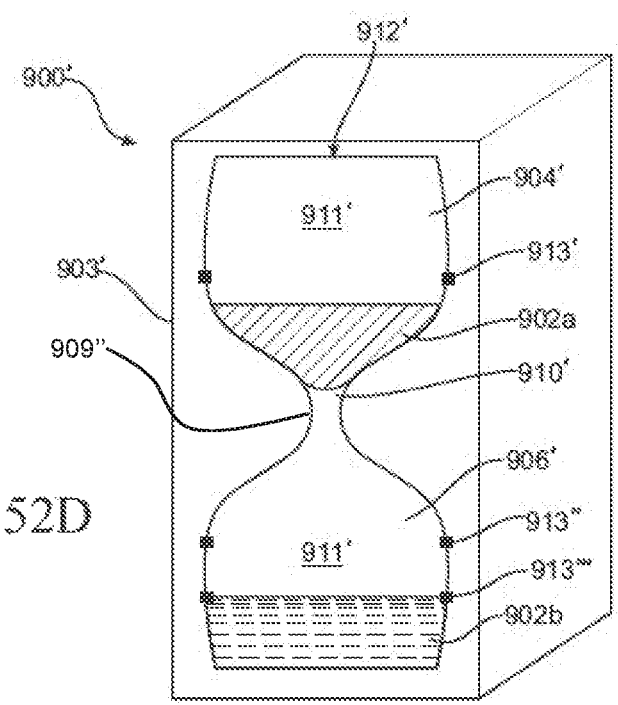
Figure 52E:
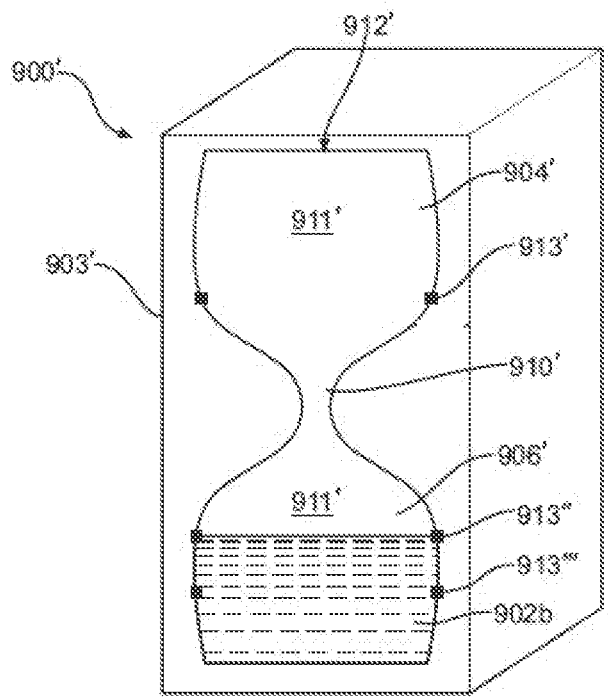

Referring to FIG. 52D, after the sterilization cycle has been completed, some solid PCM 902a remains within the upper chamber 904'. However, the amount of PCM present in the lower chamber 906' is sufficient such that the level of PCM in the lower chamber 906' reaches the second sterility level 913'", a 3-log reduction. This allows the HCP to confirm that the instruments have been exposed to threshold process conditions, such as those process conditions that have been validated to achieve the desired level of sterility without opening the container Referring to FIG. 52E, after the sterilization cycle has been completed, all of the PCM 902a in the PCM notification device 900' is present in the lower chamber 906', and no detectable amount of PCM remains in the upper chamber

904'. Furthermore, the level of PCM 902b in the lower chamber 906' corresponds to the first sterility marking 913", corresponding to a 6-log reduction of microorganisms.

Figure 52F:
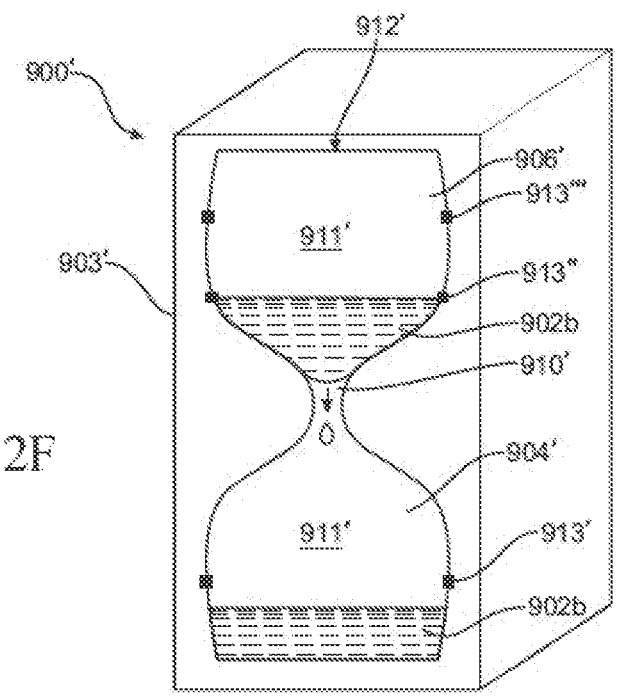

Referring now to FIG. 52F, the PCM notification device 900' may be reset by rotating or otherwise positioning the housing 903 such that the lower chamber 906' is above the upper chamber 904'. Once the PCM notification device 900' is situated in this manner and the PCM notification device 900' is exposed to a sufficient amount of heat, the liquid PCM 902b can flow from the lower chamber 906' to the upper chamber 904'. Thus, when the PCM notification device 900' is next used by the HCP, there will be enough PCM 902 in the upper chamber 904' to correspond to the ready state marking 913'.

In one specific example, the PCM notification device 900' could be thermodynamically sized to allow 12 cc of PCM 902a to melt and flow into the lower chamber 906' when PCM notification device 900' is surrounded by 100% saturated steam at 133° C. for 3 minutes, and further allows 16 cc of PCM to melt into the lower chamber 906' when the PCM notification device 900' is exposed to 100% saturated steam at 133° C. for 4 minutes. In this example, each one of the transparent windows 912 can include at least one marking or the plurality of graduated markings to indicate the amount of volume and thus the corresponding time the PCM notification device was exposed to a certain steam state for a certain amount of time, e.g. 12 cc marking for 3 minute exposure and 16 cc marking for 4 minute exposure time.

The number and placement of graduated markings on the upper and lower chambers is not particularly limited. It should be appreciated that such markings allow the HCP to confirm whether the desired type of steam sterilant and duration of exposure has been achieved in a simple manner that is not prone to error. In certain embodiments, the HCP can determine that certain process conditions have been achieved by seeing the volume of the PCM that is present in the lower chamber as compared to the sterility markings. This is in contrast to methods which would require the HCP to determine whether the PCM has changed color or transparency, which can be prone to error depending on the light levels in the area in which the PCM is inspected.

As described above with reference FIG. 52F, but now referring to FIG. 51A-C, another benefit of the PCM notification device 900 is that it can be reused after the entire amount of PCM 902 has transferred to the lower chamber 906 and PCM 902 has returned to an unmelted state, by rotating the PCM notification device 900 upside down, such that the force of gravity and exposure to threshold steam conditions can return or transfer fully melted PCM 902 from one end of the housing to the opposing end of the housing. Then, once cooled, the PCM in the solid state will be located in the opposite chamber, which is in this example the upper chamber of the PCM notification device.

As described above, the housing 903 of the PCM device can be rotatably mounted to the interior container. In one embodiment, the PCM device may be rotatably mounted through the circular boss 918 with the boss axis centered on the exterior housing 903 as shown in FIG. 50A. This boss in cooperation with complimentary features mounted to container side panels can facilitate the rotation of PCM notification device 900 180° around the circular boss 918 axis and position it in a ready state to be reused. The housing 903 can have any suitable shape that permits the force of gravity to transfer PCM 902 that has undergone a phase change from one portion of the housing to another portion of the housing. While the present example of the housing 903 comprises a rectangular prism including the slanted grating, it is contemplated that the grating may be horizontal and/or the housing can have other suitable shapes.

Housing 903 components, chamber 904, chamber 906 and grating 908 can be constructed from the same material or from different materials having corresponding coefficients of thermal conductivity, such that the PCM indicator 900 can be configured to indicate sterilization process conditions for various instruments and/or containers. For example, a portion of the housing 903 defining the walls adjacent to the grating 908 can be made from a material having a higher coefficient of thermal conductivity than that of the portion of the housing 903 defining the upper chamber 904 that has a relatively slow heat transfer rate $Q'$ through the chamber 904, which in turn can have a coefficient of thermal conductivity that is higher than that of the portion of the housing 903 defining the lower chamber 906. However, it is contemplated that various combinations of any parts of the PCM indicator 900 can have higher or lower coefficients of thermal conductivity relative to one another. In another example, one or more layers of known suitable walls and the grating can be made from a material that has a relatively high heat transfer rate $Q$ through the walls.

Optional insulation materials (not shown), which have coefficients of thermal conductivity that are higher or lower relative to one another, can be attached to one or more portions of the housing 903. The insulation materials can provide a very slow heat transfer rate $Q''$ through the outside surfaces of the PCM housing 903 so as to change the amount of external surface area S where relatively high heat transfer rate can occur. In one example, all portions of the housing 903 may be made of the same material having the same coefficient of thermal conductivity, and the portion of the housing 903 adjacent to the grating 908 may not include any layers of insulation material.

The portion of the housing 903 defining the upper chamber 904 can be made of a material having a coefficient of thermal conductivity that is higher than that of an insulation layer covering the portion of the housing 903 that defines the lower chamber 906. The insulation layers can overlap one another, be spaced apart from one another, or be arranged in any suitable configuration to regulate the rate of heat transfer through the housing assembly to the PCM 902. These construction details, combined with the PCM 902 material thermodynamic properties, allows the PCM notification device to be specifically sized and built to create a repeatable thermodynamic notification system wherein a known amount of PCM material 902 melts and thus flows into the lower chamber as a function of time for targeted steam sterilization conditions. The PCM device housing can be a sealed housing assembly so that the PCM and the void space 911 surrounding the PCM is sealed within the housing with properties and a volume that remain constant throughout the useful life of the PCM device. Another advantage of sealing the housing assembly is to prevent ingress of pressurized fluids of the sterilization process from entering the interior and contaminating the PCM or causing the PCM to change its calibrated response to heat energy and temperature changes.

The PCM notification device 900 can be disposed at a location to which the flow or propagation of the sterilant gas is impeded thus increasing the threshold by which the PCM notification device 900 determines when the sterilization process conditions have been achieved. In particular, the PCM notification device may replace or be joined with the PI 57' at a bottom end of the air challenge cannula 51". In other examples, the PCM notification device 900 can be disposed within the container. In particular, the PCM notification device 900 may replace or be used in conjunction with the PI 57' inside of the container, such that the PCM notification device 900 is disposed within the container and visible through one or more transparent windows 53, 53' (see FIG. 39). The HCP can read the PCM notification device 900 through the window 53 without opening the container. In this example, the PCM notification device can be manually reset, by turning it 180° upside down, for reuse through the open lid prior to sealing the lid to the container base and entering the sterilization chamber. However, in still another example, the PCM notification device 900 can be placed adjacent to the outer wall of the container, such that a user can read the PCM notification device 900 without having to view the same through the transparent window 53. In such an example, at least a portion of the PCM notification device 900 is exposed to the sterilant gas within the container.

Figure 53:
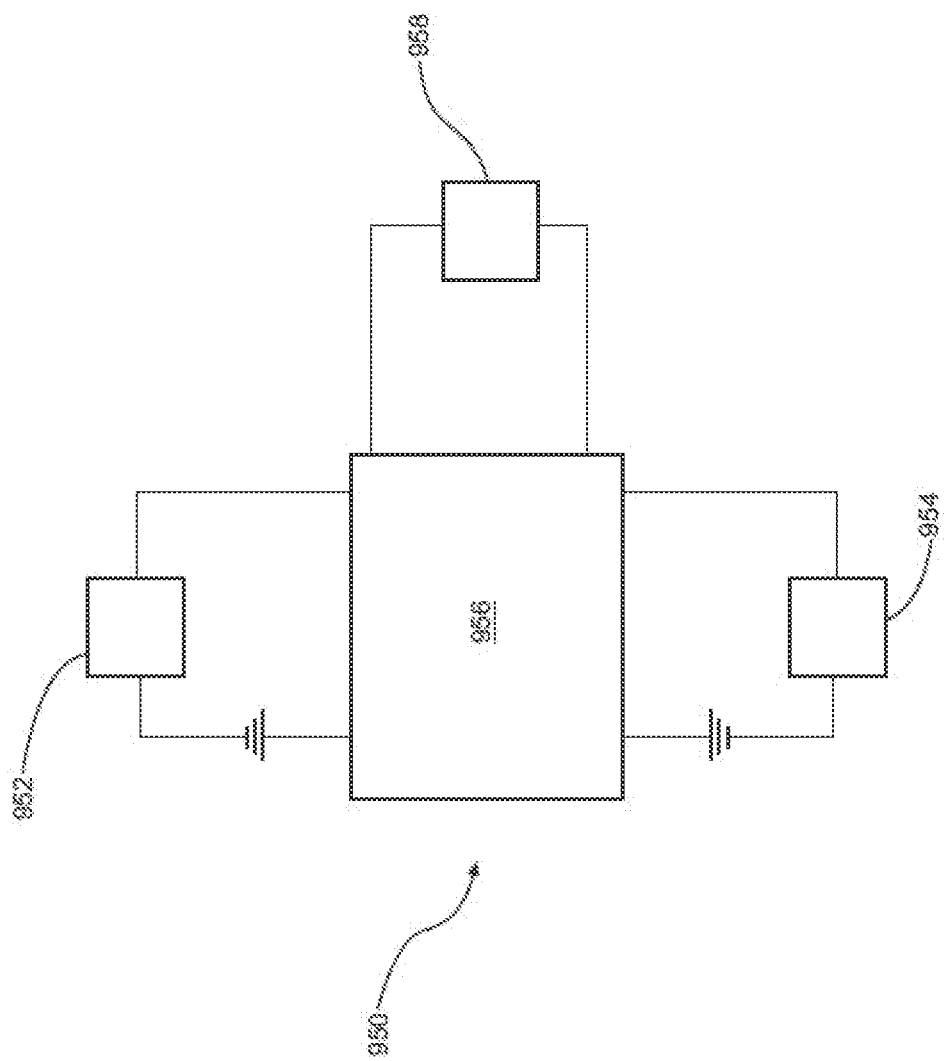
FIG. 53 is a schematic diagram of another exemplary sensor module, illustrating the sensor module configured to measure the speed of sound through the sterilant gas within the container.

Referring to FIG. 53, a sound sensor 950 can be used in addition to or for replacement of the sensor components described above that are used to measure steam saturation characteristics to determine whether threshold process conditions have been met or exceeded to ensure that the desired level of sterilization has been achieved. The sound sensor 950 can be configured to monitor the speed of sound through an interior of the container to determine the steam saturation state. Based on the speed at which sound travels through the interior, the sound sensor 950 can determine the conditions present in that interior. Among other things, sound travels through steam at different speeds depending on the degree of saturation of that steam. For example, sound travels through 100% saturated steam faster than 50% saturated steam. In particular, one example of the sound sensor 950 can include a first piezoelectric emitter 952 configured to emit acoustic waves (sound) at a select frequency and a complementary piezoelectric receiver 954 spaced apart from the emitter by a known distance, such that a processor 956 can determine the speed of the sound based upon the elapsed time from when the sound travels across the known distance from the emitter 952 to the receiver 954. This type of sensor assembly is applicable because the speed of sound in a void can vary as a function of the concentration of a gas in the void. In this example, the speed of sound in the container correlates directly with the concentration of steam (water vapor) within the container. The processor 956 can send a signal to a notification device 958 to communicate the characteristics within the container during the sterilization process and/or the status of the container and/or the instruments therein, based on the speed of sound within the container. The signals sent between the components of the sound sensor 950 can be accomplished by wired or wireless transmission. Further, the notification device 958 can be any one or more of the notification devices, as described above, or additional notification devices.

Other types of sensors are also contemplated. For instance, it is contemplated that other types of electromagnetic sensing configurations are also possible that can measure the speed of transmission of certain types of waves across the interior, including but not limited to, radiofrequency waves.

Figure 54A:
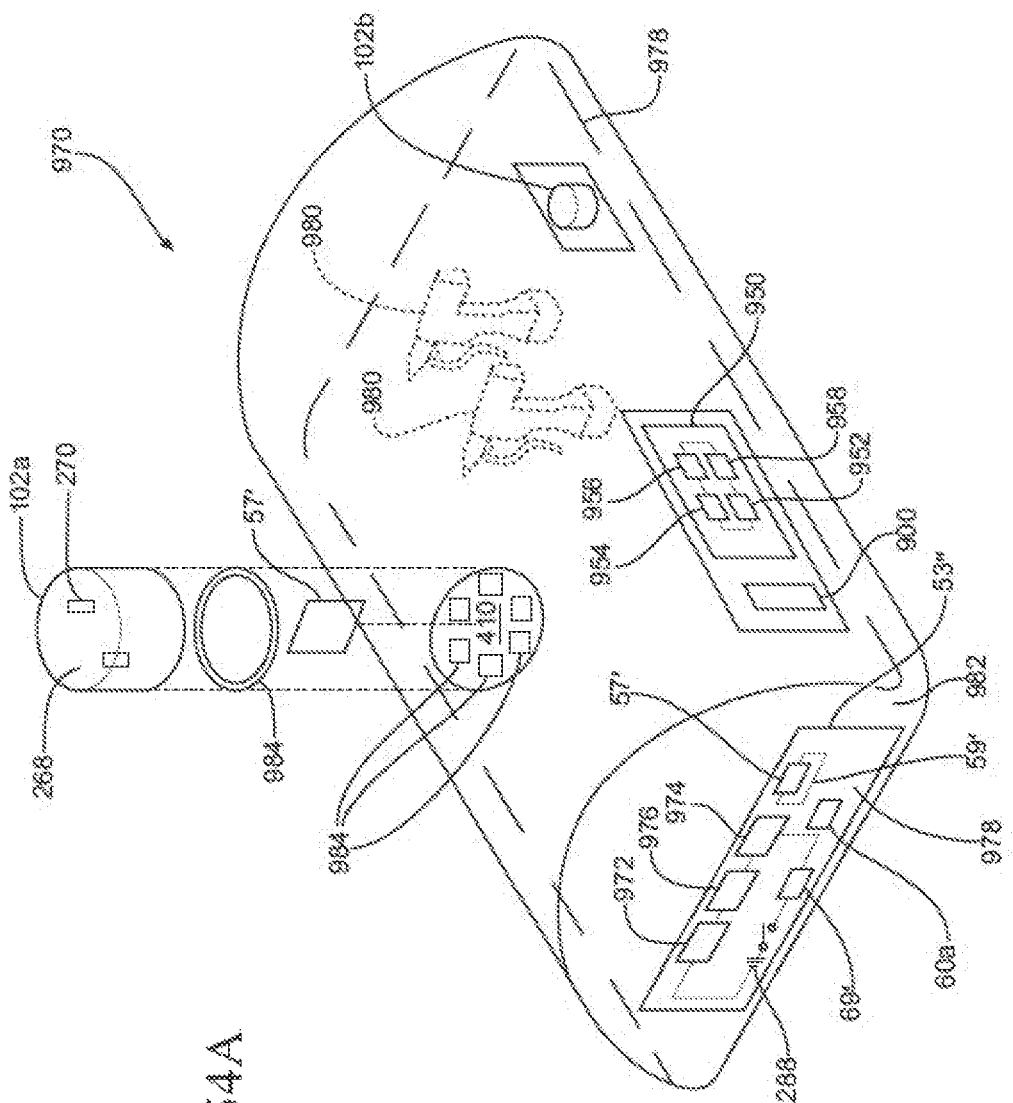
FIG. 54A is a perspective view of another exemplary sterilization enclosure, illustrating the enclosure comprising a tray and a sterile barrier wrap.

Referring to FIGS. 54A and 54B, another exemplary sterilization container 970 can include one or more sensors 972, notification devices 974, and a processor 976, which are similar to any one of those integrated within the first and second exemplary sterilization containers 50, 430. While each one of the sterilization containers 50, 430 of FIGS. 1 and 21 comprises a rigid body and a lid coupled to the body, this exemplary container 970 comprises a tray 978 or perforated enclosure configured to have one or more instruments 980 disposed thereon/therein and a sterile barrier wrap 982, which is an anti-microbial barrier wrapped around the instruments 980 and/or the tray 978 or perforated enclosure so as to enclose the contents in the sterile barrier wrap 982. Sterile barrier wrap 982 may have similar properties to filter medium 410, which allows sterilant fluids (liquids and/or gases) to penetrate the wrap into the enclosure formed by the wrap, but maintain the microbial level of the enclosed instrumentation by keeping microbes and microorganisms from passing through the wrap. Furthermore, any one or more of the sensors, notification devices, and processors can be disposed within the container underneath the wrap, disposed external to the container, and/or coupled to an airflow challenge cannula. Similar to the container 430" of FIG. 42A comprising the transparent window 53' and an LED 69' disposed within the container 430" to permit the HCP to see the instruments and the notification devices therein, the wrap 982 can have a transparent window 53" to permit the HCP to see the instruments 980 and the notification devices 974 underneath the sterile barrier wrap 982. Moreover, while the notification devices 974 comprise PIs, electronic sensors, mechanical sensors, and PCM notification devices, the container 970 can have any one suitable notification device or combinations thereof, such as those described above.

As best shown in FIG. 54A, the container 970 can comprise two of the PIs 57' described above. In one example, a first PI 57' can be disposed within the container 970 and underneath the wrap 982. In particular, the container 970 can comprise a holder 59' coupled to the tray 978 and/or the wrap 982, and the holder 59' can be configured to hold the first PI 57' within the container 970. The holder 59' can comprise a mounting bracket, a pocket, or any other suitable seat for the first PI 57' in a location, such that the first PI 57' is visible through the transparent window 53" and it can be read without removing the wrap 982 from the tray 978 that would potentially expose the instruments 980 to contaminants. However, it is contemplated that the holder 59' can hold the first PI 57' in any suitable location within the container 970, particularly for examples of the container that do not include the transparent window.

The container 970 can further comprise a second PI 57' that is removably attached to an external surface of the container 970. In particular, any one or more of the wrap 982, the tray 978, the second PI 57', or a sensor module containing the second PI 57' can comprise one or more mounting mechanisms 984, that removably attach the second PI 57' to the external surface of the wrap 982, such that the second PI 57' can be read to determine the sterilization process conditions of the container 970. The HCP can verify the status of the second PI 57' by reading the first PI 57' through the transparent window 53'. However, in an example of the container 970 that does not have the transparent window, the second PI 57' can be read at or near the completion of the sterilization process, and the first PI 57' can be read to confirm sterilization process conditions when the wrap 982 is removed from the tray 978 within the sterile operating room.

The mounting mechanism that attaches the second PI 57' can comprise magnetic fasteners to allow the HCP to attach and remove the second PI 57' as needed. However, other types of temporary fasteners may be utilized to attach the PI 57' or other notification device to the outside of the wrap, such as an adhesive, may also be utilized. This allows the user to determine the status of the container without disrupting the sterile barrier.

The container 970 can further comprise two of the sensor modules 102a, 102b having components that are similar to those of the sensor module 102 of FIG. 3 or those of the sensor module 570 of FIG. 21, as described above. One of the sensor modules 102a can be disposed underneath the wrap 982 and within the container 970, and the other sensor module 102b can be coupled to the external surface of the wrap 982 and/or tray 978. The sensor modules 102a, 102b can communicate with one another by wireless transmission and/or by wired transmission. For wireless transmission, the sensor modules 102a, 102b can have corresponding transceivers for sending and receiving signals between each other. For wired transmission, the sensor modules 102a, 102b can communicate with one another through one or more conductors (not shown) aseptically extending through the wrap 982 and/or the tray 978. Either one or both of the sensor modules 102a, 102b can further comprise the processor 384 and the LEDs 268, 270 to communicate the sterilization process conditions of the container.

The PI 57' can be removably coupled to the container 970 and fluidly communicate with the container 970, which in this form can be the portion of the sterile barrier wrap 982 upon which the PI 57' is mounted. However, it is contemplated that the wrap can comprise an opening and a separate filter medium coupled to the wrap so as to sealingly cover the opening. While in one example, the PI 57' can be coupled directly to the wrap, it is contemplated that the PI 57' can be disposed within a sensor module that is in turn coupled to the wrap, such that the PI 57' is disposed outside of the container 970 and communicates with the interior of the same.

The filter medium 410 can challenge or impede the flow of sterilant gas from the container to the PI 57', thus providing a comparably higher threshold for evaluating the sterilization process conditions than a PI 57' disposed within the container.

Any one or more of the notification devices that are used to communicate the sterilization process conditions of the container, as described above, can be integrated within the container 970 to alert the HCP of the location of the container with a sterile inventory room and further communicate the status of its contents. As one example, the notification device used to notify the HCP of the location of the container can be the same LEDs 268, 270 used to indicate the sterilization status of the container.

The alternative examples described herein may have less than all of the described features. Further, features of the different versions separately described herein may be combined to form additional examples. For instance, the sensors that measure sterilant concentration as a function of absorbed light may be built into any one or more of the sensor modules described herein. Furthermore, the sensors may be stand-alone devices disposed within the container and/or disposed outside of the container but that fluidly communicate with the interior of the container.

Accordingly, it is to be understood that the above description is intended to be illustrative and not restrictive. Many examples and applications other than the examples provided would be apparent upon reading the above description. It is anticipated and intended that future developments will occur in the technologies discussed herein, and that the disclosed systems and methods will be incorporated into such future examples. In sum, it should be understood that the application is capable of modification and variation.

Embodiments of the disclosure can be described with reference to the following numbered clauses, with specific features laid out in the dependent clauses:

I. A sterilization enclosure configured to be placed within a sterilizer, the sterilization enclosure configured to accommodate a surgical instrument for sterilization and defining an interior capable of fluidly communicating with the sterilizer to receive steam from the sterilizer, the sterilization enclosure comprising:
 a phase change material notification device positioned within the interior of said enclosure, said phase change material notification device comprising:
  a housing defining an upper chamber and a lower chamber;
  a phase change material positioned within said upper chamber and configured to undergo a phase change and move from said upper chamber to said lower chamber; and
  a baffle positioned between said upper chamber and said lower chamber to allow said phase change material to move from said upper chamber to said lower chamber when a threshold amount of heat energy has been transferred to the phase change material from the steam of the sterilizer adjacent to said phase change material notification device.

II. The sterilization enclosure of clause I, wherein said phase change material notification device is rotatably coupled to said enclosure.

III. The sterilization enclosure of any of the preceding clauses, wherein said phase change material notification device is rotatably coupled to said enclosure to position said upper chamber above said lower chamber.

IV. The sterilization enclosure of any of the preceding clauses, wherein said enclosure comprises a transparent window through which at least a portion of said phase change material within said phase change material notification device is visible.

V. The sterilization enclosure of clause IV, wherein said enclosure comprises a container including a body and a lid coupled to said body, with at least one of said body and said lid having said transparent window integrated therein.

VI. The sterilization enclosure of clause IV, wherein said enclosure comprises a sterile barrier wrap having said transparent window integrated therein.

VII. The sterilization enclosure of clause VI, wherein said sterile barrier wrap comprises an anti-microbial barrier.

VIII. The sterilization enclosure of any of the preceding clauses, wherein said housing comprises a marking corresponding with at least one of said upper chamber and said lower chamber to indicate an amount of said phase change material located within a corresponding one of said upper chamber and said lower chamber.

IX. The sterilization enclosure of any of the preceding clauses, wherein said baffle comprises an aperture, a longitudinal slot, or a combination thereof, independently configured to prevent said phase change material that has not undergone said phase change from moving from said upper chamber to said lower chamber.

X. The sterilization enclosure of any of the preceding clauses, wherein said baffle comprises a plate, a screen, a grating, or a combination thereof.

XI. The sterilization enclosure of clause X, wherein said baffle prevents a bulk portion of said phase change material that has not undergone said phase change from moving from said upper chamber to said lower chamber.

XII. The sterilization enclosure of clause X, wherein said baffle comprises a top surface and extends within a housing interior by a non-perpendicular angle such that gravity allows a portion of said phase change material to move along said top surface before passing through.

XIII. The sterilization enclosure of any of the preceding clauses, wherein said baffle is configured to allow said phase change material to pass therethrough when at least of a portion of said phase change material is in a gel state, a liquid state, a viscous state, or a combination thereof.

XIV. The sterilization enclosure of any of the preceding clauses, wherein said phase change material is capable of undergoing a reversible phase change.

XV. The sterilization enclosure of any of the preceding clauses, wherein said phase change material is configured to melt within a range of a temperature point.

XVI. The sterilization enclosure of any of the preceding clauses, such that said phase change material that has undergone said phase change is capable of moving from said upper chamber to said lower chamber in response to the force of gravity.

XVII. The sterilization enclosure of any of the preceding clauses, wherein said phase change material notification device further comprises an insulation layer coupled to said housing.

XVIII. The sterilization enclosure of any of the preceding clauses, wherein said housing of said phase change material notification device comprises a transparent window through which at least a portion of said phase change material is visible.

XIX. The sterilization enclosure of any of the preceding clauses, wherein said baffle is a tapered passage in fluid communication between said upper chamber and said lower chamber.

XX. A sterilization enclosure configured to be placed within a sterilizer, the sterilization enclosure for accommodating a surgical instrument for sterilization and defining an interior capable of fluidly communicating with the sterilizer to receive steam from the sterilizer, the sterilization enclosure comprising:
  a phase change material notification device coupled to said enclosure, said phase change material notification device comprising:
    a housing defining an upper chamber and a lower chamber;
    a phase change material positioned within said upper chamber and configured to undergo a phase change and move from said upper chamber to said lower chamber; and
    a baffle positioned between said upper chamber and said lower chamber to allow said phase change material to move from said upper chamber to said lower chamber when a threshold amount of heat energy has been transferred to the phase change material from the steam of the sterilizer adjacent to said phase change material notification device.

XXI. The sterilization enclosure of clause XX, wherein said phase change material notification device is positioned within said interior of said enclosure.

XXII. The sterilization enclosure of clause XX, wherein said phase change material notification device is positioned external to said interior of said enclosure.

XXIII. The sterilization enclosure of clause XX, wherein said enclosure comprises a container, and said container defines an opening, and said phase change material notification device is aseptically received within said opening and coupled to said enclosure to sealingly block said opening.

XXIV. A phase change material notification device adapted for use with a sterilization enclosure configured to be placed within a sterilizer, the sterilization enclosure configured to accommodate a surgical instrument for sterilization and defining an interior capable of fluidly communicating with the sterilizer to receive steam from the sterilizer, the phase change material notification device comprising:
  a housing defining an upper chamber and a lower chamber;
  a phase change material positioned within said upper chamber and configured to undergo a phase change and move from said upper chamber to said lower chamber;
  a marking corresponding with at least one of said upper chamber and said lower chamber to indicate an amount of said phase change material located within a corresponding one of said upper chamber and said lower chamber; and
  a baffle positioned between said upper chamber and said lower chamber to allow said phase change material to move from said upper chamber to said lower chamber,
  wherein said marking corresponds to a volume of phase change material that is indicative of a threshold amount of heat energy being transferred to the phase change material from the steam of the sterilizer adjacent to the phase change material notification device, the threshold amount of heat energy correlated to a desired level of sterility.

XXV. A method for detecting a desired level of sterilization of a sterilization enclosure placed within a sterilizer, the method comprising:
  placing the sterilization enclosure and a phase change material notification device within the sterilizer, the phase change material notification device comprising a housing that defines an upper chamber and a lower chamber, and a phase change material positioned in the upper chamber;
  transferring steam energy from the sterilizer to the phase change material notification device to change a phase of at least a portion of the phase change material to enable the phase change material to move from the upper chamber to the lower chamber;
  resetting the phase change material notification device by rotating the housing relative to the sterilization enclosure.

XXVI. A sterilization enclosure to be placed within a sterilizer, and the sterilization enclosure having an interior for accommodating at least one surgical instrument and maintaining sterility of the at least one surgical instrument after the sterilization enclosure is removed from the sterilizer, the sterilization enclosure comprising:
  an interior and a transparent window; and
  a light source coupled to said enclosure to illuminate said interior and the at least one surgical instrument positioned within said interior, such that said interior and the at least one surgical instrument are visible through said transparent window.

XXVII. A method for retrieving a sterilization enclosure containing a desired surgical instrument, the method comprising:
  inputting a retrieval command into a user interface, said retrieval command corresponding to the desired surgical instrument for retrieval;
  transmitting a retrieval signal corresponding with said retrieval command from said user interface to a controller that is coupled to a database, said database having stored therein a plurality of reference retrieval commands and a corresponding plurality of reference code signals, each of said reference code signals being indicative of a enclosure and a surgical tool contained therein; and
  determining a coded signal corresponding with said retrieval command;
  transmitting said coded signal to a receiver coupled to the sterilization enclosure; and
  actuating a notification device coupled to the sterilization enclosure in response to said receiver receiving said coded signal, such that said notification device indicates a location of the sterilization enclosure containing the desired surgical instrument.

XXVIII. The method of clause XXVII wherein actuating said notification device comprises illuminating a light source coupled to the sterilization enclosure.

XXIX. The method of any one of clauses XXVII and XXVIII, further comprising illuminating a light source positioned within the interior of the sterilization enclosure.

XXX. The method of any of clauses XXVII, XXVIII, and XXIX wherein the sterilization enclosure further includes a transparent window, said method further comprising verifying contents positioned within the interior of the sterilization enclosure by looking through the transparent window.

XXXI. The method of any of clauses XXVII, XXVIII, and XXIX wherein the sterilization enclosure further includes a transparent window and a process indicator, said method further comprising verifying a status of the process indicator positioned within the interior of the sterilization enclosure.

XXXII. The method of any of clauses XXVII through XXXI further comprises illuminating a light source positioned external to said interior of the sterilization enclosure.

XXXIII. The method of any of clauses XXVIII, XXIX, and XXXII further comprises flashing said light source on and off.

XXXIV. The method of any of clauses XXVII through XXXIII wherein transmitting said coded signal comprises transmitting said coded signal to an RFID tag coupled to the sterilization enclosure.

XXXV. The method of any of clauses XXVII through XXXIV, further comprising placing a surgical instrument within the interior of the sterilization enclosure and sterilizing the sterilization enclosure, wherein the surgical instrument does not include a RFID tag associated therewith.

XXXVI. A sterilization container configured to be placed in a sterilizer, and maintaining sterility of the at least one surgical instrument after the sterilization container is removed from the sterilizer, the sterilization container having an interior and permitting a sterilant gas to flow from the sterilizer into the interior, the sterilization container comprising:
  at least one wall defining an interior;
  a filter frame positioned within the interior, said filter frame configured to hold a filter medium in the interior and against said wall; and
  a sensor coupled to said filter frame and adapted to sense a characteristic of the sterilant gas within the interior.

XXXVII. The sterilization container of clause XXXVI, wherein said sensor is at least one of a gas concentration sensor, a temperature sensor, a pressure sensor, a sound sensor, and an electromagnetic wave transmission sensor.

XXXVIII. The sterilization container of any of clauses XXXVI and XXXVII, wherein said sensor comprises said gas concentration sensor.

XXXIX. The sterilization container of any of clauses XXXVII and XXXVIII, wherein said gas concentration sensor comprises an optical sensor assembly configured to detect a concentration of the sterilant gas.

XL. The sterilization container of clause XXXIX, wherein said optical sensor assembly comprises:
  a light source and a photodetector coupled to a first portion of said filter frame;
  a prismatic reflector coupled to a second portion of said filter frame, where said first portion and said second portion are on diametrically opposite sides of said filter frame.

XLI. The sterilization container of any of clauses XXXVI through XL, wherein said container comprises a plurality of walls, a floor, and a lid, and at least one of said walls, said floor, and said lid defines an aperture permitting the sterilant gas to flow from the sterilizer and into the interior.

XLII. The sterilization container of clause XLI, wherein said filter frame presses said filter medium against at least one of said walls, said floor, and said lid and adjacent to said aperture.

XLIII. A filter module adapted for attachment to a sterilization container configured to be placed in a sterilizer, and maintaining sterility of the at least one surgical instrument within an interior of the sterilization container after the sterilization container is removed from the sterilizer, the lid assembly adapted to enclose the interior of the sterilization container and permit a sterilant gas to flow from the sterilizer into the interior, the filter module comprising:
  a filter medium;
  a filter frame for attachment to the sterilization container and configured to hold said filter medium against said enclosure; and
  a gas concentration sensor coupled to said filter frame and arranged such that, when said filter frame is coupled to the sterilization container, said gas concentration sensor is adapted to sense a concentration of the sterilant gas adjacent to said filter frame.

XLIV. The filter module of clause XLIII, wherein said filter medium is retained by said filter frame.

XLV. The filter module of any of clauses XLIII and XLIV, wherein said filter frame presses said filter medium against said sterilization container adjacent to an aperture formed in the sterilization container.

XLVI. The filter module of any of clauses XLIII through XLV, wherein the sterilization container comprises a plurality of walls, a floor, and a lid, and said aperture are formed in at least one of said plurality of walls, said floor, and said lid.

XLVII. The filter module of any of clauses XLII through XLVI, wherein said gas concentration sensor comprises an optical sensor configured to detect a concentration of the sterilant gas.

XLVIII. A sterilization container adapted for placement within a sterilizer and having an interior, the sterilization container configured to hold a surgical instrument in the interior and allow a sterilant agent to enter the interior to sterilizer the surgical instrument, the sterilization container comprising:
  a valve coupled to the enclosure and rotatable between a closed state and an open state, said valve blocking communication between the interior of the surgical container and an exterior of the surgical container when said valve is rotated to said closed state;
  a sensor module removably coupled to said container and fluidly communicating through said valve with the interior of the surgical container when said valve is rotated to said open state; and
  a valve locking assembly coupled to said valve and preventing said valve from rotating to said open state, said valve locking assembly positioned within and accessible only from within the interior of the surgical container.

XLIX. The sterilization container of clause XLVIII, wherein said valve locking assembly is manually actuated from within the interior of the sterilization container.

L. The sterilization container of clause XLVIII, wherein said valve comprises:
  a valve cap having a hole fluidly communicating with the interior of the sterilization container; and a valve plate rotatable relative to said valve cap and having a bore fluidly communicating with said hole of said valve cap when said valve plate is rotated to said open state;

wherein said sensor module has a void and a sensor positioned within said void, said void fluidly communicating with said bore of the valve plate, said hole of said valve cap, and the interior of the sterilization container when the valve plate is rotated to said open state such that said void can receive a sterilant gas from the interior of the sterilization container and said sensor measures characteristics of said sterilant gas.

LI. The sterilization container of clause XLIX, wherein said bore does not fluidly communicate with said hole when said valve plate is rotated to said closed state, such that said valve prevents contaminants from entering the interior of the sterilization container.

LII. The sterilization container of clause XLIX, wherein said valve plate defines a channel in fluid communication between said bore of said valve plate and said hole of said valve cap when said valve plate is rotated to said open state, and said channel is not in fluid communication between said bore of said valve plate and said hole of said valve cap when said valve plate is rotated to said closed state.

LIII. The sterilization container of clause XLIX, wherein said sensor module is coupled to said valve plate to rotate with said valve plate.

LIV. The sterilization container of clause XLIX, further comprising a bezel plate configured to couple said sensor module to the sterilization container when said sensor module rotates said valve to said open state, and said bezel plate is configured to release said sensor module from the sterilization container when said sensor module rotates said valve to said closed state.

The invention claimed is:

1. A sterilization enclosure configured to be placed within a sterilizer, the sterilization enclosure configured to accommodate a surgical instrument for sterilization and defining an interior capable of fluidly communicating with the sterilizer to receive steam from the sterilizer, said sterilization enclosure comprising:
a phase change material notification device positioned within said interior of said enclosure or coupled to an exterior of said enclosure, said phase change material notification device comprising:
a housing defining an upper chamber and a lower chamber;
a phase change material positioned within said upper chamber, and configured to undergo a phase change and move from said upper chamber to said lower chamber; and
a baffle formed from a planar wall including one or more openings and positioned between said upper chamber and said lower chamber to allow said phase change material to move from said upper chamber to said lower chamber when a threshold amount of heat energy has been transferred to the phase change material from the steam of the sterilizer adjacent to said phase change material notification device; and
wherein said baffle having a top surface that is disposed in a non-horizontal position such that gravity allows a portion of said phase change material to move along said top surface before passing through said one or more openings in said baffle.

2. The sterilization enclosure of claim 1, wherein said phase change material notification device is removably coupled to said enclosure.

3. The sterilization enclosure of claim 1, wherein said phase change material notification device is rotatably coupled to said enclosure to selectively position said upper chamber above said lower chamber.

4. The sterilization enclosure of claim 1, wherein said enclosure comprises a transparent window through which at least a portion of said phase change material notification device is visible.

5. The sterilization enclosure of claim 4, wherein said enclosure comprises a container including a body and a lid coupled to said body, with at least one of said body and said lid having said transparent window integrated therein.

6. The sterilization enclosure of claim 4, wherein said enclosure comprises a sterile barrier wrap encompassing said phase change material notification device, said sterile barrier wrap having said transparent window integrated therein.

7. The sterilization enclosure of claim 1, wherein said housing comprises a marking corresponding with at least one of said upper chamber and said lower chamber to indicate an amount of said phase change material located within a corresponding one of said upper chamber and said lower chamber.

8. The sterilization enclosure of claim 1 wherein said baffle comprises an aperture, a longitudinal slot, or a combination thereof, each configured to prevent said phase change material of a predetermined size that has not undergone said phase change from moving from said upper chamber to said lower chamber.

9. The sterilization enclosure of claim 1, wherein said baffle comprises a plate, a screen, a grating, or a combination thereof.

10. The sterilization enclosure of claim 1, wherein said baffle prevents a bulk portion of said phase change material that has not undergone said phase change from moving from said upper chamber to said lower chamber.

11. The sterilization enclosure of claim 1, wherein said baffle comprises a grating.

12. The sterilization enclosure of claim 1, wherein said phase change material is configured to undergo reversible phase change.

13. The sterilization enclosure of claim 1, wherein said baffle is configured such that a portion of said phase change material, once melted, moves from said upper chamber to said lower chamber in response to the force of gravity.

14. A sterilization enclosure configured to be placed within a sterilizer, the sterilization enclosure configured to accommodate a surgical instrument for sterilization and defining an interior capable of fluidly communicating with the sterilizer to receive steam from the sterilizer, the sterilization enclosure comprising:
a phase change material notification device coupled to said enclosure, said phase change material notification device comprising:
a housing defining an upper chamber and a lower chamber;
a phase change material positioned within said upper chamber and configured to undergo a phase change and move from said upper chamber to said lower chamber; and
a baffle positioned between said upper chamber and said lower chamber to allow said phase change material to move from said upper chamber to said lower chamber when a threshold amount of heat energy has been transferred to the phase change material from the steam of the sterilizer adjacent to said phase change material notification device;

wherein said baffle comprises a grating having a top surface that is disposed in a non-horizontal position and a plurality of openings such that gravity allows a portion of said phase change material to move along said top surface before passing through one of said plurality of openings.

15. A phase change material notification device adapted for use with a sterilization enclosure configured to be placed within a sterilizer, the sterilization enclosure configured to accommodate a surgical instrument for sterilization and defining an interior capable of fluidly communicating with the sterilizer to receive steam from the sterilizer, the phase change material notification device comprising:
- a housing defining an upper chamber and a lower chamber;
- a phase change material positioned within said upper chamber and configured to undergo a phase change and move from said upper chamber to said lower chamber;
- a marking corresponding with at least one of said upper chamber and said lower chamber to indicate an amount of said phase change material located within a corresponding one of said upper chamber and said lower chamber; and
- a baffle formed from a planar wall including one or more openings and positioned between said upper chamber and said lower chamber to allow said phase change material to move from said upper chamber to said lower chamber,
- wherein said marking corresponds to a volume of phase change material that is indicative of a threshold amount of heat energy being transferred to the phase change material from the steam within the sterilizer, the threshold amount of heat energy correlated to a desired level of sterility; and
- wherein said baffle having a top surface that that extends from said housing within the interior by a non-perpendicular angle relative to a bottom of said phase change material notification device such that gravity allows a portion of said phase change material to move along said top surface before passing through said one or more openings in said baffle.

16. The sterilization enclosure of claim 1, wherein said phase change material comprises a single common color in an unmelted state and a melted stated after said phase change material has undergone said phase change.

17. The sterilization enclosure of claim 1, wherein said housing is comprised of a single material having a coefficient of thermal conductivity.

18. The sterilization container enclosure of claim 1, wherein said housing is comprised of two or more different materials having corresponding coefficients of thermal conductivity.

19. The sterilization enclosure of claim 1, wherein said phase change material notification device further comprises an insulation layer coupled to said housing and configured to regulate a rate of heat transfer through said housing to said phase change material.

20. The sterilization enclosure of claim 1, wherein at least one of said upper chamber, said lower chamber, and said grating is made from a material having different coefficient of thermal conductivity than the other.

21. The sterilization enclosure of claim 20, wherein the housing may be configured such that a portion of said housing defining a wall adjacent said grating comprises a first material having a higher coefficient of thermal conductivity than a second material defining said upper chamber and said lower chamber.

22. The sterilization enclosure of claim 19, wherein said upper chamber comprises an insulation layer made of a first material;
- wherein the lower chamber is covered by an insulation layer made of a second material; and
- wherein the first material comprises a thermal conductivity that is higher than the thermal conductivity of the second material.

23. The sterilization enclosure of claim 1, wherein a material of said housing combined with thermodynamic properties of the phase change material allows the phase change material notification device to be specifically sized and built to create a repeatable thermodynamic notification system wherein a known amount of the phase change material melts and thus flows into said lower chamber as a function of time for targeted steam sterilization conditions.

* * * * *